United States Patent
Burkart et al.

(10) Patent No.: US 12,090,046 B2
(45) Date of Patent: *Sep. 17, 2024

(54) TELESCOPING PROSTHETIC VALVE WITH RETENTION ELEMENT

(71) Applicant: EDWARDS LIFESCIENCES CORPORATION, Irvine, CA (US)

(72) Inventors: Dustin C. Burkart, Bellemont, AZ (US); Cody L. Hartman, Flagstaff, AZ (US); Ryan S. Titone, Flagstaff, AZ (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/736,704

(22) Filed: May 4, 2022

(65) Prior Publication Data

US 2022/0257369 A1    Aug. 18, 2022

Related U.S. Application Data

(63) Continuation of application No. 16/805,181, filed on Feb. 28, 2020, now Pat. No. 11,497,601.

(60) Provisional application No. 62/833,086, filed on Apr. 12, 2019, provisional application No. 62/812,782, filed on Mar. 1, 2019.

(51) Int. Cl.
*A61F 2/24*     (2006.01)
*A61F 2/00*     (2006.01)

(52) U.S. Cl.
CPC .......... *A61F 2/2409* (2013.01); *A61F 2/2418* (2013.01); *A61F 2/243* (2013.01); *A61F 2/2439* (2013.01); *A61F 2002/0081* (2013.01); *A61F 2230/005* (2013.01); *A61F 2250/0065* (2013.01)

(58) Field of Classification Search
CPC ........ A61F 2/24; A61F 2/2409; A61F 2/2418; A61F 2/243; A61F 2250/0056; A61F 2230/005; A61F 2002/0081
See application file for complete search history.

(56) References Cited

U.S. PATENT DOCUMENTS

| | | | |
|---|---|---|---|
| 654,799 | A | 7/1900 | Levett. |
| 3,739,402 | A | 6/1973 | Kahn et al. |
| 3,953,566 | A | 4/1976 | Gore |
| 4,178,639 | A | 12/1979 | Bokros |
| 4,187,390 | A | 2/1980 | Gore |
| 4,222,126 | A | 9/1980 | Boretos et al. |
| 4,265,694 | A | 5/1981 | Boretos et al. |
| 4,332,035 | A | 6/1982 | Mano |
| 4,340,091 | A | 7/1982 | Skelton et al. |

(Continued)

FOREIGN PATENT DOCUMENTS

| | | |
|---|---|---|
| AU | 2013363172 A1 | 7/2015 |
| AU | 2017202405 A1 | 4/2017 |

(Continued)

OTHER PUBLICATIONS

Cardiac Surgery in the Adult, Third Edition, Chapter 2 2008.

(Continued)

*Primary Examiner* — Dinah Baria
(74) *Attorney, Agent, or Firm* — Thomas C. Richardson

(57) ABSTRACT

An implantable device is disclosed. The device includes a leaflet frame subcomponent and an anchor frame subcomponent that are configured to be delivered in a series configuration and subsequently nested or telescoped in-situ.

19 Claims, 43 Drawing Sheets

(56) References Cited

U.S. PATENT DOCUMENTS

| | | |
|---|---|---|
| 4,477,930 A | 10/1984 | Totten et al. |
| 4,556,996 A | 12/1985 | Wallace |
| 4,626,255 A | 12/1986 | Reichart et al. |
| 4,759,759 A | 7/1988 | Walker et al. |
| 4,851,000 A | 7/1989 | Gupta |
| 4,877,661 A | 10/1989 | House et al. |
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,123,918 A | 6/1992 | Perrier et al. |
| 5,163,955 A | 11/1992 | Love et al. |
| 5,415,667 A | 5/1995 | Frater |
| 5,469,868 A | 11/1995 | Reger |
| 5,476,589 A | 12/1995 | Bacino |
| 5,489,297 A | 2/1996 | Duran |
| 5,534,007 A | 7/1996 | St. Germain et al. |
| 5,549,663 A | 8/1996 | Cottone, Jr. |
| 5,554,183 A | 9/1996 | Nazari |
| 5,554,185 A | 9/1996 | Block et al. |
| 5,562,729 A | 10/1996 | Purdy |
| 5,628,791 A | 5/1997 | Bokros et al. |
| 5,673,102 A | 9/1997 | Suzuki et al. |
| 5,708,044 A | 1/1998 | Branca |
| 5,718,973 A | 2/1998 | Lewis et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Enker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,928,281 A | 7/1999 | Huynh et al. |
| 5,935,162 A | 8/1999 | Dang |
| 5,935,163 A | 8/1999 | Gabbay |
| 5,944,654 A | 8/1999 | Crawford |
| 5,957,974 A | 9/1999 | Thompson et al. |
| 6,010,529 A | 1/2000 | Herweck et al. |
| 6,013,854 A | 1/2000 | Moriuchi |
| 6,019,785 A | 2/2000 | Strecker |
| 6,042,588 A | 3/2000 | Munsinger et al. |
| 6,042,605 A | 3/2000 | Martin et al. |
| 6,042,606 A | 3/2000 | Frantzen |
| 6,086,612 A | 7/2000 | Jansen |
| 6,110,198 A | 8/2000 | Fogarty et al. |
| 6,117,169 A | 9/2000 | Moe |
| 6,129,758 A | 10/2000 | Love |
| 6,161,399 A | 12/2000 | Jayaraman |
| 6,165,211 A | 12/2000 | Thompson |
| 6,171,335 B1 | 1/2001 | Wheatley et al. |
| 6,174,329 B1 | 1/2001 | Callol et al. |
| 6,174,331 B1 | 1/2001 | Moe et al. |
| 6,190,406 B1 | 2/2001 | Duerig et al. |
| 6,197,143 B1 | 3/2001 | Bodnar |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,283,994 B1 | 9/2001 | Moe et al. |
| 6,283,995 B1 | 9/2001 | Moe et al. |
| 6,287,334 B1 | 9/2001 | Moll et al. |
| 6,328,763 B1 | 12/2001 | Love et al. |
| 6,334,873 B1 | 1/2002 | Lane et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,436,132 B1 | 8/2002 | Patel et al. |
| 6,454,798 B1 | 9/2002 | Moe |
| 6,454,799 B1 | 9/2002 | Schreck |
| 6,461,382 B1 | 10/2002 | Cao |
| 6,461,665 B1 | 10/2002 | Scholander |
| 6,482,228 B1 | 11/2002 | Norred |
| 6,488,701 B1 | 12/2002 | Nolting et al. |
| 6,541,589 B1 | 4/2003 | Baillie |
| 6,558,418 B2 | 5/2003 | Carpentier et al. |
| 6,562,069 B2 | 5/2003 | Cai et al. |
| 6,582,464 B2 | 6/2003 | Gabbay |
| 6,613,086 B1 | 9/2003 | Moe et al. |
| 6,620,190 B1 | 9/2003 | Colone |
| 6,626,939 B1 | 9/2003 | Burnside et al. |
| 6,645,244 B2 | 11/2003 | Shu et al. |
| 6,666,885 B2 | 12/2003 | Moe |
| 6,673,102 B1 | 1/2004 | Vonesh et al. |
| 6,673,107 B1 | 1/2004 | Brandt et al. |
| 6,726,715 B2 | 4/2004 | Sutherland |
| 6,730,118 B2 | 5/2004 | Spenser et al. |
| 6,730,120 B2 | 5/2004 | Berg et al. |
| 6,755,856 B2 | 6/2004 | Fierens et al. |
| 6,755,857 B2 | 6/2004 | Peterson et al. |
| 6,758,858 B2 | 7/2004 | McCrea et al. |
| 6,890,350 B1 | 5/2005 | Walak |
| 6,893,460 B2 | 5/2005 | Spenser et al. |
| 6,916,338 B2 | 7/2005 | Speziali |
| 6,936,067 B2 | 8/2005 | Buchanan |
| 6,953,332 B1 | 10/2005 | Kurk et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,137,184 B2 | 11/2006 | Schreck |
| 7,163,556 B2 | 1/2007 | Xie et al. |
| 7,238,200 B2 | 7/2007 | Lee et al. |
| 7,247,167 B2 | 7/2007 | Gabbay |
| 7,306,729 B2 | 12/2007 | Bacino et al. |
| 7,381,218 B2 | 6/2008 | Schreck |
| 7,419,678 B2 | 9/2008 | Falotico |
| 7,462,675 B2 | 12/2008 | Chang et al. |
| 7,510,575 B2 | 3/2009 | Spenser et al. |
| 7,513,909 B2 | 4/2009 | Lane et al. |
| 7,531,611 B2 | 5/2009 | Sabol et al. |
| 7,563,277 B2 | 7/2009 | Case et al. |
| 7,708,775 B2 | 5/2010 | Rowe et al. |
| 7,727,274 B2 | 6/2010 | Zilla et al. |
| 7,758,640 B2 | 7/2010 | Vesely |
| 7,780,725 B2 | 8/2010 | Haug et al. |
| 7,789,908 B2 | 9/2010 | Sowinski et al. |
| 7,803,186 B1 | 9/2010 | Li et al. |
| 7,811,314 B2 | 10/2010 | Fierens et al. |
| 7,815,763 B2 | 10/2010 | Fierens et al. |
| 7,879,085 B2 | 2/2011 | Sowinski et al. |
| 7,887,562 B2 | 2/2011 | Young et al. |
| 7,914,569 B2 | 3/2011 | Nguyen et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 7,967,853 B2 | 6/2011 | Eidenschink et al. |
| 7,993,394 B2 | 8/2011 | Hariton et al. |
| 8,048,440 B2 | 11/2011 | Chang et al. |
| 8,062,359 B2 | 11/2011 | Marquez et al. |
| 8,092,523 B2 | 1/2012 | Li et al. |
| 8,167,935 B2 | 5/2012 | McGuckin et al. |
| 8,226,710 B2 | 7/2012 | Nguyen et al. |
| 8,246,678 B2 | 8/2012 | Salahieh et al. |
| 8,252,037 B2 | 8/2012 | Styrc et al. |
| 8,303,647 B2 | 11/2012 | Case |
| 8,349,000 B2 | 1/2013 | Schreck |
| 8,409,274 B2 | 4/2013 | Li et al. |
| 8,475,512 B2 | 7/2013 | Hunt |
| 8,545,525 B2 | 10/2013 | Surti et al. |
| 8,568,475 B2 | 10/2013 | Nguyen et al. |
| 8,585,753 B2 | 11/2013 | Scanlon et al. |
| 8,585,757 B2 | 11/2013 | Agathos |
| 8,628,566 B2 | 1/2014 | Eberhardt et al. |
| 8,637,144 B2 | 1/2014 | Ford |
| 8,709,077 B2 | 4/2014 | Schreck |
| 8,722,178 B2 | 5/2014 | Ashmead et al. |
| 8,728,103 B2 | 5/2014 | Surti et al. |

(56) References Cited

U.S. PATENT DOCUMENTS

| | | |
|---|---|---|
| 8,728,154 B2 | 5/2014 | Alkhatib |
| 8,784,481 B2 | 7/2014 | Alkhatib et al. |
| 8,801,774 B2 | 8/2014 | Silverman |
| 8,808,848 B2 | 8/2014 | Bacino |
| 8,845,709 B2 | 9/2014 | Styrc et al. |
| 8,845,721 B2 | 9/2014 | Braido et al. |
| 8,852,272 B2 | 10/2014 | Gross et al. |
| 8,870,948 B1 | 10/2014 | Erzberger et al. |
| 8,936,634 B2 | 1/2015 | Irwin et al. |
| 8,945,212 B2 | 2/2015 | Bruchman et al. |
| 8,961,599 B2 | 2/2015 | Bruchman et al. |
| 8,992,608 B2 | 3/2015 | Haug et al. |
| 9,039,757 B2 | 5/2015 | McLean et al. |
| 9,101,469 B2 | 8/2015 | Bruchman et al. |
| 9,101,696 B2 | 8/2015 | Leontein et al. |
| 9,107,771 B2 | 8/2015 | Wubbeling et al. |
| 9,125,740 B2 | 9/2015 | Morriss et al. |
| 9,139,669 B2 | 9/2015 | Xu et al. |
| 9,144,492 B2 | 9/2015 | Bruchman et al. |
| 9,168,131 B2 | 10/2015 | Yohanan et al. |
| 9,198,787 B2 | 12/2015 | Kratzberg et al. |
| 9,241,695 B2 | 1/2016 | Peavey et al. |
| 9,259,313 B2 | 2/2016 | Wheatley |
| 9,283,072 B2 | 3/2016 | Bruchman et al. |
| 9,295,552 B2 | 3/2016 | McLean et al. |
| 9,314,355 B2 | 4/2016 | Styrc et al. |
| 9,345,601 B2 | 5/2016 | Jantzen et al. |
| 9,375,308 B2 | 6/2016 | Norris |
| 9,393,110 B2 | 7/2016 | Levi et al. |
| 9,398,952 B2 | 7/2016 | Bruchman et al. |
| 9,399,085 B2 | 7/2016 | Cleek et al. |
| 9,504,565 B2 | 11/2016 | Armstrong |
| 9,554,786 B2 | 1/2017 | Carley et al. |
| 9,554,900 B2 | 1/2017 | Bruchman et al. |
| 9,597,181 B2 | 3/2017 | Christianson et al. |
| 9,629,718 B2 | 4/2017 | Gloss et al. |
| 9,681,948 B2 | 6/2017 | Levi et al. |
| 9,737,398 B2 | 8/2017 | Bruchman et al. |
| 9,737,422 B2 | 8/2017 | Armstrong et al. |
| 9,743,932 B2 | 8/2017 | Amplatz et al. |
| 9,795,496 B2 | 10/2017 | Armstrong et al. |
| 9,801,712 B2 | 10/2017 | Bruchman et al. |
| 9,827,089 B2 | 11/2017 | Bruchman et al. |
| 9,827,094 B2 | 11/2017 | Bennett |
| 9,839,540 B2 | 12/2017 | Armstrong et al. |
| 9,855,141 B2 | 1/2018 | Dienno et al. |
| 9,931,193 B2 | 4/2018 | Cully et al. |
| 9,931,204 B2 | 4/2018 | Rothstein et al. |
| 9,937,037 B2 | 4/2018 | Dienno et al. |
| 9,968,443 B2 | 5/2018 | Bruchman et al. |
| 10,039,638 B2 | 8/2018 | Bruchman et al. |
| 10,166,128 B2 | 1/2019 | Armstrong et al. |
| 10,279,084 B2 | 5/2019 | Goepfrich et al. |
| 10,285,808 B2 | 5/2019 | Bruchman et al. |
| 10,314,697 B2 | 6/2019 | Gassler |
| 10,321,986 B2 | 6/2019 | Bruchman et al. |
| 10,335,298 B2 | 7/2019 | Armstrong et al. |
| 10,342,659 B2 | 7/2019 | Bennett |
| 10,368,984 B2 | 8/2019 | Armstrong |
| 10,376,360 B2 | 8/2019 | Bruchman et al. |
| 10,441,416 B2 | 10/2019 | Oba et al. |
| 10,463,478 B2 | 11/2019 | Bruchman et al. |
| 10,507,124 B2 | 12/2019 | Armstrong et al. |
| 10,639,144 B2 | 5/2020 | Bruchman et al. |
| 10,660,745 B2 | 5/2020 | Bruchman et al. |
| 10,881,507 B2 | 1/2021 | Bruchman et al. |
| 10,980,633 B2 | 4/2021 | Dienno et al. |
| 11,020,221 B2 | 6/2021 | Arcaro et al. |
| 11,039,917 B2 | 6/2021 | Bruchman et al. |
| D926,322 S | 7/2021 | Bennett et al. |
| 11,065,112 B2 | 7/2021 | Gassler |
| 11,090,153 B2 | 8/2021 | Haarer et al. |
| 11,109,963 B2 | 9/2021 | Dienno et al. |
| 11,123,183 B2 | 9/2021 | Bennett et al. |
| 11,439,502 B2 | 9/2022 | Busalacchi et al. |
| 11,471,276 B2 | 10/2022 | Bennett |
| 2001/0053929 A1 | 12/2001 | Vonesh et al. |
| 2002/0045936 A1 | 4/2002 | Moe |
| 2002/0055773 A1 | 5/2002 | Campbell et al. |
| 2002/0076542 A1 | 6/2002 | Kramer et al. |
| 2002/0082687 A1 | 6/2002 | Moe |
| 2002/0133226 A1 | 9/2002 | Marquez et al. |
| 2002/0151953 A1 | 10/2002 | Chobotov et al. |
| 2002/0151956 A1 | 10/2002 | Chobotov et al. |
| 2002/0183840 A1 | 12/2002 | Lapeyre et al. |
| 2002/0198588 A1 | 12/2002 | Armstrong et al. |
| 2002/0198594 A1 | 12/2002 | Schreck |
| 2003/0014105 A1 | 1/2003 | Cao |
| 2003/0027332 A1 | 2/2003 | Lafrance et al. |
| 2003/0055494 A1 | 3/2003 | Bezuidenhout et al. |
| 2003/0055496 A1 | 3/2003 | Cai et al. |
| 2003/0060871 A1 | 3/2003 | Hill et al. |
| 2003/0074052 A1 | 4/2003 | Besselink et al. |
| 2003/0097175 A1 | 5/2003 | O'Connor et al. |
| 2003/0114913 A1 | 6/2003 | Spenser et al. |
| 2003/0125805 A1 | 7/2003 | Johnson et al. |
| 2003/0180488 A1 | 9/2003 | Lim et al. |
| 2003/0209835 A1 | 11/2003 | Chun et al. |
| 2003/0229394 A1 | 12/2003 | Ogle et al. |
| 2004/0024442 A1 | 2/2004 | Sowinski et al. |
| 2004/0024448 A1 | 2/2004 | Chang et al. |
| 2004/0024451 A1 | 2/2004 | Johnson et al. |
| 2004/0026245 A1 | 2/2004 | Agarwal et al. |
| 2004/0039436 A1 | 2/2004 | Spenser et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0176839 A1 | 9/2004 | Huynh et al. |
| 2004/0224442 A1 | 11/2004 | Grigg |
| 2004/0243222 A1 | 12/2004 | Osborne et al. |
| 2004/0260277 A1 | 12/2004 | Maguire |
| 2004/0260389 A1 | 12/2004 | Case et al. |
| 2004/0260393 A1 | 12/2004 | Rahdert et al. |
| 2005/0027348 A1 | 2/2005 | Case et al. |
| 2005/0080476 A1 | 4/2005 | Gunderson et al. |
| 2005/0119722 A1 | 6/2005 | Styrc et al. |
| 2005/0137680 A1 | 6/2005 | Ortiz et al. |
| 2005/0137682 A1 | 6/2005 | Justino |
| 2005/0203614 A1 | 9/2005 | Forster et al. |
| 2005/0261765 A1 | 11/2005 | Liddicoat |
| 2005/0283224 A1 | 12/2005 | King |
| 2006/0008497 A1 | 1/2006 | Gabbay |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0041091 A1 | 2/2006 | Chang et al. |
| 2006/0106337 A1 | 5/2006 | Blankenship |
| 2006/0118236 A1 | 6/2006 | House et al. |
| 2006/0122693 A1 | 6/2006 | Biadillah et al. |
| 2006/0135985 A1 | 6/2006 | Cox et al. |
| 2006/0154365 A1 | 7/2006 | Ratcliffe et al. |
| 2006/0161241 A1 | 7/2006 | Barbut et al. |
| 2006/0190070 A1 | 8/2006 | Dieck et al. |
| 2006/0229718 A1 | 10/2006 | Marquez |
| 2006/0229719 A1 | 10/2006 | Marquez et al. |
| 2006/0259133 A1 | 11/2006 | Sowinski et al. |
| 2006/0259136 A1 | 11/2006 | Nguyen et al. |
| 2006/0265053 A1 | 11/2006 | Hunt |
| 2006/0271091 A1 | 11/2006 | Campbell et al. |
| 2006/0276813 A1 | 12/2006 | Greenberg |
| 2006/0276883 A1 | 12/2006 | Greenberg et al. |
| 2006/0276888 A1 | 12/2006 | Lee et al. |
| 2006/0282162 A1 | 12/2006 | Nguyen et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2007/0010876 A1 | 1/2007 | Salahieh et al. |
| 2007/0012624 A1 | 1/2007 | Bacino et al. |
| 2007/0021826 A1 | 1/2007 | Case et al. |
| 2007/0060999 A1 | 3/2007 | Randall et al. |
| 2007/0100435 A1 | 5/2007 | Case et al. |
| 2007/0118210 A1 | 5/2007 | Pinchuk |
| 2007/0129786 A1 | 6/2007 | Beach et al. |

(56) References Cited

U.S. PATENT DOCUMENTS

| | | |
|---|---|---|
| 2007/0207186 A1 | 9/2007 | Scanlon et al. |
| 2007/0207816 A1 | 9/2007 | Spain, Jr. |
| 2007/0208417 A1 | 9/2007 | Agnew |
| 2007/0208421 A1 | 9/2007 | Quigley |
| 2007/0213800 A1 | 9/2007 | Fierens et al. |
| 2007/0244552 A1 | 10/2007 | Salahieh et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0009940 A1 | 1/2008 | Cribier |
| 2008/0026190 A1 | 1/2008 | King et al. |
| 2008/0039934 A1 | 2/2008 | Styrc |
| 2008/0051876 A1 | 2/2008 | Ta et al. |
| 2008/0065198 A1 | 3/2008 | Quintessenza |
| 2008/0071369 A1 | 3/2008 | Tuval et al. |
| 2008/0082154 A1 | 4/2008 | Tseng et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0133004 A1 | 6/2008 | White |
| 2008/0140178 A1 | 6/2008 | Rasmussen et al. |
| 2008/0195199 A1 | 8/2008 | Kheradvar et al. |
| 2008/0208327 A1 | 8/2008 | Rowe |
| 2008/0220041 A1 | 9/2008 | Brito et al. |
| 2008/0228263 A1 | 9/2008 | Ryan |
| 2008/0300678 A1 | 12/2008 | Eidenschink et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0099640 A1 | 4/2009 | Weng |
| 2009/0104247 A1 | 4/2009 | Pacetti |
| 2009/0117334 A1 | 5/2009 | Sogard et al. |
| 2009/0138079 A1 | 5/2009 | Tuval et al. |
| 2009/0157175 A1 | 6/2009 | Benichou |
| 2009/0182413 A1 | 7/2009 | Burkart et al. |
| 2009/0240320 A1 | 9/2009 | Tuval et al. |
| 2009/0264997 A1 | 10/2009 | Salahieh et al. |
| 2009/0276039 A1 | 11/2009 | Meretei |
| 2009/0281609 A1 | 11/2009 | Benichou et al. |
| 2009/0287305 A1 | 11/2009 | Amalaha |
| 2009/0292350 A1 | 11/2009 | Eberhardt et al. |
| 2009/0306762 A1 | 12/2009 | McCullagh et al. |
| 2009/0306766 A1 | 12/2009 | McDermott et al. |
| 2010/0016940 A1 | 1/2010 | Shokoohi et al. |
| 2010/0023114 A1 | 1/2010 | Chambers et al. |
| 2010/0036021 A1 | 2/2010 | Lee et al. |
| 2010/0036484 A1 | 2/2010 | Hariton et al. |
| 2010/0049294 A1 | 2/2010 | Zukowski et al. |
| 2010/0082089 A1 | 4/2010 | Quadri et al. |
| 2010/0082094 A1 | 4/2010 | Quadri et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0114307 A1 | 5/2010 | Agnew et al. |
| 2010/0131056 A1 | 5/2010 | Lapeyre |
| 2010/0137998 A1 | 6/2010 | Sobrino-Serrano et al. |
| 2010/0145438 A1 | 6/2010 | Barone |
| 2010/0159171 A1 | 6/2010 | Clough |
| 2010/0168839 A1 | 7/2010 | Braido et al. |
| 2010/0185274 A1 | 7/2010 | Moaddeb et al. |
| 2010/0185277 A1 | 7/2010 | Braido et al. |
| 2010/0191320 A1 | 7/2010 | Straubinger et al. |
| 2010/0204781 A1 | 8/2010 | Alkhatib |
| 2010/0204785 A1 | 8/2010 | Alkhatib |
| 2010/0211165 A1 | 8/2010 | Schreck |
| 2010/0217382 A1 | 8/2010 | Chau et al. |
| 2010/0248324 A1 | 9/2010 | Xu et al. |
| 2010/0249923 A1 | 9/2010 | Alkhatib et al. |
| 2010/0256738 A1 | 10/2010 | Berglund |
| 2010/0262231 A1 | 10/2010 | Tuval et al. |
| 2010/0286760 A1 | 11/2010 | Beach et al. |
| 2010/0298931 A1 | 11/2010 | Quadri et al. |
| 2010/0305682 A1 | 12/2010 | Furst |
| 2011/0009953 A1 | 1/2011 | Luk et al. |
| 2011/0040366 A1 | 2/2011 | Goetz et al. |
| 2011/0054515 A1 | 3/2011 | Bridgeman et al. |
| 2011/0064781 A1 | 3/2011 | Cleek et al. |
| 2011/0087318 A1 | 4/2011 | Daugherty et al. |
| 2011/0160836 A1 | 6/2011 | Behan |
| 2011/0172784 A1 | 7/2011 | Richter et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2011/0257739 A1 | 10/2011 | Corbett |
| 2011/0282439 A1 | 11/2011 | Thill et al. |
| 2011/0295363 A1 | 12/2011 | Girard et al. |
| 2012/0035722 A1 | 2/2012 | Tuval |
| 2012/0078357 A1 | 3/2012 | Conklin |
| 2012/0083839 A1 | 4/2012 | Letac et al. |
| 2012/0089223 A1 | 4/2012 | Nguyen et al. |
| 2012/0101567 A1 | 4/2012 | Jansen |
| 2012/0101571 A1 | 4/2012 | Thambar et al. |
| 2012/0116496 A1 | 5/2012 | Chuter et al. |
| 2012/0116498 A1 | 5/2012 | Chuter et al. |
| 2012/0123529 A1 | 5/2012 | Levi et al. |
| 2012/0123530 A1 | 5/2012 | Carpentier et al. |
| 2012/0130468 A1 | 5/2012 | Khosravi et al. |
| 2012/0130471 A1 | 5/2012 | Shoemaker et al. |
| 2012/0185038 A1 | 7/2012 | Fish et al. |
| 2012/0215303 A1 | 8/2012 | Quadri et al. |
| 2012/0253453 A1 | 10/2012 | Bruchman et al. |
| 2012/0277734 A1 | 11/2012 | Goetz et al. |
| 2012/0290082 A1 | 11/2012 | Quint et al. |
| 2012/0323211 A1 | 12/2012 | Ogle et al. |
| 2012/0323315 A1 | 12/2012 | Bruchman et al. |
| 2013/0018456 A1 | 1/2013 | Li et al. |
| 2013/0018458 A1 | 1/2013 | Yohanan et al. |
| 2013/0079700 A1 | 3/2013 | Ballard et al. |
| 2013/0110229 A1 | 5/2013 | Bokeriya et al. |
| 2013/0116655 A1 | 5/2013 | Bacino et al. |
| 2013/0131780 A1 | 5/2013 | Armstrong et al. |
| 2013/0150956 A1 | 6/2013 | Yohanan et al. |
| 2013/0158647 A1 | 6/2013 | Norris et al. |
| 2013/0166021 A1 | 6/2013 | Bruchman et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0204360 A1 | 8/2013 | Gainor |
| 2013/0253466 A1 | 9/2013 | Campbell et al. |
| 2013/0297003 A1 | 11/2013 | Pinchuk |
| 2013/0338755 A1 | 12/2013 | Goetz et al. |
| 2014/0005771 A1 | 1/2014 | Braido et al. |
| 2014/0005773 A1 | 1/2014 | Wheatley |
| 2014/0031924 A1 | 1/2014 | Bruchman et al. |
| 2014/0031927 A1 | 1/2014 | Bruchman et al. |
| 2014/0094898 A1 | 4/2014 | Borck |
| 2014/0106951 A1 | 4/2014 | Brandon |
| 2014/0135897 A1 | 5/2014 | Cully et al. |
| 2014/0163671 A1 | 6/2014 | Bruchman et al. |
| 2014/0163673 A1 | 6/2014 | Bruchman et al. |
| 2014/0172066 A1 | 6/2014 | Goepfrich et al. |
| 2014/0172069 A1 | 6/2014 | Roeder et al. |
| 2014/0172077 A1 | 6/2014 | Bruchman et al. |
| 2014/0172078 A1 | 6/2014 | Bruchman et al. |
| 2014/0172079 A1 | 6/2014 | Bruchman et al. |
| 2014/0172082 A1 | 6/2014 | Bruchman et al. |
| 2014/0172083 A1 | 6/2014 | Bruchman et al. |
| 2014/0180400 A1 | 6/2014 | Bruchman et al. |
| 2014/0180402 A1 | 6/2014 | Bruchman et al. |
| 2014/0194968 A1 | 7/2014 | Zukowski |
| 2014/0222140 A1 | 8/2014 | Schreck |
| 2014/0236289 A1 | 8/2014 | Alkhatib |
| 2014/0277413 A1 | 9/2014 | Arnold et al. |
| 2014/0277418 A1 | 9/2014 | Miller |
| 2014/0296969 A1 | 10/2014 | Tegels et al. |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0343670 A1 | 11/2014 | Bakis et al. |

(56) References Cited

U.S. PATENT DOCUMENTS

| | | |
|---|---|---|
| 2015/0005870 A1 | 1/2015 | Kovach et al. |
| 2015/0018944 A1 | 1/2015 | O'Connell et al. |
| 2015/0088250 A1 | 3/2015 | Zeng et al. |
| 2015/0105856 A1 | 4/2015 | Rowe et al. |
| 2015/0142100 A1 | 5/2015 | Morriss et al. |
| 2015/0157456 A1 | 6/2015 | Armstrong |
| 2015/0157770 A1 | 6/2015 | Cully et al. |
| 2015/0224231 A1 | 8/2015 | Bruchman et al. |
| 2015/0245910 A1 | 9/2015 | Righini et al. |
| 2015/0313871 A1 | 11/2015 | Li et al. |
| 2015/0366663 A1 | 12/2015 | Bruchman et al. |
| 2015/0366664 A1 | 12/2015 | Guttenberg et al. |
| 2016/0001469 A1 | 1/2016 | Bacchereti et al. |
| 2016/0015422 A1 | 1/2016 | De et al. |
| 2016/0074161 A1 | 3/2016 | Bennett |
| 2016/0106537 A1 | 4/2016 | Christianson et al. |
| 2016/0113699 A1 | 4/2016 | Sverdlik et al. |
| 2016/0157998 A1 | 6/2016 | Bruchman et al. |
| 2016/0175095 A1 | 6/2016 | Dienno et al. |
| 2016/0175096 A1 | 6/2016 | Dienno et al. |
| 2016/0206424 A1 | 7/2016 | Al-Jilaihawi et al. |
| 2016/0213465 A1 | 7/2016 | Girard et al. |
| 2016/0235525 A1 | 8/2016 | Rothstein et al. |
| 2016/0250051 A1 | 9/2016 | Lim et al. |
| 2016/0310268 A1 | 10/2016 | Oba et al. |
| 2016/0317299 A1 | 11/2016 | Alkhatib |
| 2017/0027727 A1 | 2/2017 | Wuebbeling et al. |
| 2017/0042674 A1 | 2/2017 | Armstrong |
| 2017/0056169 A1 | 3/2017 | Johnson et al. |
| 2017/0065400 A1 | 3/2017 | Armstrong et al. |
| 2017/0095330 A1 | 4/2017 | Malewicz et al. |
| 2017/0095331 A1 | 4/2017 | Spenser et al. |
| 2017/0100236 A1 | 4/2017 | Robertson et al. |
| 2017/0105854 A1 | 4/2017 | Treacy et al. |
| 2017/0106176 A1 | 4/2017 | Taft et al. |
| 2017/0128199 A1 | 5/2017 | Gurovich et al. |
| 2017/0156859 A1 | 6/2017 | Chang et al. |
| 2017/0165066 A1 | 6/2017 | Rothstein |
| 2017/0165067 A1 | 6/2017 | Barajas-Torres et al. |
| 2017/0216062 A1 | 8/2017 | Armstrong et al. |
| 2017/0224481 A1 | 8/2017 | Spenser et al. |
| 2017/0252153 A1 | 9/2017 | Chau et al. |
| 2017/0348101 A1 | 12/2017 | Vaughn et al. |
| 2018/0021128 A1 | 1/2018 | Bruchman et al. |
| 2018/0021129 A1 | 1/2018 | Peterson et al. |
| 2018/0125646 A1 | 5/2018 | Bruchman et al. |
| 2018/0177583 A1 | 6/2018 | Cully et al. |
| 2018/0221144 A1 | 8/2018 | Bruchman et al. |
| 2018/0271651 A1 | 9/2018 | Christianson et al. |
| 2018/0271653 A1 | 9/2018 | Vidlund et al. |
| 2018/0318070 A1 | 11/2018 | Bruchman et al. |
| 2019/0076245 A1 | 3/2019 | Arcaro et al. |
| 2019/0091014 A1 | 3/2019 | Arcaro et al. |
| 2019/0091015 A1 | 3/2019 | Dienno et al. |
| 2019/0110893 A1 | 4/2019 | Haarer et al. |
| 2019/0125517 A1 | 5/2019 | Cully et al. |
| 2019/0125528 A1 | 5/2019 | Busalacchi et al. |
| 2019/0125530 A1 | 5/2019 | Arcaro et al. |
| 2019/0125531 A1 | 5/2019 | Bennett et al. |
| 2019/0125534 A1 | 5/2019 | Arcaro et al. |
| 2019/0209292 A1 | 7/2019 | Bruchman et al. |
| 2019/0209739 A1 | 7/2019 | Goepfrich et al. |
| 2019/0216592 A1 | 7/2019 | Cully et al. |
| 2019/0247185 A1 | 8/2019 | Gassler |
| 2019/0254815 A1 | 8/2019 | Bruchman et al. |
| 2019/0269505 A1 | 9/2019 | Bruchman et al. |
| 2019/0314154 A1 | 10/2019 | Armstrong |
| 2019/0328525 A1 | 10/2019 | Noe et al. |
| 2019/0374339 A1 | 12/2019 | Bennett |
| 2020/0000578 A1 | 1/2020 | Bruchman et al. |
| 2020/0022828 A1 | 1/2020 | Armstrong et al. |
| 2020/0179663 A1 | 6/2020 | McDaniel et al. |
| 2020/0237497 A1 | 7/2020 | Silverman et al. |
| 2020/0237505 A1 | 7/2020 | Bruchman et al. |
| 2020/0246137 A1 | 8/2020 | Bruchman et al. |
| 2020/0276014 A1 | 9/2020 | Burkart et al. |
| 2020/0323631 A1 | 10/2020 | Chuter et al. |
| 2021/0121289 A1 | 4/2021 | Bruchman et al. |
| 2021/0177589 A1 | 6/2021 | Arcaro et al. |
| 2021/0205074 A1 | 7/2021 | Bruchman et al. |
| 2021/0307905 A1 | 10/2021 | Arcaro et al. |
| 2021/0338422 A1 | 11/2021 | Dienno et al. |
| 2021/0346156 A1 | 11/2021 | Haarer et al. |
| 2021/0361420 A1 | 11/2021 | Bennett et al. |
| 2021/0393399 A1 | 12/2021 | Arcaro et al. |
| 2022/0000611 A1 | 1/2022 | Arcaro et al. |
| 2022/0023032 A1 | 1/2022 | Bruchman et al. |
| 2022/0183831 A1 | 6/2022 | Burkart et al. |
| 2022/0273426 A1 | 9/2022 | Hagaman et al. |
| 2022/0378575 A1 | 12/2022 | Busalacchi et al. |
| 2023/0000623 A1 | 1/2023 | Bennett |

FOREIGN PATENT DOCUMENTS

| | | |
|---|---|---|
| CA | 2297536 A1 | 12/2000 |
| CA | 2462509 A1 | 4/2003 |
| CA | 2849030 A1 | 4/2013 |
| CA | 2878691 A1 | 1/2014 |
| CA | 2964546 A1 | 1/2014 |
| CA | 2960034 A1 | 3/2016 |
| CN | 101057796 A | 10/2007 |
| CN | 101091675 A | 12/2007 |
| CN | 101188985 A | 5/2008 |
| CN | 101374477 A | 2/2009 |
| CN | 101420913 A | 4/2009 |
| CN | 101849863 A | 10/2010 |
| CN | 101902989 A | 12/2010 |
| CN | 101926699 A | 12/2010 |
| CN | 201744060 U | 2/2011 |
| CN | 102015009 A | 4/2011 |
| CN | 102119013 A | 7/2011 |
| CN | 102292053 A | 12/2011 |
| CN | 102438546 A | 5/2012 |
| CN | 102573703 A | 7/2012 |
| CN | 102652694 A | 9/2012 |
| CN | 102724937 A | 10/2012 |
| CN | 102764169 A | 11/2012 |
| CN | 102791223 A | 11/2012 |
| CN | 102883684 A | 1/2013 |
| CN | 103079498 A | 5/2013 |
| CN | 103228232 A | 7/2013 |
| CN | 103237524 A | 8/2013 |
| CN | 103384505 A | 11/2013 |
| CN | 103732183 A | 4/2014 |
| CN | 103781439 A | 5/2014 |
| CN | 103945796 A | 7/2014 |
| CN | 104114127 A | 10/2014 |
| CN | 104487023 A | 4/2015 |
| CN | 104507417 A | 4/2015 |
| CN | 104869948 A | 8/2015 |
| CN | 105007955 A | 10/2015 |
| CN | 105101911 A | 11/2015 |
| CN | 105263445 A | 1/2016 |
| CN | 105662651 A | 6/2016 |
| CN | 105792780 A | 7/2016 |
| CN | 106668949 A | 5/2017 |
| CN | 106714733 A | 5/2017 |
| CN | 106794065 A | 5/2017 |
| CN | 107106294 A | 8/2017 |
| CN | 107690323 A | 2/2018 |
| CN | 108578016 A | 9/2018 |
| DE | 212013000104 U1 | 11/2014 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1057460 A1 | 12/2000 |
| EP | 1318775 A1 | 6/2003 |
| EP | 1666003 A1 | 6/2006 |
| EP | 1395205 B1 | 7/2008 |
| EP | 1235537 B1 | 12/2008 |
| EP | 2193762 A1 | 6/2010 |

(56) References Cited

FOREIGN PATENT DOCUMENTS

| | | |
|---|---|---|
| EP | 2255750 A2 | 12/2010 |
| EP | 2400923 A1 | 1/2012 |
| EP | 2489331 A2 | 8/2012 |
| EP | 2359774 B1 | 1/2013 |
| EP | 2591100 A2 | 5/2013 |
| EP | 2109417 B1 | 11/2013 |
| EP | 3142608 A1 | 3/2017 |
| EP | 3797738 A1 | 3/2021 |
| EP | 2948103 B1 | 12/2022 |
| FR | 2591100 A1 | 6/1987 |
| GB | 2312485 A | 10/1997 |
| GB | 2513194 A | 10/2014 |
| JP | 44-032400 | 12/1969 |
| JP | 1969-032400 B | 12/1969 |
| JP | 02-000645 A | 1/1990 |
| JP | 09-241412 A | 9/1997 |
| JP | 10-507097 A | 7/1998 |
| JP | 11-290448 A | 10/1999 |
| JP | 11-512635 A | 11/1999 |
| JP | 2000-511459 A | 9/2000 |
| JP | 2000-513248 A | 10/2000 |
| JP | 2001-000460 A | 1/2001 |
| JP | 2001-508641 A | 7/2001 |
| JP | 2001-508681 A | 7/2001 |
| JP | 2001-509702 A | 7/2001 |
| JP | 2001-511030 A | 8/2001 |
| JP | 2002-525169 A | 8/2002 |
| JP | 2002-541915 A | 12/2002 |
| JP | 2004-510471 A | 4/2004 |
| JP | 2005-500101 A | 1/2005 |
| JP | 2005-512611 A | 5/2005 |
| JP | 2005-514108 A | 5/2005 |
| JP | 2007-525291 A | 9/2007 |
| JP | 2007-526098 A | 9/2007 |
| JP | 2007-536989 A | 12/2007 |
| JP | 2008-506459 A | 3/2008 |
| JP | 2008-535572 A | 9/2008 |
| JP | 4335487 B2 | 9/2009 |
| JP | 2010-500107 A | 1/2010 |
| JP | 2010-504174 A | 2/2010 |
| JP | 2010-517623 A | 5/2010 |
| JP | 2010-528761 A | 8/2010 |
| JP | 2010-188189 A | 9/2010 |
| JP | 2010-535075 A | 11/2010 |
| JP | 2010-536527 A | 12/2010 |
| JP | 2012-504031 A | 2/2012 |
| JP | 2012-152563 A | 8/2012 |
| JP | 2013-506439 A | 2/2013 |
| JP | 2013-543399 A | 12/2013 |
| JP | 2014-513585 A | 6/2014 |
| JP | 2014-517720 A | 7/2014 |
| JP | 2015-523168 A | 8/2015 |
| JP | 2016-501104 A | 1/2016 |
| JP | 2016-501115 A | 1/2016 |
| JP | 2016-509932 A | 4/2016 |
| JP | 2016-510645 A | 4/2016 |
| JP | 2016-512753 A | 5/2016 |
| JP | 2016-518948 A | 6/2016 |
| JP | 2017-527397 A | 9/2017 |
| JP | 2018-079352 A | 5/2018 |
| JP | 6392778 B2 | 9/2018 |
| JP | 6802300 B2 | 12/2020 |
| RU | 2124986 C1 | 1/1999 |
| RU | 2434604 C1 | 11/2011 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/02212 A1 | 2/1996 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/18333 A1 | 4/2000 |
| WO | 00/41649 A1 | 7/2000 |
| WO | 00/47271 A1 | 8/2000 |
| WO | 00/62716 A1 | 10/2000 |
| WO | 01/28453 A2 | 4/2001 |
| WO | 01/41679 A1 | 6/2001 |
| WO | 01/64278 A1 | 9/2001 |
| WO | 01/74272 A2 | 10/2001 |
| WO | 02/07795 A2 | 1/2002 |
| WO | 02/24118 A1 | 3/2002 |
| WO | 02/24119 A1 | 3/2002 |
| WO | 02/45933 A2 | 6/2002 |
| WO | 02/47468 A1 | 6/2002 |
| WO | 02/60506 A1 | 8/2002 |
| WO | 2002/100301 A1 | 12/2002 |
| WO | 03/03946 A1 | 1/2003 |
| WO | 03/07795 A2 | 1/2003 |
| WO | 03/47468 A1 | 6/2003 |
| WO | 03/90834 A2 | 11/2003 |
| WO | 2004/000375 A1 | 12/2003 |
| WO | 2005/084595 A1 | 9/2005 |
| WO | 2005/112827 A2 | 12/2005 |
| WO | 2006/019626 A2 | 2/2006 |
| WO | 2006/058322 A2 | 6/2006 |
| WO | 2006/108090 A2 | 10/2006 |
| WO | 2007/016251 A2 | 2/2007 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/052421 A1 | 5/2008 |
| WO | 2008/091589 A1 | 7/2008 |
| WO | 2008/021006 A3 | 8/2008 |
| WO | 2008/097589 A1 | 8/2008 |
| WO | 2008/097592 A2 | 8/2008 |
| WO | 2008/150529 A1 | 12/2008 |
| WO | 2009/017827 A1 | 2/2009 |
| WO | 2009/029199 A1 | 3/2009 |
| WO | 2009/045332 A2 | 4/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/037141 A1 | 4/2010 |
| WO | 2010/057262 A1 | 5/2010 |
| WO | 2010/086460 A1 | 8/2010 |
| WO | 2010/132707 A1 | 11/2010 |
| WO | 2010/150208 A2 | 12/2010 |
| WO | 2011/098565 A1 | 8/2011 |
| WO | 2011/109450 A2 | 9/2011 |
| WO | 2011/109801 A2 | 9/2011 |
| WO | 2011/112706 A2 | 9/2011 |
| WO | 2012/004460 A2 | 1/2012 |
| WO | 2012/011261 A1 | 1/2012 |
| WO | 2012/040643 A2 | 3/2012 |
| WO | 2012/047644 A2 | 4/2012 |
| WO | 2012/065080 A2 | 5/2012 |
| WO | 2012/082952 A2 | 6/2012 |
| WO | 2012/099979 A1 | 7/2012 |
| WO | 2012/110767 A2 | 8/2012 |
| WO | 2012/116368 A2 | 8/2012 |
| WO | 2012/135603 A2 | 10/2012 |
| WO | 2012/158944 A1 | 11/2012 |
| WO | 2012/167131 A1 | 12/2012 |
| WO | 2013/074663 A2 | 5/2013 |
| WO | 2013/074990 A1 | 5/2013 |
| WO | 2013/096854 A2 | 6/2013 |
| WO | 2013/109337 A1 | 7/2013 |
| WO | 2014/018189 A2 | 1/2014 |
| WO | 2014/018432 A2 | 1/2014 |
| WO | 2014/099150 A1 | 6/2014 |
| WO | 2014/099163 A1 | 6/2014 |
| WO | 2014/099722 A1 | 6/2014 |
| WO | 2014/144937 A2 | 9/2014 |
| WO | 2014/149319 A1 | 9/2014 |
| WO | 2014/181188 A2 | 11/2014 |
| WO | 2014210124 A1 | 12/2014 |
| WO | 2015/045002 A1 | 4/2015 |
| WO | 2015/085138 A1 | 6/2015 |
| WO | 2015/171743 A2 | 11/2015 |

(56) References Cited

FOREIGN PATENT DOCUMENTS

| WO | 2015/173794 | A1 | 11/2015 |
|---|---|---|---|
| WO | 2016/028591 | A1 | 2/2016 |
| WO | 2016/044223 | A1 | 3/2016 |
| WO | 2016/100913 | A1 | 6/2016 |
| WO | 2016172349 | A1 | 10/2016 |
| WO | 2016/186909 | A1 | 11/2016 |
| WO | 2017/038145 | A1 | 3/2017 |
| WO | 2017/096157 | A1 | 6/2017 |
| WO | 2017218375 | A1 | 12/2017 |
| WO | 2018029680 | A1 | 2/2018 |
| WO | 2019/067219 | A1 | 4/2019 |
| WO | 2019/067220 | A1 | 4/2019 |
| WO | 2019/074607 | A1 | 4/2019 |
| WO | 2019/074869 | A1 | 4/2019 |
| WO | 2019/089138 | A1 | 5/2019 |
| WO | 2019/246268 | A1 | 12/2019 |

OTHER PUBLICATIONS

Clough, Norman E. Introducing a New Family of GORE ePTFE Fibers (2007), pp. 1-10.

English translation of RU2434604 (C1), filed Apr. 30, 2010, translation powered by EPO and Google, 8 pages.

EPO Form 1002 for EP16196687.4 Filed Dec. 28, 2016.

Forward citations for E12 obtained from: https://scholar.google.com/scholar?cites=5981833429320176658&assdt=2005&sciodt=0,5&hl=en.

Google Image Search Results, "S-Shaped", accessed Nov. 1, 2013.

International Search Report and Written Opinion received for PCT Application No. PCT/US2020/020550, dated Jun. 9, 2020, 12 pages.

Mano Thubrikar, "The Aortic Valve", Chapter 1: Geometry of the Aortic Valve, CRC Press, Inc., Informa Healthcare, 2011, 40 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda FI, Okamoto Y, Yoshida M. Development of microporous self-expanding stent grafts for treating cerebral aneurysms: designing micropores to control intimal hyperplasia. J Artif Organs 2011; 14:348-356.

Norman E. Clough. Introducing a New Family of GORE (Trademark) ePTFE Fibers (2007).

Opposition from EP16196687.4, mailed on Dec. 12, 2019, 38 pages.

Opposition from EP17187595.8, filed Sep. 12, 2019, 50 pages.

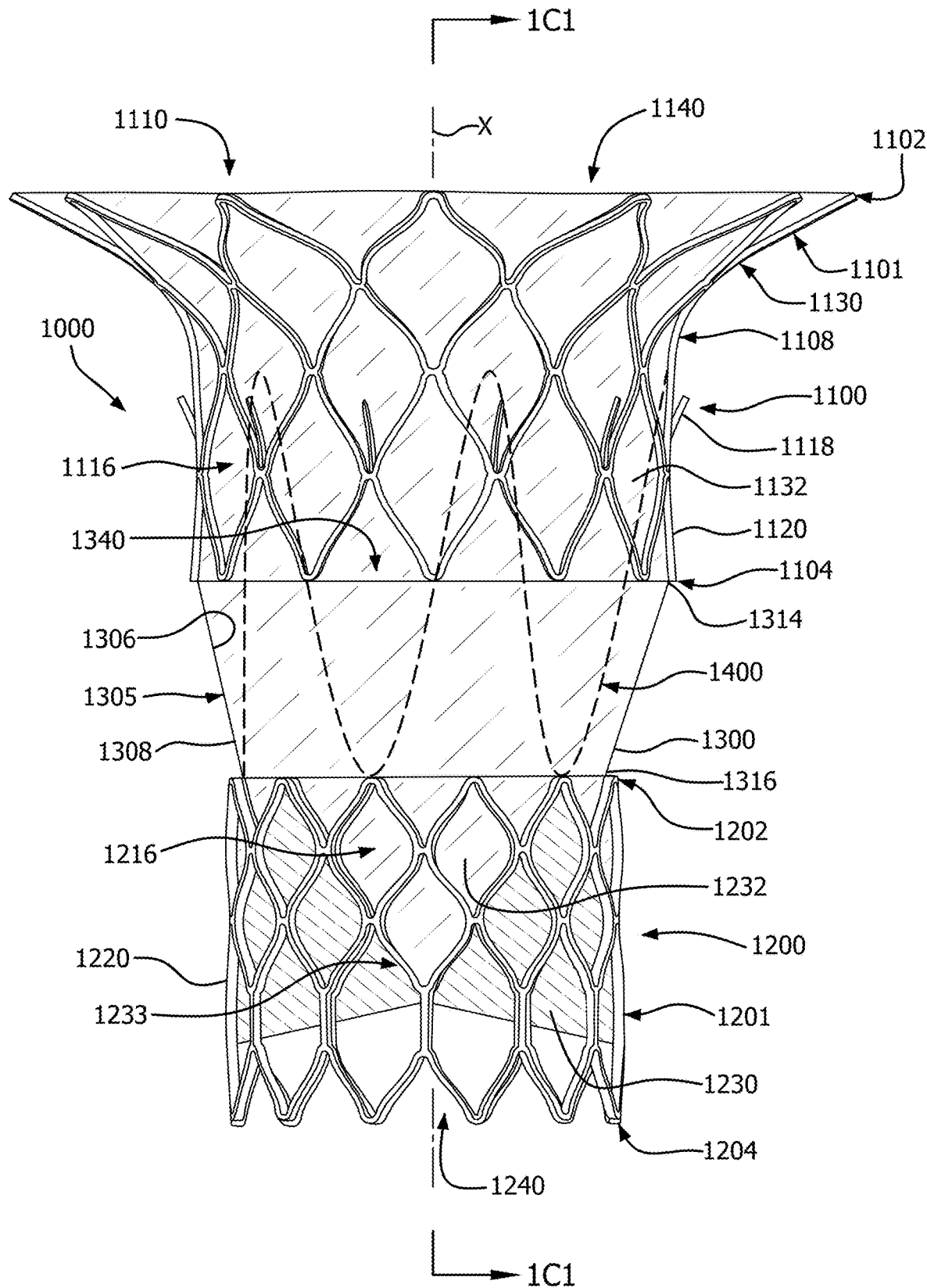
FIG. 1B1

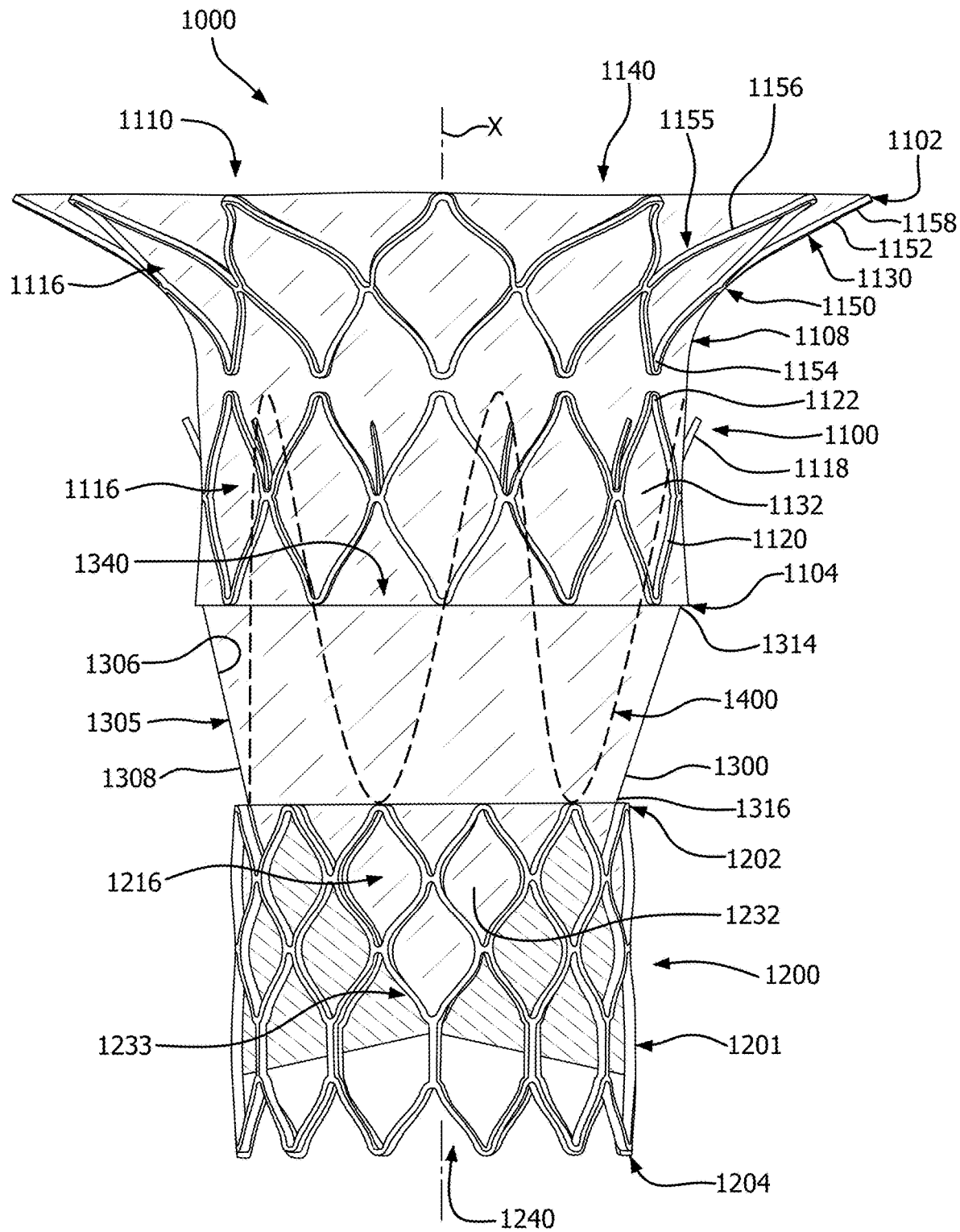
FIG. 1B2

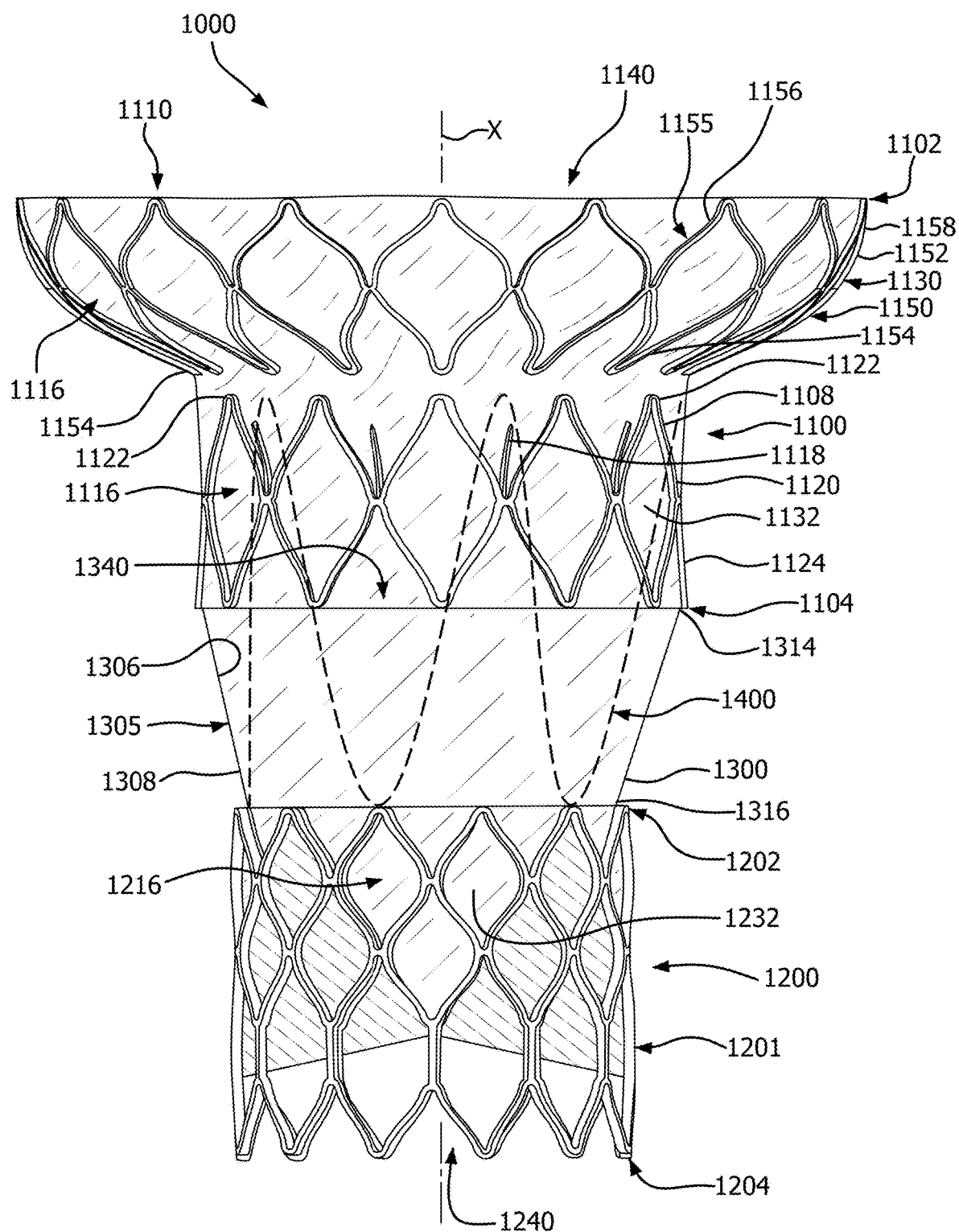
FIG. 1B3

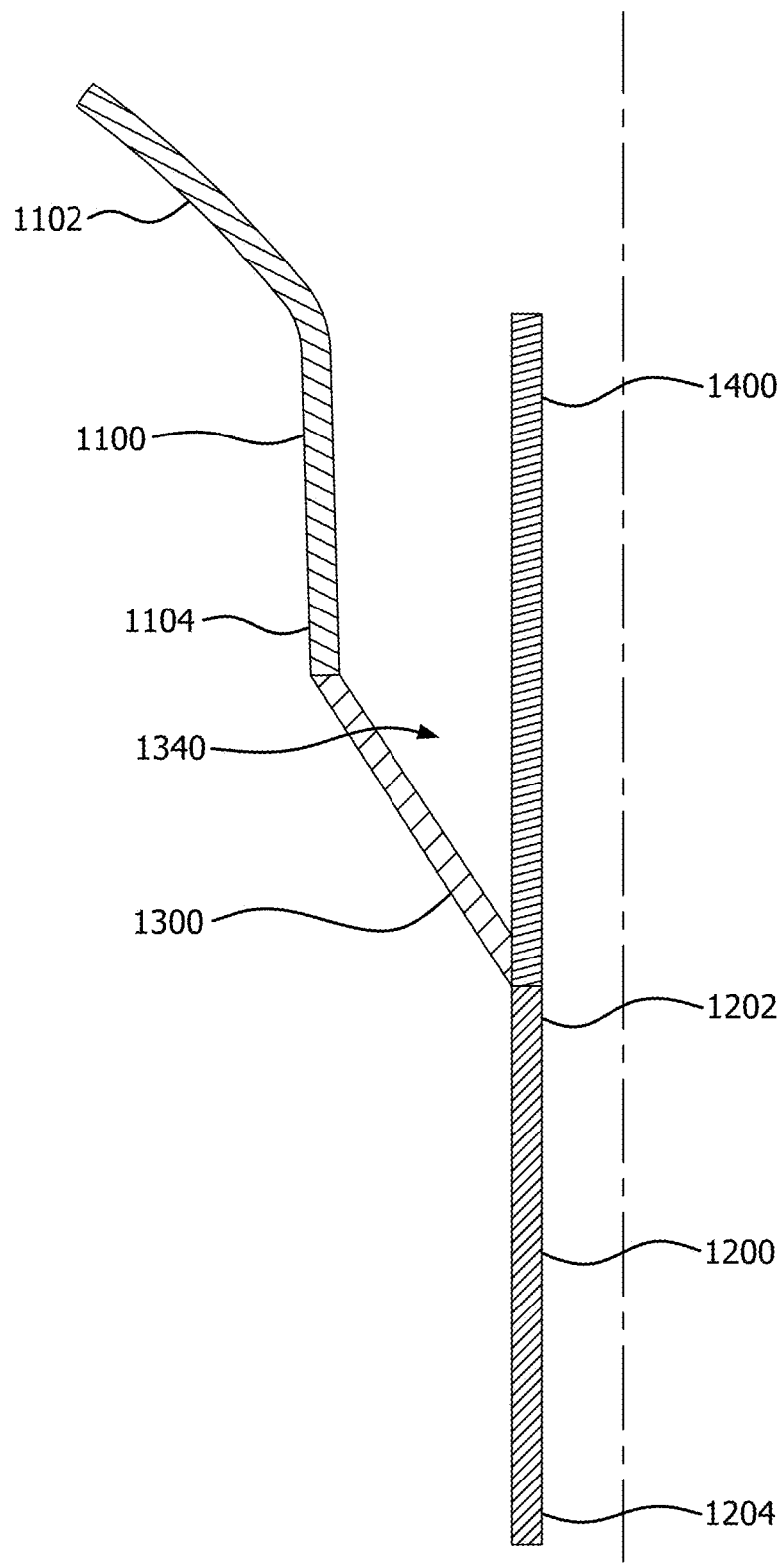
FIG. 1C1

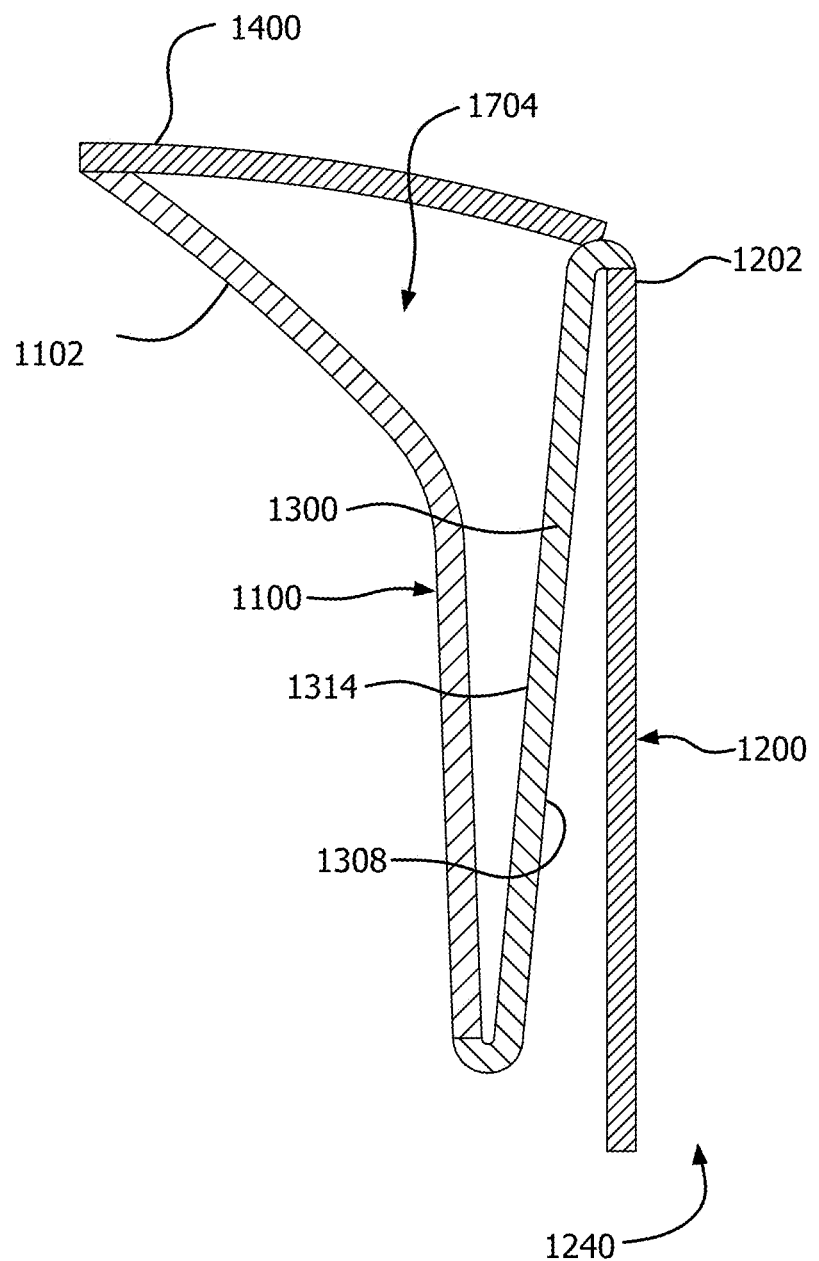
FIG. 1C2

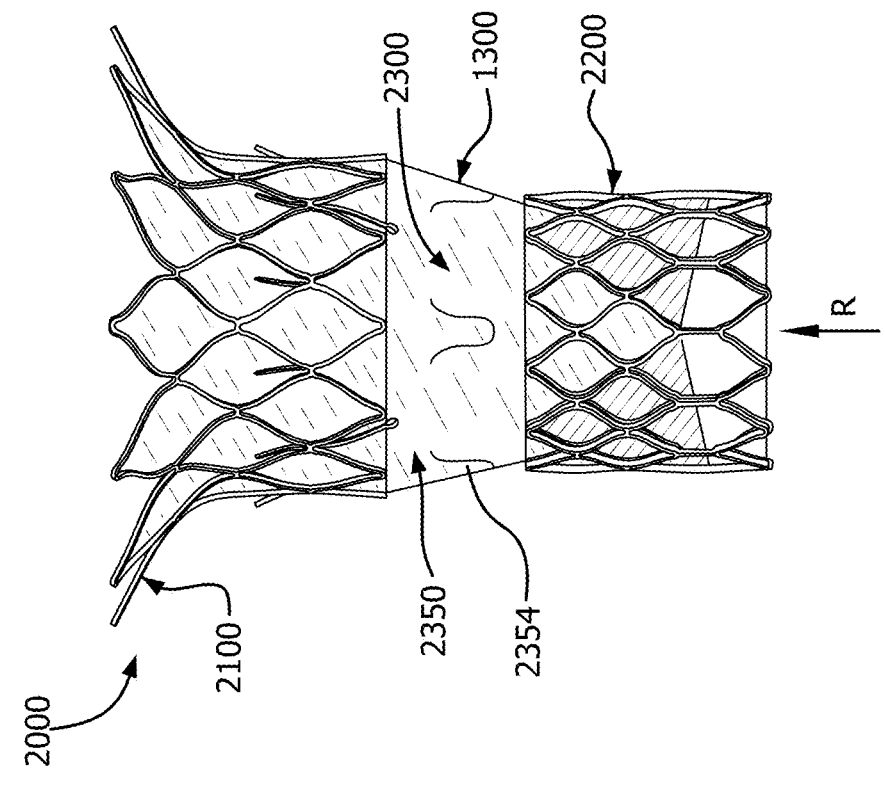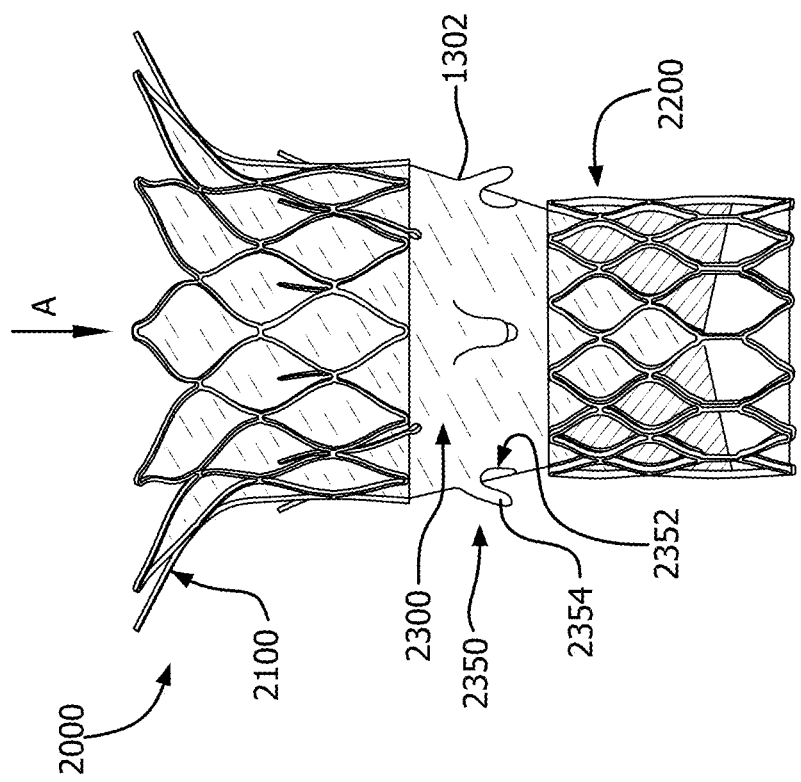
FIG. 5B
FIG. 5A

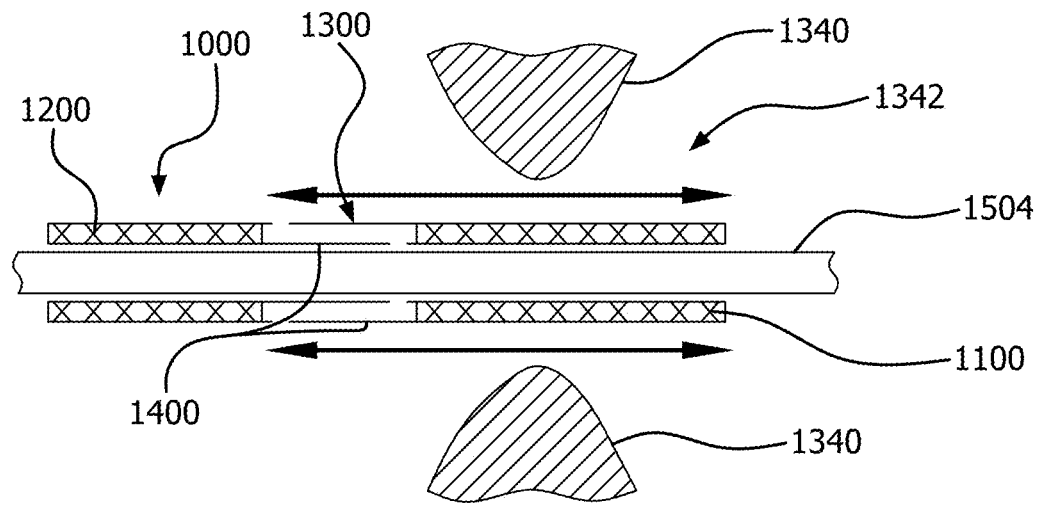
FIG. 6A
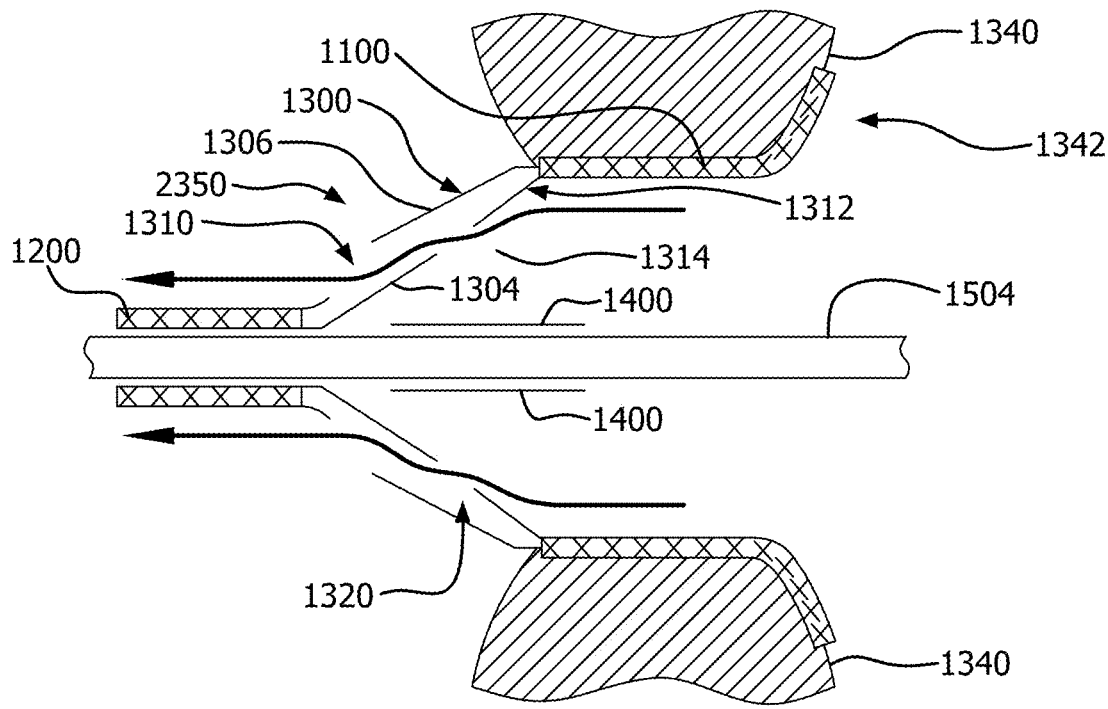
FIG. 6B1

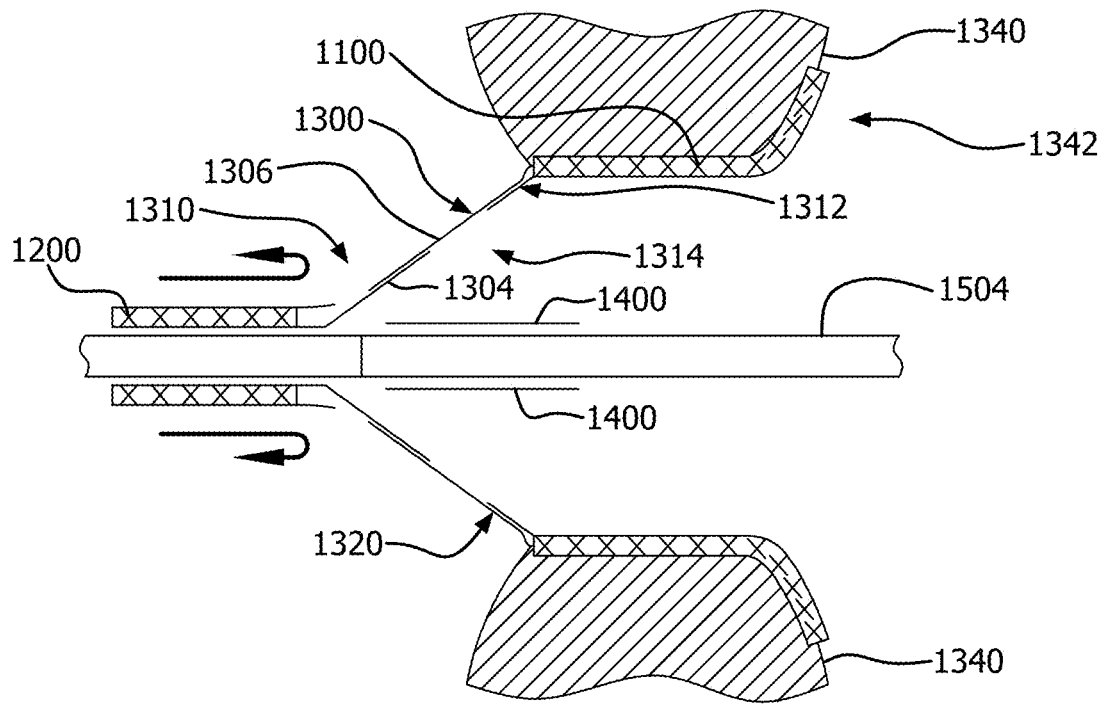
FIG. 6B2
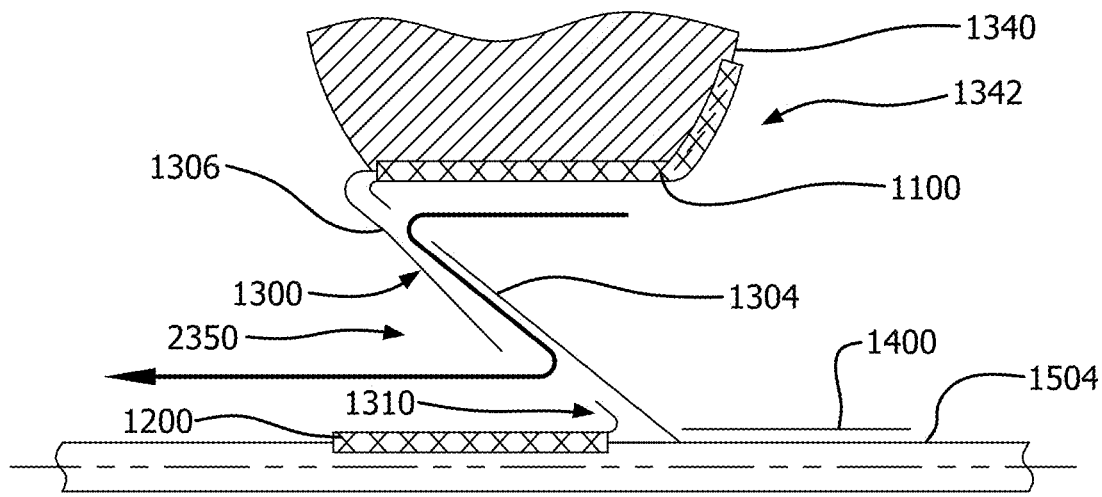
FIG. 6C1

FIG. 6C2

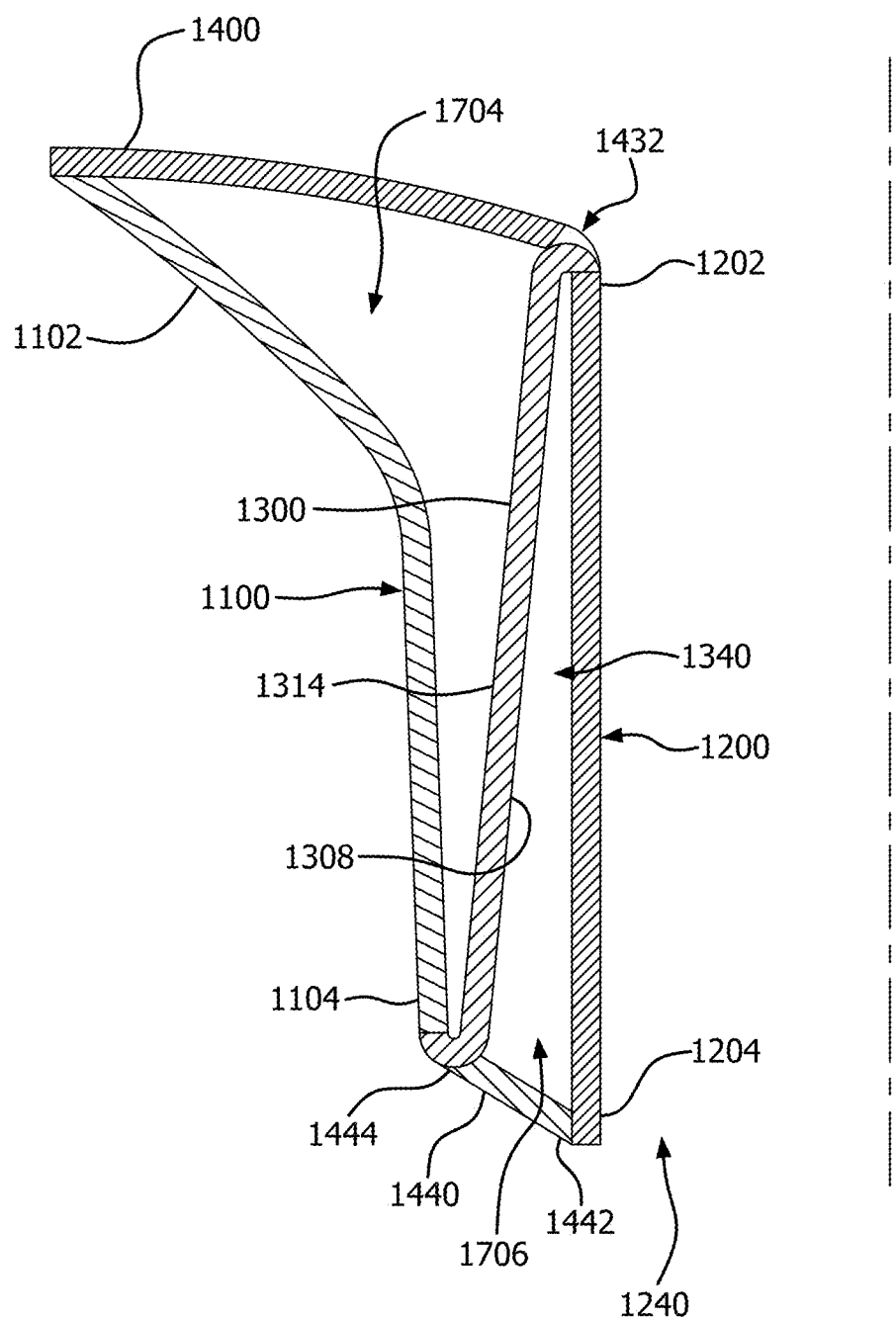
FIG. 7D1

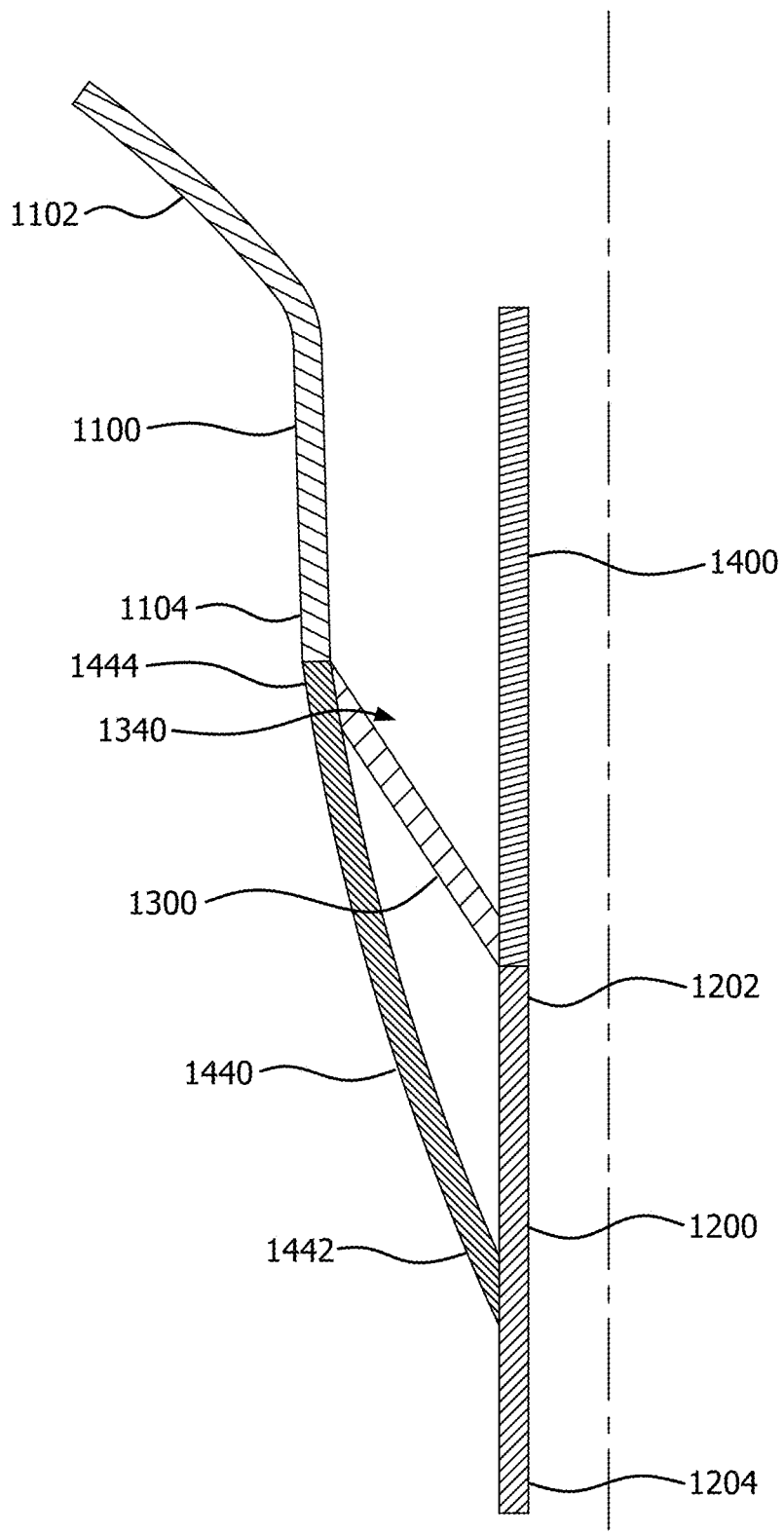
FIG. 7D2

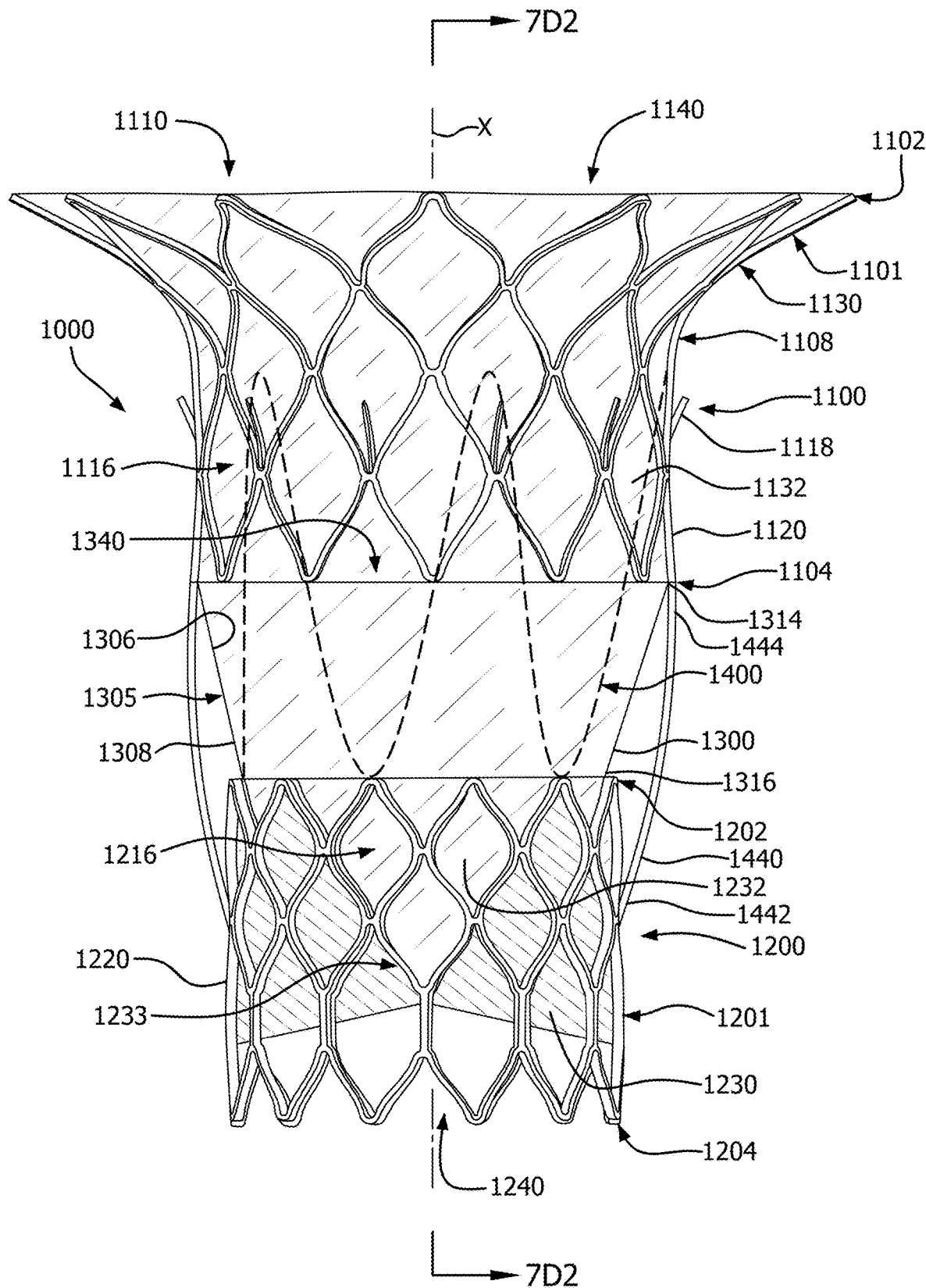
FIG. 7D3

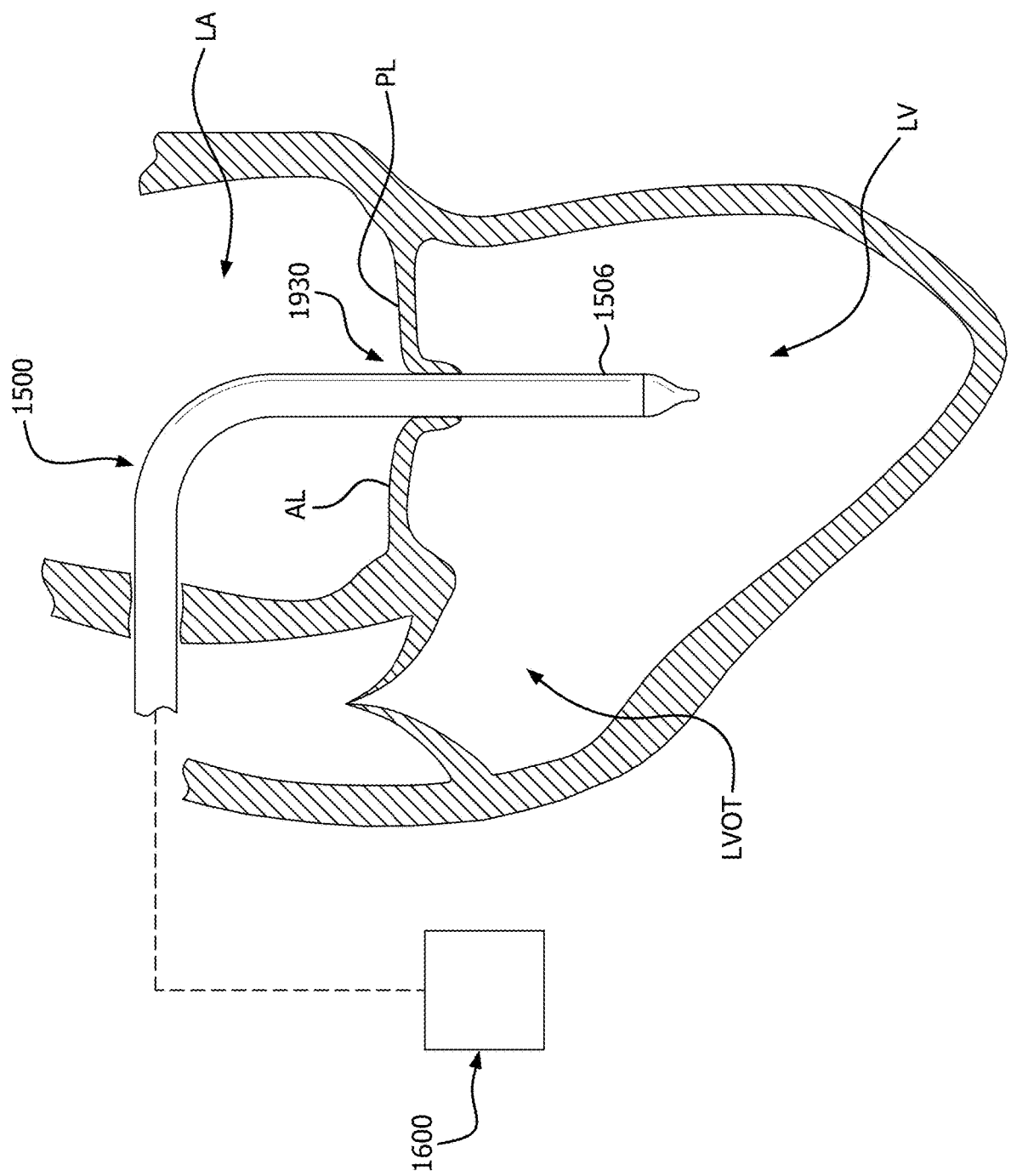

TELESCOPING PROSTHETIC VALVE WITH RETENTION ELEMENT

CROSS-REFERENCE TO RELATED APPLICATION

This application is a continuation of U.S. application Ser. No. 16/805,181, filed Feb. 28, 2020, which claims the benefit of Provisional Application No. 62/812,782, filed Mar. 1, 2019, and also claims the benefit of Provisional Application No. 62/833,086, filed Apr. 12, 2019, all of which are incorporated herein by reference in their entireties for all purposes.

FIELD

The present disclosure relates generally to prosthetic valves and more specifically to flexible leaflet-type prosthetic valve devices, systems and methods.

BACKGROUND

Bioprosthetic valves have been developed that attempt to mimic the function and performance of a native valve. Bioprosthetic valves may be formed from synthetic materials, natural tissue such as biological tissue, or a combination of synthetic materials and natural tissue.

Though many conventional designs require delivery to a target region within a patient's anatomy via open-heart surgical techniques, alternative approaches such as transcatheter techniques offer a number of advantages. Among other examples, a transcatheter prosthetic valve that is delivered endovascularly via a catheter can help to minimize patient trauma as compared with an open-heart, surgical procedure. Open-heart surgery involves extensive trauma to the patient, with attendant morbidity and extended recovery. On the other hand, a valve delivered to the recipient site via a catheter avoids the trauma of open-heart surgery and may be performed on patients too ill or feeble to survive the open-heart surgery.

However, challenges exist with accessing treatment regions within the anatomy, properly positioning the bioprosthesis for deployment, and depending on the particular anatomy being repaired or augmented, modifications of the surrounding anatomy may arise as a consequence of the presence of the bioprosthesis. In some instances, such consequential modifications to the surrounding anatomy may negatively impact a patient's health.

While multiple embodiments are disclosed, still other embodiments will become apparent to those skilled in the art from the following detailed description, which shows and describes illustrative examples. Accordingly, the drawings and detailed description are to be regarded as illustrative in nature and not restrictive.

SUMMARY

Various aspects relate to prosthetic valves transitional between a delivery configuration and a deployed, nested configuration in-situ.

Various aspects relate to a prosthetic valve including a leaflet frame subcomponent including a one-way valve, the leaflet frame subcomponent having a leaflet frame subcomponent inflow end and a leaflet frame subcomponent outflow end; an anchor frame subcomponent having an anchor frame subcomponent inflow end and an anchor frame subcomponent outflow end; a connecting sheath coupling the leaflet frame subcomponent to the anchor frame subcomponent; and a retention element coupled to the connecting sheath, the retention element being configured to retain the prosthetic valve in the deployed, nested configuration, wherein in the delivery configuration the leaflet frame subcomponent and the anchor frame subcomponent are longitudinally offset relative to one another with the connecting sheath being unfolded and uneverted and in the nested configuration the leaflet frame subcomponent is nested with the anchor frame subcomponent and the connecting sheath is folded and everted so as to lie between the leaflet frame subcomponent and the anchor frame subcomponent, such that the retention element extends from the leaflet frame subcomponent inflow end to the anchor frame subcomponent inflow end.

Various aspects also relate to a prosthetic valve configured to be retrieved, or a method of retrieving a prosthetic valve, in which an anchor frame subcomponent of the prosthetic valve has a predetermined flexibility such that the anchor frame subcomponent may be everted into an anchor frame subcomponent lumen such that the anchor frame subcomponent is operable to peel away from a tissue annulus and be drawn out of the anchor frame subcomponent lumen such that the prosthetic valve may be removed from the tissue annulus. In some implementations, a portion of the anchor frame subcomponent may pivot and compress about a location adjacent to an anchor frame subcomponent inflow end (e.g., at a flared portion), such that the anchor frame subcomponent may pivot or fold inwardly into the anchor frame subcomponent lumen and be drawn out of the anchor frame subcomponent lumen having been everted.

According to one example ("Example 1"), a prosthetic valve transitionable between a delivery configuration and a deployed, nested configuration in-situ, includes a leaflet frame subcomponent, an anchor frame subcomponent, a connecting sheath coupling the leaflet frame and anchor frame subcomponents, and a retention element coupled to the connecting sheath, wherein when the prosthetic valve is in the deployed, nested configuration, the connecting sheath is everted and the leaflet frame subcomponent is at least partially nested within an anchor frame subcomponent lumen, the retention element has translated within the anchor frame subcomponent lumen toward an anchor frame subcomponent inflow end, and the retention element is biased outwardly against the anchor frame subcomponent with an outward bias such that the retention element extends from a leaflet frame subcomponent inflow end to an anchor frame subcomponent inflow end.

Optionally, the leaflet frame subcomponent defines a tubular shape and has a leaflet frame subcomponent wall extending from the leaflet frame subcomponent inflow end and a leaflet frame subcomponent outflow end and the leaflet frame subcomponent defining a leaflet frame subcomponent lumen, the leaflet frame subcomponent including a one-way valve.

Optionally, the anchor frame subcomponent defines a tubular shape and has the anchor frame subcomponent inflow end and an anchor frame subcomponent outflow end, and the anchor frame subcomponent defines an anchor frame subcomponent lumen.

Optionally, the connecting sheath defines a tubular shape and has a connecting sheath inflow end coupled to the anchor frame subcomponent outflow end and a connecting sheath outflow end coupled to the leaflet frame subcomponent inflow end coupling the leaflet frame subcomponent to the anchor frame subcomponent, and the connecting sheath has a connecting sheath inner surface that defines a connecting sheath lumen.

Optionally, the retention element has a retention element first end and a retention element second end, the retention element second end being coupled to the connecting sheath outflow end.

Optionally, when the prosthetic valve is in the delivery configuration, the leaflet frame subcomponent and the anchor frame subcomponent are longitudinally offset from one another such that the leaflet frame subcomponent inflow end is situated distal of the anchor frame subcomponent outflow end, wherein the retention element resides within the connecting sheath lumen and extends away from the leaflet frame subcomponent inflow end and substantially parallel with a longitudinal axis of the leaflet frame subcomponent and adjacent to the connecting sheath.

Optionally, when the prosthetic valve is in the deployed, nested configuration, the anchor frame subcomponent inflow end flares or tapers radially outward.

According to another example ("Example 2") further to Example 1, wherein the prosthetic valve is transitionable between the delivery configuration and the deployed, nested configuration via an expanded pre-deployed, un-nested configuration.

According to another example ("Example 3") further to Example 2, the retention element is pivotable about the retention element second end upon translation of the retention element translated within the anchor frame subcomponent lumen towards the anchor frame subcomponent inflow end, such that the retention element extends from the leaflet frame subcomponent inflow end to the anchor frame subcomponent inflow end.

According to another example ("Example 4") further to any one of Examples 1 to 3, the leaflet frame subcomponent includes a leaflet frame defining a leaflet frame wall, one or more leaflets, and leaflet frame cover, the leaflet frame is generally tubular shaped defining a leaflet frame inflow end and a leaflet frame outflow end with a leaflet frame lumen therethrough.

According to another example ("Example 5") further to Example 4, the leaflet frame wall of the leaflet frame is at least partially covered with the leaflet frame cover configured to restrict fluid from passing through the covered portion of the leaflet frame wall.

According to another example ("Example 6") further to Example 4 or 5, the one or more leaflets are operable to open to allow flow from the leaflet frame subcomponent inflow end and to pass through the leaflet frame subcomponent outflow end in antegrade flow conditions, and are operable to close to restrict flow from flowing from the leaflet frame subcomponent outflow end through the leaflet frame subcomponent inflow end in retrograde flow conditions.

According to another example ("Example 7") further to any one of Examples 4 to 6, the retention element second end is not directly coupled to the leaflet frame at the leaflet frame subcomponent inflow end, there being a portion of the connecting sheath therebetween.

According to another example ("Example 8") further to any one of Examples 4 to 7, the leaflets comprise a composite material including a porous synthetic fluoropolymer membrane defining pores and an elastomer or elastomeric material filling the pores, and optionally TFE-PMVE copolymer comprising from about 27 to about 32 weight percent perfluoromethyl vinyl ether and respectively from about 73 to about 68 weight percent tetrafluoroethylene on at least a portion of the composite material, and optionally, wherein the elastomer or elastomeric material comprises a TFE-PMVE copolymer, and optionally wherein the porous synthetic fluoropolymer membrane is ePTFE.

According to another example ("Example 9") further to any one of the preceding Examples, the anchor frame subcomponent includes an anchor frame and an anchor frame cover, the anchor frame defines a generally tubular shape extending between the anchor frame subcomponent inflow end and the anchor frame subcomponent outflow end, an anchor frame inner surface and an anchor frame outer surface defining an anchor frame wall, the anchor frame is at least partially covered with the anchor frame cover to restrict fluid from passing through the anchor frame wall.

According to another example ("Example 10") further to Example 9, the prosthetic valve is in the deployed, nested configuration, the anchor frame defines a flared portion at the anchor frame subcomponent inflow end that flares or tapers radially outward.

According to another example ("Example 11") further to Example 9 or 10, when Example 9 or 10 is further to any one of Examples 4 to 8, the connecting sheath is contiguous with the anchor frame cover and the leaflet frame cover.

According to another example ("Example 12") further to any one of Examples 9 to 11, when any one of Examples 9 to 11 is further to any one of Examples 4 to 8, the retention element is coupled to the connecting sheath between, but not directly coupled to, the leaflet frame or the anchor frame such that the retention element is operable to maintain the nested configuration of the anchor frame subcomponent and the leaflet frame subcomponent.

According to another example ("Example 13") further to any preceding Example, the prosthetic valve has a smaller diameter in the delivery configuration than in the deployed, nested configuration.

According to another example ("Example 14") further to any preceding Example, the anchor frame subcomponent has an anchor frame subcomponent inner surface, wherein, in the deployed, nested configuration, the anchor frame subcomponent inner surface has a diameter at least slightly larger than a leaflet frame subcomponent outer surface of the leaflet frame subcomponent and the leaflet frame subcomponent is nested within the anchor frame subcomponent.

According to another example ("Example 15") further to Example 2 or further to any one of Examples 3 to 14 further to Example 2, the connecting sheath is a thin-walled flexible tubular member having a connecting sheath inner surface that defines a connecting sheath lumen in fluid communication with the anchor frame subcomponent lumen and the leaflet frame subcomponent lumen, and wherein the connecting sheath is operable to fold and evert when the leaflet frame subcomponent is advanced from the pre-deployed, un-nested configuration to the deployed, nested configuration so as to lie between the leaflet frame subcomponent and the anchor frame subcomponent.

According to another example ("Example 16") further to any preceding Example, the connecting sheath comprises flow enabling features in a wall of the connecting sheath, the wall extending between the connecting sheath inflow end and the connecting sheath outflow end, wherein the flow enabling features are operable to allow antegrade fluid flow through the connecting sheath wall and restrict retrograde flow through the connecting sheath wall when the leaflet frame subassembly is not in the deployed, nested configuration.

According to another example ("Example 17") further to any one of Examples 1 to 15, the connecting sheath comprises an inner film layer and an outer film layer, the inner film layer and the outer film layer being coupled together at least at the leaflet frame subcomponent inflow end and the anchor frame subcomponent outflow end, the inner film layer defining at least one inner aperture therethrough adjacent the anchor frame subcomponent outflow end and the outer film layer defines at least one outer aperture therethrough adjacent the leaflet frame subcomponent, the inner film layer and the outer film layer being not coupled at least between one of the inner apertures and one of the outer apertures so as to define a flow space therebetween operable to permit antegrade blood flow and restrict retrograde flow therethrough when the leaflet frame subcomponent is not in the deployed, nested configuration in the anchor frame subcomponent, and is operable to restrict antegrade and retrograde flow when the leaflet frame subcomponent is in the deployed, nested configuration within the anchor frame subcomponent.

According to another example ("Example 18") further to any one of Examples 1 to 15, the connecting sheath comprises an inner film layer and an outer film layer, the inner film layer and the outer film layer being coupled together at least at the anchor frame subcomponent outflow end, the inner film layer defining at least one inner aperture therethrough adjacent the anchor frame subcomponent outflow end, the inner film layer and the outer film layer being not coupled at least downstream of the inner apertures so as to define a flow space therebetween operable to permit antegrade blood flow with the inner film layer separating from the outer film layer at the inner aperture and so as to restrict retrograde flow therethrough with the inner film layer coming together and covering the inner aperture when the leaflet frame subcomponent is not in the deployed, nested configuration in the anchor frame subcomponent, and is operable to restrict antegrade and retrograde flow when the leaflet frame subcomponent is in the deployed, nested configuration within the anchor frame subcomponent.

According to another example ("Example 19") further to any preceding Example, when the prosthetic valve is in the deployed, nested configuration, the retention element is configured to cover an inflow annular groove formed between the anchor frame subcomponent, the everted connecting sheath, and the leaflet frame subcomponent.

According to another example ("Example 20") further to any preceding Example, the retention element further includes a non-permeable cover and wherein, when the prosthetic valve is in the deployed, nested configuration, an inflow annular groove is defined by the anchor frame subcomponent, the connecting sheath, and the leaflet frame subcomponent at an inflow end of the prosthetic valve, and wherein the retention element, including the non-permeable cover, is operable to cover and restrict fluid flow into an inflow annular groove.

According to another example ("Example 21") further to Example 2 or further to any one of Examples 3 to 20 further to Example 2, the retention element is an elongated element that is operable to extend generally parallel to a central, longitudinal axis X of the prosthetic valve when in the pre-deployed configuration, and operable to extend at an angle to the central, longitudinal axis X when in the deployed configuration.

According to another example ("Example 22") further to any preceding Example, the retention element is operable to translate through the anchor frame subcomponent during transition of the prosthetic valve between the delivery configuration and the deployed, nested configuration and the connecting sheath is operable to fold and evert within the anchor frame subcomponent lumen and lie between the leaflet frame subcomponent and the anchor frame subcomponent during transition of the prosthetic valve between the delivery configuration and the deployed, nested configuration.

According to another example ("Example 23") further to any preceding Example, the retention element comprises a continuous sinuous element configured to have an outward spring bias toward a planar star-shaped configuration defining elongated elements bending about apices, the elongated elements have an elongated element first end and an elongated element second end, when in the star-shaped configuration the elongated elements extend radially with the elongated element first ends and respective apices defining an inner circumference at a retention element first end and the elongated element second ends and respective apices defining an outer circumference at a retention element second end, the sinuous element is operable to be elastically restrained to a tubular configuration wherein the elongated elements are rotated about the apices at the elongated element first ends such that the elongated element second ends are rotated toward each other to define a tubular or conical configuration, with the sinuous element defining a first tubular diameter wherein the elongated elements extend laterally to the central, longitudinal axis X and along the connecting sheath and lateral with the anchor frame subcomponent and leaflet frame subcomponent.

According to another example ("Example 24") further to Example 23 further to Example 20, the non-permeable cover extends from the apices at the elongated element first ends of the elongated elements to the apices at the elongated element second ends, wherein when the prosthetic valve is in the deployed, nested configuration, the non-permeable cover extends from the leaflet frame subcomponent inflow end to the anchor frame subcomponent inflow end covering the inflow annular groove formed between the anchor frame subcomponent, the connecting sheath and the leaflet frame subcomponent.

According to another example ("Example 25") further to Example 23 or 24, further comprising a tether element coupled to the retention element, operable to be pulled by an operator to affect advancement of the retention element through the anchor frame subcomponent, the retention element second end of the retention element being held in a compressed state by a predetermined amount of tension on the tether element, wherein the tension of the tether element may be released and thus release the elongated element second end of the retention element so as to allow expansion and deployment of the retention element.

According to another example ("Example 26") further to any preceding Example, the retention element is biased towards a planar position and operable to retain the relative position of the leaflet frame subcomponent and the anchor frame subcomponent by virtue of the outward bias.

According to another example ("Example 27") further to any preceding Example, one or more apices at the retention element second end of the retention element may abut and slide along the connecting sheath inner surface and subsequently the anchor frame subcomponent inner surface while expanding under the outward bias until the apices at the retention element second end are fully expanded about the anchor frame subcomponent inflow end, wherein the outward bias produces sufficient force to advance the retention element through the connecting sheath and the anchor frame subcomponent inner surface toward the anchor frame subcomponent inflow end while pulling the leaflet frame subcomponent into the anchor frame subcomponent.

According to another example ("Example 28") further to any preceding Example, a length of the anchor frame subcomponent varies along its circumference wherein the anchor frame subcomponent outflow end has a tapered geometry operable such that, when the prosthetic valve is placed in a mitral valve annulus, the anchor frame subcomponent outflow end may extend further into a left ventricle adjacent to a posterior side of the left ventricle and extends less into a LVOT on an anterior side of the left ventricle.

According to another example ("Example 29") further to any preceding Example, a hoop strength of the anchor frame subcomponent is variable along a length and/or a circumference of the anchor frame subcomponent and is predetermined to have a greater stiffness at a smaller tapered portion of an anchor frame subcomponent anterior portion of the anchor frame subcomponent outflow end, to substantially match a stiffness of an aortomitral junction, whereas the stiffness may be relatively less at a longer prosthetic valve posterior portion adjacent a posterior side of the left ventricle.

According to another example ("Example 30") further to any preceding Example, the anchor frame subcomponent has a predetermined flexibility such that the anchor frame subcomponent may be everted into the anchor frame subcomponent lumen such that the anchor frame subcomponent is operable to peel away from a tissue annulus and be drawn out of the anchor frame subcomponent lumen such that the prosthetic valve may be removed from the tissue annulus.

According to another example ("Example 31") further to any preceding Example, the anchor frame subcomponent includes one or more tissue engagement features that project away from an anchor frame outer surface of the anchor frame subcomponent and are operable to engage a tissue annulus.

According to another example ("Example 32") further to any preceding Example, the prosthetic valve further comprises an outflow annular groove cover extending from the anchor frame subcomponent outflow end and the leaflet frame subcomponent outflow end.

According to another example ("Example 33") further to Example 32, the outflow annular groove cover is configured to be blood permeable under physiologic conditions prior to the prosthetic valve being transitioned to the deployed, nested configuration.

According to another example ("Example 34") further to Examples 32 or 33, the outflow annular groove cover is configured to be less permeable to blood under physiologic conditions when the prosthetic valve is in the deployed, nested configuration than when the prosthetic valve is not in the deployed, nested configuration.

Disclosed herein are also methods of replacing a native valve of a patient's anatomy. According to one example ("Example 35"), the method includes providing a prosthetic valve including, an anchor frame subcomponent; a leaflet frame subcomponent nestable within the anchor frame subcomponent; a connecting sheath coupled to the leaflet frame subcomponent and the anchor frame subcomponent, the anchor frame subcomponent comprising an anchor frame subcomponent inflow end and anchor frame subcomponent outflow end; and a retention element coupled to the connecting sheath adjacent the leaflet frame subcomponent inflow end. The prosthetic valve is advanced in a delivery configuration to a treatment site within a patient's anatomy, wherein in the delivery configuration the leaflet frame subcomponent and the anchor frame subcomponent are longitudinally offset from one another such that a leaflet frame subcomponent inflow end of the leaflet frame subcomponent is situated distal of an anchor frame subcomponent inflow end. The anchor frame subcomponent is deployed within a tissue annulus. The leaflet frame subcomponent is nested within the anchor frame subcomponent by changing a relative position between the leaflet frame subcomponent and the anchor frame subcomponent. The retention element is deployed to extend from the leaflet frame subcomponent inflow end to the anchor frame subcomponent inflow end.

According to another example ("Example 36") further to Example 35, the method further comprises deploying the prosthetic valve at the treatment site.

According to another example ("Example 37") further to Examples 35 or 36, the leaflet frame subcomponent is nested within the anchor frame subcomponent after the prosthetic valve is deployed at the treatment site.

According to another example ("Example 38") further to any one of Example 35 to 37, the prosthetic valve is advanced to the treatment site via a catheter.

According to another example ("Example 39") further to any one of Examples 35 to 38, nesting the leaflet frame subcomponent within the anchor frame subcomponent includes drawing the leaflet frame subcomponent proximally relative to the anchor frame subcomponent.

According to another example ("Example 40") further to any one of Examples 35 to 39, the method further comprises securing the prosthetic valve to a valve orifice of the native valve such that the prosthetic valve is operable to transition between an open position wherein fluid flow is permitted, and a closed position wherein fluid flow is obstructed.

According to another example ("Example 41") further to any one of Examples 35 to 40, deploying the anchor frame within a tissue annulus includes releasing constraining elements to expand the anchor frame to a larger diameter of the tissue annulus.

According to another example ("Example 42") further to any one of Examples 35 to 39 and 41, deploying the anchor frame within a tissue annulus includes tightening the constraining elements to recompress the anchor frame to a smaller diameter to allow for repositioning of the prosthetic valve.

According to another example ("Example 43") further to any one of Examples 35 to 42, deploying the anchor frame within a tissue annulus includes tightening the constraining elements to recompress the anchor frame to a smaller diameter to allow for repositioning of the prosthetic valve.

Further disclosed herein is a method of treating a failing or dysfunctional native heart valve with a prosthetic valve. According to one example ("Example 44"), the method includes replacing the native valve with a prosthetic valve in accordance with any of Examples 1 to 34.

The foregoing Examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

FIG. 1B1 is a side view of the prosthetic valve of FIG. 1A in an expanded pre-deployed configuration;

FIG. 1B2 is a side view of a prosthetic valve in an expanded pre-deployed configuration, according to some embodiments FIG. 1B3 is a side view of a prosthetic valve in an expanded pre-deployed configuration, according to some embodiments;

FIG. 1C1 a side cross-sectional view along cut line 1C2 of the prosthetic valve of FIG. 1B1 in an expanded pre-deployed configuration;

FIG. 1C2 is a side cross-sectional view along cut line 1C2 of the prosthetic valve of FIG. 1B1 in a deployed configuration as shown in FIG. 7C;

FIG. 5A is a side view of the prosthetic valve with flow enabling features in an open configuration, according to some embodiments;

FIG. 5B is a side view of the prosthetic valve with the flow enabling features of FIG. 5A in a closed configuration;

FIG. 6A is a cross-sectional view of a simplified representation of the prosthetic valve being constrained onto a delivery catheter and placed within a tissue annulus, in accordance with an embodiment;

FIG. 6B1 is a simplified representation cross-sectional view of the prosthetic valve being partially deployed from a delivery catheter within a tissue annulus showing antegrade flow, in accordance with the embodiment of FIG. 6A;

FIG. 6B2 is a simplified representation cross-sectional view of the prosthetic valve partially deployed within a tissue annulus showing retrograde flow, in accordance with the embodiment of FIG. 6A;

FIG. 6C1 is a simplified representation cross-sectional view of the prosthetic valve deployed within a native valve orifice showing antegrade flow, in accordance with the embodiment of FIG. 6A FIG. 6C2 is a simplified representation cross-sectional view of the prosthetic valve deployed within a native valve orifice showing retrograde flow, in accordance with the embodiment of FIG. 6A

FIG. 7D1 is a side cross-sectional view along cut line 7D2 of the prosthetic valve of FIG. 7D3 in a deployed configuration, such as shown in FIG. 7C by way of example;

FIG. 7D2 is a side cross-sectional view along cut line 7D2 of the prosthetic valve of FIG. 7D3 in an expanded pre-deployed configuration;

FIG. 7D3 is a side view of an embodiment of a prosthetic valve in an expanded pre-deployed configuration;

FIG. 9C1 is a highly simplified side partial cross-sectional representation of the prosthetic valve in a partially compressed partially deconstructed configuration with the anchor frame everting upon itself, illustrating an exemplary prosthetic valve retrieval procedure, according to some embodiments;

FIG. 9C2 is a highly simplified side partial cross-sectional representation of the prosthetic valve of FIG. 9A in a partially compressed partially deconstructed configuration with the anchor frame pivoting and compressing to an everted configuration, illustrating an exemplary prosthetic valve retrieval procedure, according to some embodiments.

FIG. 10B is a partial cross-sectional view of a prosthetic valve being positioned into a mitral valve tissue annulus illustrating an exemplary delivery procedure, according to some embodiments;

DETAILED DESCRIPTION

Definitions and Terminology

Figure 1A:
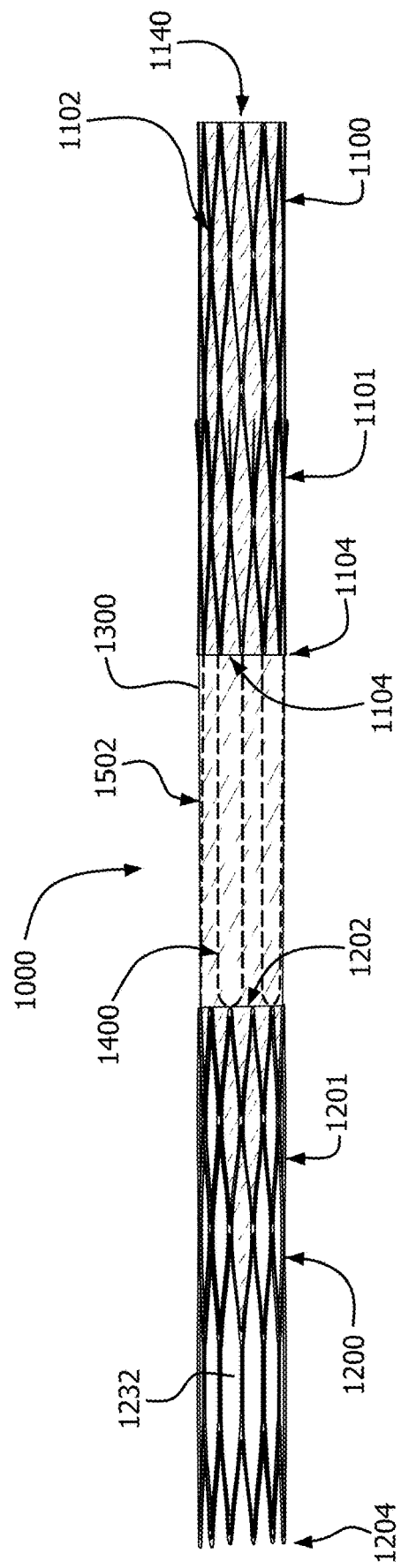
FIG. 1A is a side view of a prosthetic valve in a compressed pre-deployed configuration, according to some embodiments.

This disclosure is not meant to be read in a restrictive manner. For example, the terminology used in the application should be read broadly in the context of the meaning those in the field would attribute such terminology.

Persons skilled in the art will readily appreciate that various aspects of the present disclosure can be realized by any number of methods and apparatus configured to perform the intended functions. Stated differently, other methods and apparatus can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Certain relative terminology is used to indicate the relative position of components and features. For example, words such as "top", "bottom", "upper," "lower," "left," "right," "horizontal," "vertical," "upward," and "downward" are used in a relational sense (e.g., how components or features are positioned relative to one another) and not in an absolute sense unless context dictates otherwise. Similarly, throughout this disclosure, where a process or method is shown or described, the method may be performed in any order or simultaneously, unless it is clear from the context that the method depends on certain actions being performed first.

With respect to terminology of inexactitude, the terms "about" and "approximately" may be used, in certain instances, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error, differences in measurement and/or manufacturing equipment calibration, human error in reading and/or setting measurements, minor adjustments made to optimize performance and/or structural parameters in view of differences in measurements associated with other components, particular implementation scenarios, imprecise adjustment and/or manipulation of objects by a person or machine, and/or the like, for example.

As used herein, "couple" means join, connect, attach, adhere, affix, or bond, whether directly or indirectly, and whether permanently or temporarily.

The term "membrane" as used herein refers to a sheet of material comprising a single composition, such as, but not limited to, expanded fluoropolymer.

The term "composite material" as used herein refers to a material including two or more material components with one or more different material properties from the other. In some examples, a composite material includes at least a first material component in the form of a membrane and a second material component in the form of a polymer that is combined with the membrane (e.g., by coating and/or imbibing processes).

The term "laminate" as used herein refers to multiple layers of membrane, composite material, or other materials, such as, but not limited to a polymer, such as, but not limited to an elastomer, elastomeric or non-elastomeric material, and combinations thereof.

As used herein, the term "elastomer" refers to a polymer or a mixture of polymers that has the ability to be stretched to at least 1.3 times its original length and to retract rapidly to approximately its original length when released.

The term "elastomeric material" as used herein refers to a polymer or a mixture of polymers that displays stretch and recovery properties similar to an elastomer, although not necessarily to the same degree of stretch and/or recovery.

The term "non-elastomeric material" refers to a polymer or a mixture of polymers that displays stretch and recovery properties not similar to either an elastomer or elastomeric material, that is, considered not an elastomer or elastomeric material as is generally known.

The term "film" as used herein generically refers to one or more of the membrane, composite material, or laminate.

The term "biocompatible material" as used herein generically refers to any material with biocompatible characteristics including synthetic materials, such as, but not limited to, a biocompatible polymer, or a biological material, such as, but not limited to, bovine pericardium. Biocompatible material may comprise a first film and a second film as described herein for various embodiments.

The terms "native valve orifice" and "tissue orifice" as used herein refer to an anatomical structure into which a prosthetic valve can be placed. Such anatomical structure includes, but is not limited to, a location wherein a cardiac valve may or may not have been surgically removed. It is understood that other anatomical structures that can receive a prosthetic valve include, but are not limited to, veins, arteries, ducts and shunts. It is further understood that a valve tissue orifice or implant site may also refer to a location in a synthetic or biological conduit that may receive a valve.

The term "frame" as used herein generically refers to any structure or support used to directly or indirectly support leaflets for use in a prosthetic valve. It will be understood that, where appropriate, that the term frame may be used interchangeably with support structure. In accordance with some embodiments, the leaflets may be supported by the wall of a solid-walled conduit, the solid-walled conduit being understood to be a frame or support structure.

DESCRIPTION OF VARIOUS EMBODIMENTS

As will be described further below, in various examples, the prosthetic valve provides a leaflet frame subcomponent that does not directly couple with a tissue annulus and essentially floats within an anchor frame subcomponent coupled together by a connecting sheath and supported by a retention element. In various examples, the leaflet frame subcomponent, anchor frame subcomponent, and the connecting sheath are all tubular members, although non-tubular configurations for one or more of the foregoing are contemplated. It is understood that "tubular" as used herein includes tubes having a constant diameter along the length of the tube, and tubes having a variable diameter along the length of the tube, such as, but not limited to, a taper and an irregular circumference. For example, a tubular member may have a variable diameter along its length in at least one configuration of the tubular member. For example, a tubular member may have a generally constant diameter in a delivery configuration, and a variable diameter in a deployed or pre-deployed configuration. The anchor frame subcomponent may conform to the shape of the tissue annulus whereas the leaflet frame subcomponent does not necessarily conform to the shape of the tissue annulus. The leaflet frame subcomponent may remain a right circular hollow cylinder or at a preferred geometrical configuration so as to present the leaflets with a geometrically stable platform ensuring proper leaflet function, including opening and closing dynamics and coaptation in the case of flexible leaflets.

In various embodiments, the retention element is operable to retain relative positioning of the leaflet frame subcomponent within the anchor frame subcomponent. The retention element is operable to translate within the lumen of the anchor frame subcomponent to adjacent the anchor frame subcomponent inflow end. The retention element hinges about the retention element second end from a compressed configuration to a deployed configuration such that the retention element is positioned substantially perpendicular to the longitudinal axis of the leaflet frame subcomponent with the retention element first end adjacent to the anchor frame subcomponent inflow end and the retention element second end adjacent to the leaflet frame subcomponent inflow end.

In various embodiments, the retention element further includes a non-permeable cover that is operable to cover an inflow annular groove defined by the anchor frame subcomponent and the connecting sheath at an inflow end of the prosthetic valve. In the retention element deployed configuration the retention element extends between the leaflet frame subcomponent inflow end and the anchor frame subcomponent inflow end with the retention element including the cover operable to cover and restrict fluid flow into the inflow annular groove.

In various embodiments, the anchor frame subcomponent has a variable length about a circumference such that the anchor frame subcomponent outflow end defines a tapered profile. The tapered profile is configured such that the outflow end of the anchor frame subcomponent minimizes obstructing the left ventricular outflow track (LVOT). For example, wherein the prosthetic valve is used to replace a mitral valve, a shorter portion of the anchor frame subcomponent may be orientated to face the interventricular septum (the anterior portion of the tissue annulus) whereas the longer portion of the anchor frame subcomponent may lay adjacent the posterior wall of the left ventricle.

In various embodiments, the anchor frame subcomponent is provided with an outwardly flared inflow end that is conformal to an inflow end of a tissue annulus, such as that of the mitral valve tissue annulus at the left atrium. The outwardly flared anchor frame subcomponent inflow end and/or in combination with the retention element, facilitates, among other things, the securing of the prosthetic valve against axial forces from atrial pressure when the leaflets are open.

In various embodiments, the prosthetic valve may be retrieved after deployment within the tissue annulus. The leaflet frame subcomponent is provided with a retrieval tether coupled to the leaflet frame subcomponent inflow end that is operable to compress the leaflet frame subcomponent to a smaller diameter and to pull the leaflet frame subcomponent into a retrieval sheath. The anchor frame subcomponent is operable to evert under the force of the retrieval tether pulling the leaflet frame subcomponent so as to compress and pull the anchor frame subcomponent into the retrieval sheath subsequent to the leaflet frame subcomponent. The anchor frame subcomponent may be provided tissue anchor elements configured to allow for repositioning and removal of the anchor frame from the tissue annulus with minimal trauma, discussed in greater detail herein.

Although it is appreciated that the examples of the prosthetic valve may be suitable for either surgical or transcatheter applications, examples provided herein are presented as for transcatheter applications to avoid the repetition if surgical examples are also presented. Therefore, the inventive concepts are applicable for both surgical and transcatheter applications and not limited to only transcatheter applications.

Various embodiments illustrated and described herein are directed to a prosthetic valve 1000. The prosthetic valve 1000 is transitionable between a delivery, compressed, un-nested configuration and a deployed, expanded, nested configuration in-situ. FIG. 1A is a side view of the prosthetic valve 1000 in the pre-deployed un-nested configuration showing a leaflet frame subcomponent 1200, an anchor frame subcomponent 1100, a connecting sheath 1300 therebetween in coaxial serial alignment with and connecting the leaflet frame subcomponent 1200 to the anchor frame subcomponent 1100, further including a retention element 1400 coupled to the connecting sheath 1300 adjacent the leaflet frame subcomponent 1200. FIG. 1B1 is a side view of the prosthetic valve 1000 in an expanded pre-deployed configuration showing the leaflet frame subcomponent 1200 and the anchor frame subcomponent 1100 having been expanded to larger diameters relative to the pre-expanded configuration of FIG. 1A.

Figure 4:
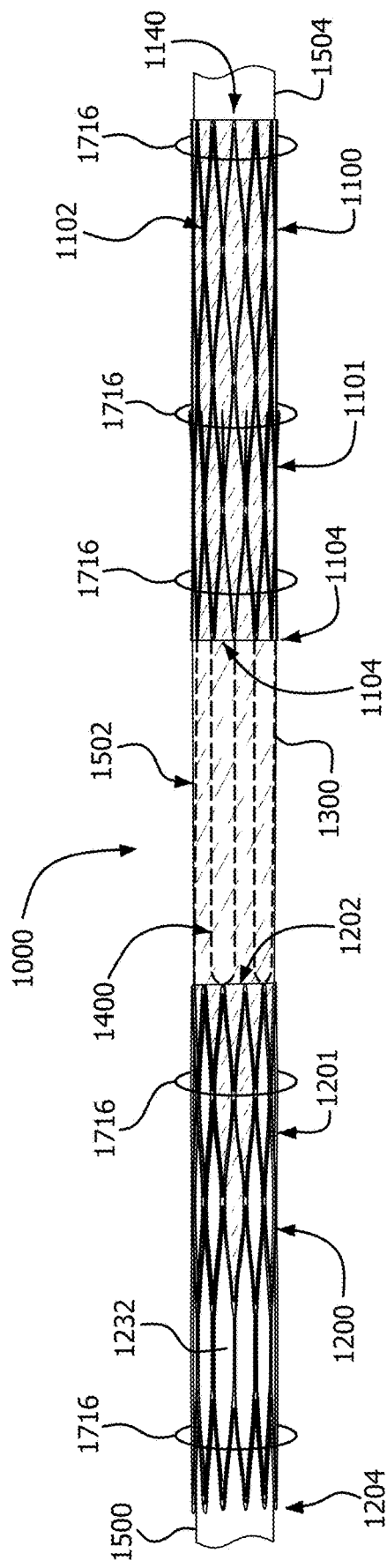
FIG. 4 is a side view of a prosthetic valve in a compressed pre-deployed configuration mounted on a delivery catheter, according to some embodiments.
Figure 7A:
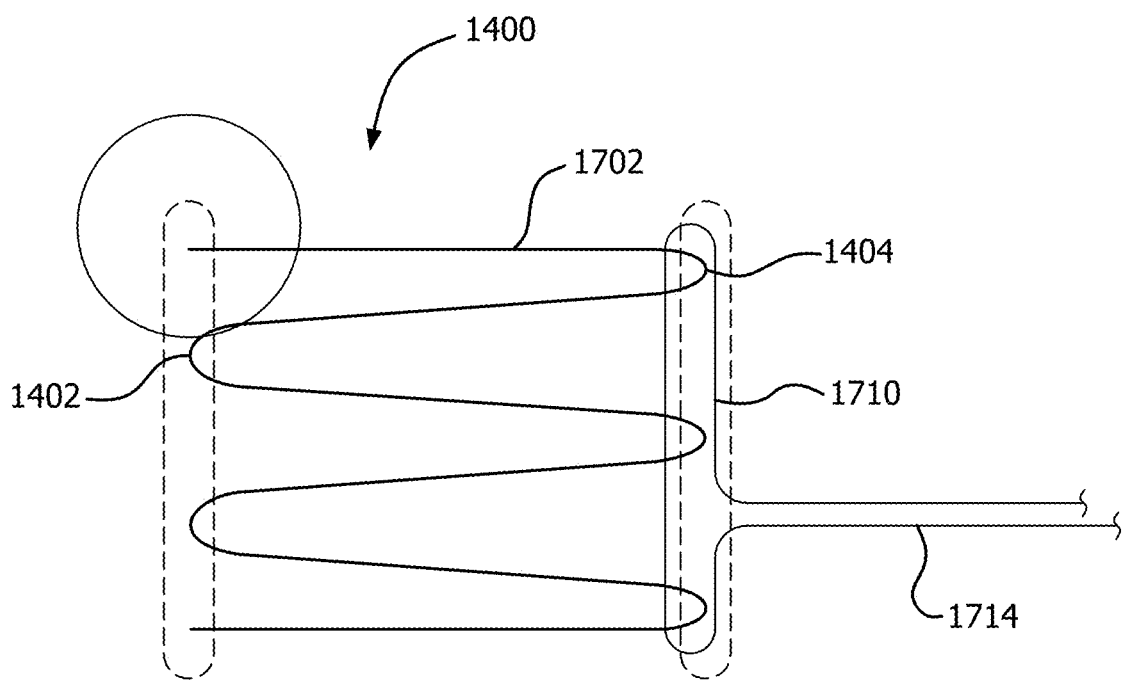
FIG. 7A is a side view of a retention element in a partially compressed configuration, according to some embodiments.
Figure 7B:
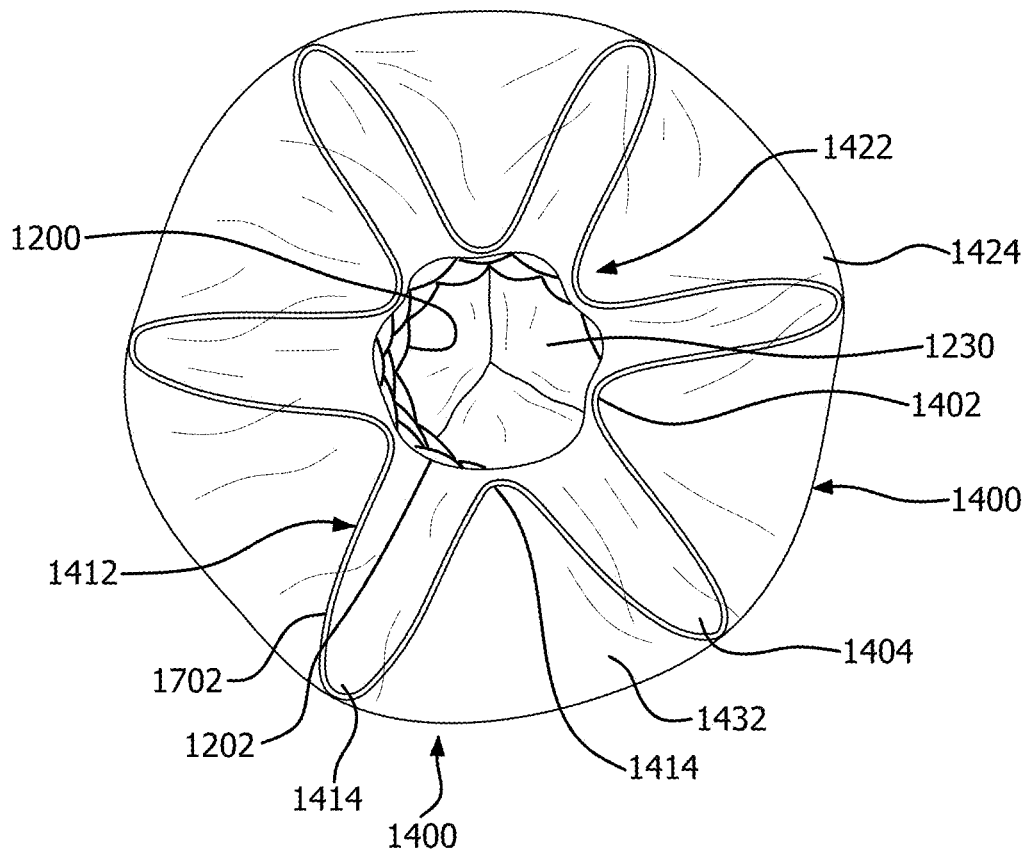
FIG. 7B is a top perspective view of a prosthetic valve in accordance with the embodiment of FIG. 1B1 showing the retention element of FIG. 7A in an expanded configuration, according to some embodiments.
Figure 7C:
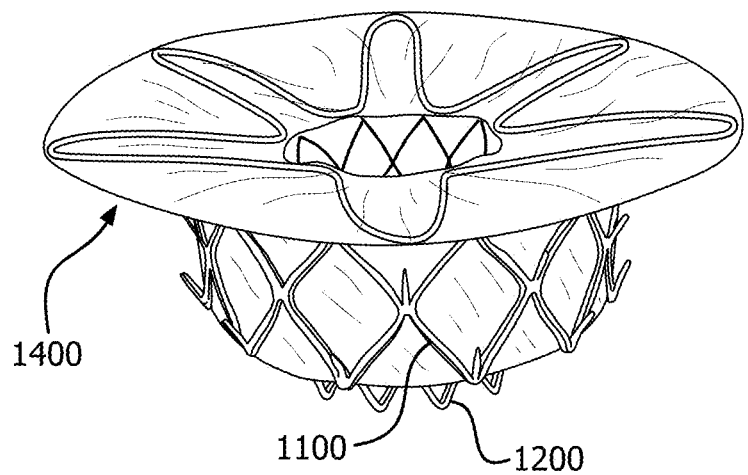
FIG. 7C is a side perspective view of the prosthetic valve of FIG. 7B showing the retention element of FIG. 7A in an expanded configuration.

The view of FIG. 1B1 would be as if the prosthetic valve 1000, as shown in FIG. 1A, was unconstrained from a constrained pre-nested configuration, such as when the prosthetic valve is placed over a delivery catheter 1504 prior to constraining onto the delivery catheter by a containing element 1716, as shown in FIG. 4. The connecting sheath 1300 defines a tapered configuration extending from the leaflet frame subcomponent 1200 and the anchor frame subcomponent 1100. The retention element 1400 may be either constrained by a restraining element, discussed below, or allowed to take the shape of the tapered configuration of the connecting sheath 1300. The leaflet frame subcomponent 1200 and the anchor frame subcomponent 1100 are configured to be nestable. FIG. 1C1 a simplified side cross-sectional view along cut line 1C2 of the prosthetic valve 1000 of FIG. 1B1 in an expanded pre-deployed configuration. FIG. 1C2 is a simplified side cross-sectional view along cut line 1C2 of the prosthetic valve 1000 of FIG. 1B1 in a deployed configuration as shown in FIG. 7C showing the leaflet frame subcomponent 1200 translated into the anchor frame subcomponent 1100 in nested alignment, with the connecting sheath 1300 having been everted and positioned therebetween. The retention element 1400 having been translated through the anchor frame subcomponent 1100 and deployed to extend from the leaflet frame subcomponent 1200 to the anchor frame subcomponent 1100. The leaflet frame subcomponent 1200 and an anchor frame subcomponent 1100 can be nested in-situ as will be described below.

The leaflet frame subcomponent 1200 and the anchor frame subcomponent 1100 are generally tubular shaped and operable to have a smaller delivery configuration diameter and a larger deployed configuration diameter, facilitated by balloon expansion and/or self-expansion deployment means. The connecting sheath 1300 is a flexible tubular membrane coupled about its circumference to the leaflet frame subcomponent 1200 at the leaflet frame subcomponent inflow end 1202 and to the anchor frame subcomponent 1100 at the anchor frame subcomponent outflow end 1104 operable to couple the leaflet frame subcomponent 1200 to the anchor frame subcomponent 1100. The connecting sheath 1300 is thin and flexible, and operable to fold or elastically contract to a smaller diameter in a delivery configuration. The retention element 1400 is coupled to the connecting sheath 1300 adjacent to the leaflet frame subcomponent inflow end 1202. The retention element 1400 is a flexible spring-like element that is operable to stow into a low radial profile in a delivery configuration and is operable to extend away from the leaflet frame subcomponent inflow end 1202 toward the anchor frame subcomponent inflow end 1102 under spring bias when in a deployed position. Engagement of the retention element 1400 with the anchor frame subcomponent inflow end 1102 assists in maintaining the relative position of the leaflet frame subcomponent 1200 within an anchor frame subcomponent lumen 1140.

In various embodiments, the leaflet frame subcomponent 1200 is nestable within the anchor frame subcomponent 1100. In particular, as shown, the anchor frame subcomponent 1100 and the leaflet frame subcomponent 1200 are sized and shaped in a manner that provides for the leaflet frame subcomponent 1200 being coaxially disposable or receivable at least partially within the anchor frame subcomponent 1100. Thus, in various examples, the anchor frame subcomponent 1100 is configured such that a portion of (or alternatively all of) the leaflet frame subcomponent 1200 can be received by or otherwise positioned within a space defined by the anchor frame subcomponent 1100. In some examples, the leaflet frame subcomponent 1200 is sized such that a diameter of the exterior surface of the leaflet frame subcomponent 1200 is less than a diameter of the interior surface of the anchor frame subcomponent 1100. In some examples, a diameter of the exterior surface of the leaflet frame subcomponent 1200 is in a range of between seventy five percent (75%) and ninety percent (90%) of a diameter of the interior surface of the anchor frame subcomponent 1100. In some examples, a diameter of the exterior surface of the leaflet frame subcomponent 1200 is seventy five percent (75%) or less than a diameter of the interior surface of the anchor frame subcomponent 1100. In various examples, such configurations also provide that the leaflet frame subcomponent 1200 can be received within the anchor frame subcomponent 1100. In various examples, such configurations provide that the anchor frame subcomponent 1100 can deform, such as, but not limited to being out of round or generally oval-shaped, to accommodate or otherwise conform to the native valve orifice without causing a deformation of the leaflet frame subcomponent 1200. The prosthetic valve 1000 provides a leaflet frame subcomponent 1200 that essentially floats within the anchor frame subcomponent 1100 and does not directly couple with a native valve orifice. The anchor frame subcomponent 1100 may conform to the shape of the native valve orifice whereas the leaflet frame subcomponent 1200 does not conform to the shape of the native valve orifice. The leaflet frame subcomponent 1200 remains a right circular hollow cylinder or at a preferred geometrical configuration so as to present the leaflets 1230 with a geometrically stable platform ensuring proper leaflet function, including opening and closing dynamics and, for flexible leaflets, coaptation. It is appreciated that these benefits associated with the leaflet frame subcomponent 1200 not needing to conform to the native valve orifice may be realized in either transcatheter or surgical placement of the prosthetic valve 1000.

In various embodiments, as discussed in greater detail below, the prosthetic valve 1000 is configured such that the anchor frame subcomponent 1100 and the leaflet frame subcomponent 1200 can be nested in-situ after the anchor frame subcomponent 1100 and the leaflet frame subcomponent 1200 are deployed to a treatment site in a patient's anatomy. That is, in various embodiments, the prosthetic valve 1000 can be delivered to a treatment region within a patient's anatomy with the anchor frame subcomponent 1100 and the leaflet frame subcomponent 1200 longitudinally offset relative to one another and subsequently nested with one another at the treatment site. In various embodiments, the prosthetic valve 1000 is loaded onto a delivery catheter with the anchor frame subcomponent 1100 and the leaflet frame subcomponent 1200 longitudinally offset relative to one another which presents a lower profile or diameter than if the prosthetic valve 1000 were to be loaded onto the delivery catheter in the nested configuration. A lower delivery profile of a transcatheter delivered prosthetic valve has well recognized advantages, including easier advancement though vessels.

It is appreciated that these benefits associated with the leaflet frame subcomponent 1200 not being nested into the anchor frame subcomponent 1100 during implantation may also be realized in surgical placement of the prosthetic valve 1000. By way of example, but not limited thereto, the anchor frame subcomponent 1100 may be more easily sutured into the native valve orifice without the leaflet frame subcomponent 1200 being within the anchor frame subcomponent 1100 and in close proximity to the suturing procedure lessening the chance of needle damage to the leaflets.

Leaflet Frame Subcomponent

Figure 1D:
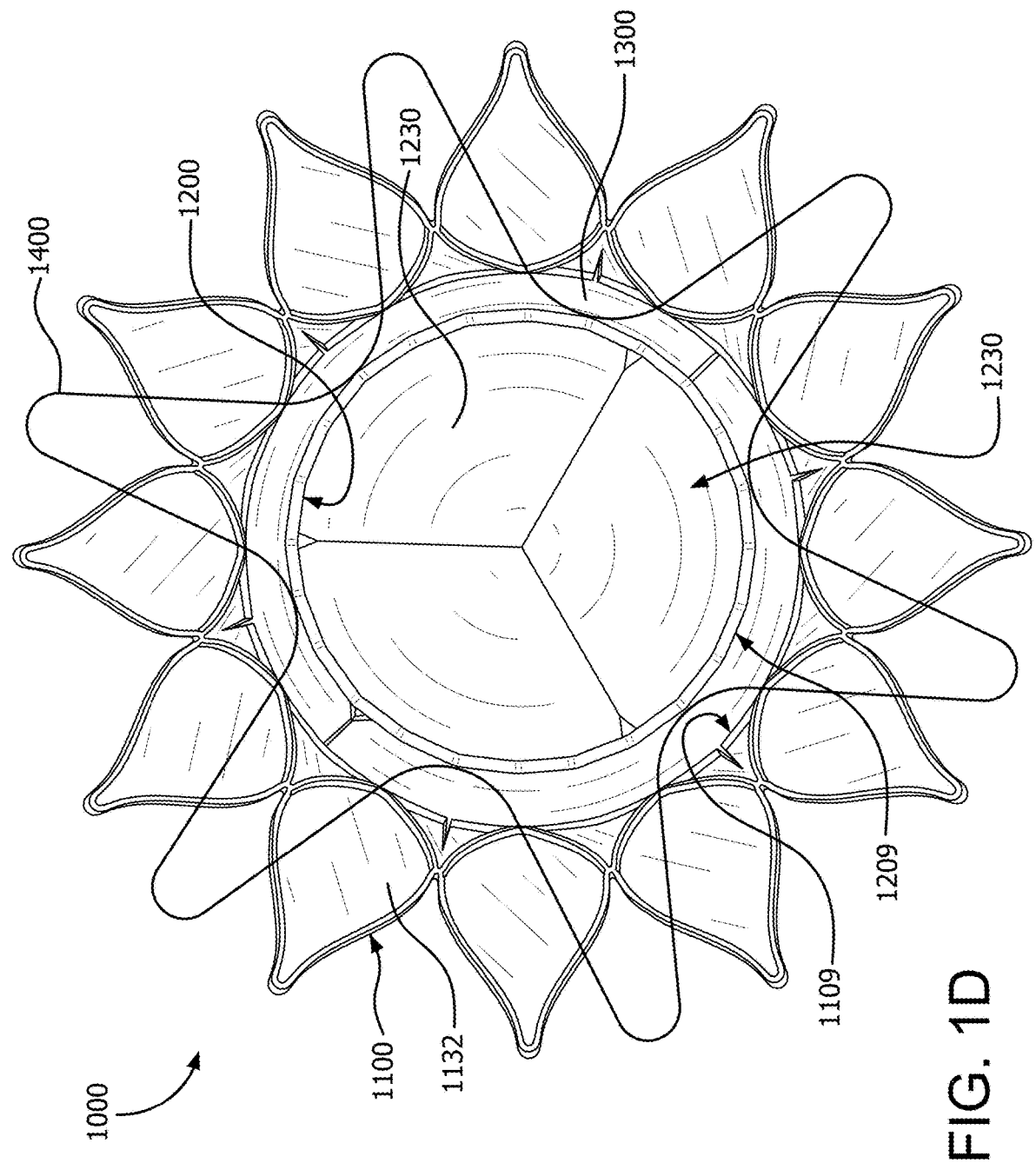
FIG. 1D is an axial view of the prosthetic valve of FIG. 1A in a deployed configuration.
Figure 1E:
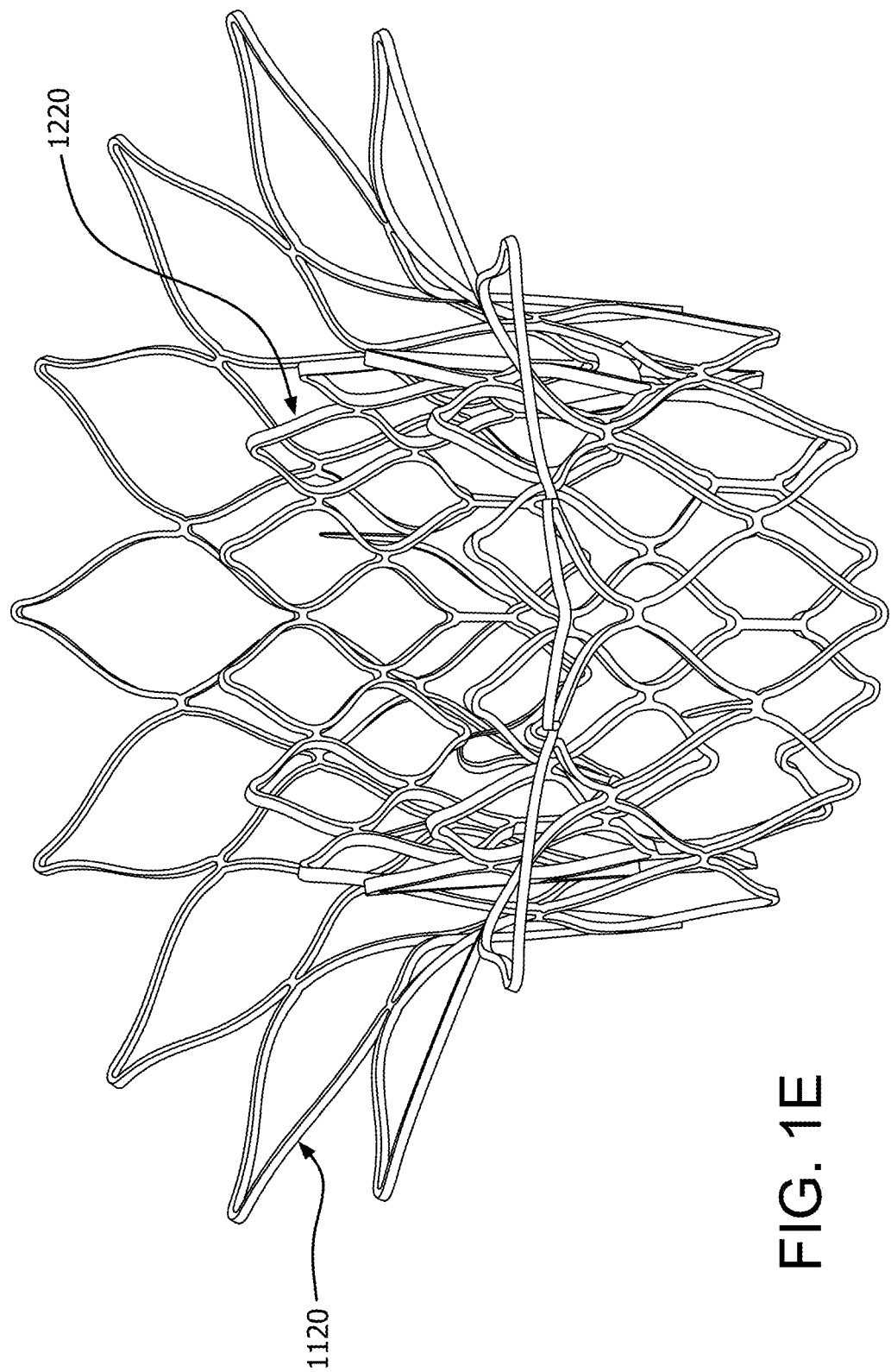
FIG. 1E is a perspective view of a leaflet frame and an anchor frame of the prosthetic valve of FIG. 1A in a deployed configuration.

FIG. 1D is an axial view of the prosthetic valve 1000 from the inflow end in the deployed configuration showing a leaflet frame subcomponent 1200, an anchor frame subcomponent 1100, and the connecting sheath 1300 therebetween (the retention element 1400 is shown without a cover in accordance with an embodiment and for clarity of visualizing the other components). FIG. 1E is a perspective view of the leaflet frame 1220 and anchor frame 1120, without other components for clarity, in the deployed configuration. The leaflet frame subcomponent 1200 provides the prosthetic valve 1000 with the functionality of a one-way valve 1030. It is understood and appreciated that one-way valves 1030 are well known in the art and may be used herein. It is appreciated that mechanical valves, biological valves, and biological and synthetic leaflet valves may be used as the one-way valve 1030 of the leaflet frame subcomponent 1200. It is also appreciated that, for transcatheter applications, the leaflet frame subcomponent 1200 is required to have a smaller-diameter compressed configuration and a larger-diameter expanded configuration, and that the one-way valve component must be able to accommodate that functionality.

Referring for FIGS. 1A-1E, in accordance with embodiments, the leaflet frame subcomponent 1200 includes a leaflet frame 1220, one or more leaflets 1230, and leaflet frame cover 1232. The leaflet frame subcomponent 1200 is generally tubular shaped defining a leaflet frame subcomponent inflow end 1202 and a leaflet frame subcomponent outflow end 1204 with a leaflet frame subcomponent lumen 1240 therethrough.

The leaflet frame 1220 provides structural support for the leaflets 1230. The leaflet frame 1220 is operable to have a smaller delivery configuration diameter and a larger deployed configuration diameter, facilitated by balloon expansion and/or self-expansion deployment means. As is known in the art, by way of example, a structure defining apertures, such as, but not limited to, a wire form or perforated wall tube that allows for the leaflet frame to have various diameters, such as a stent, is suitable for the particular purpose.

The leaflet frame subcomponent 1200 is configured to be received within at least a portion of the anchor frame subcomponent 1100, as shown in FIGS. 1C2, 1D and 10M, and as will be described in more detail below. It will be appreciated that nonlimiting examples of the leaflet frame subcomponent 1200 can be provided with a diameter (e.g., a diameter of an interior or exterior surface of the leaflet frame subcomponent 1200) in a range of between twenty (20) millimeters and thirty (30) millimeters, depending on a patient's anatomy.

Figure 2A:
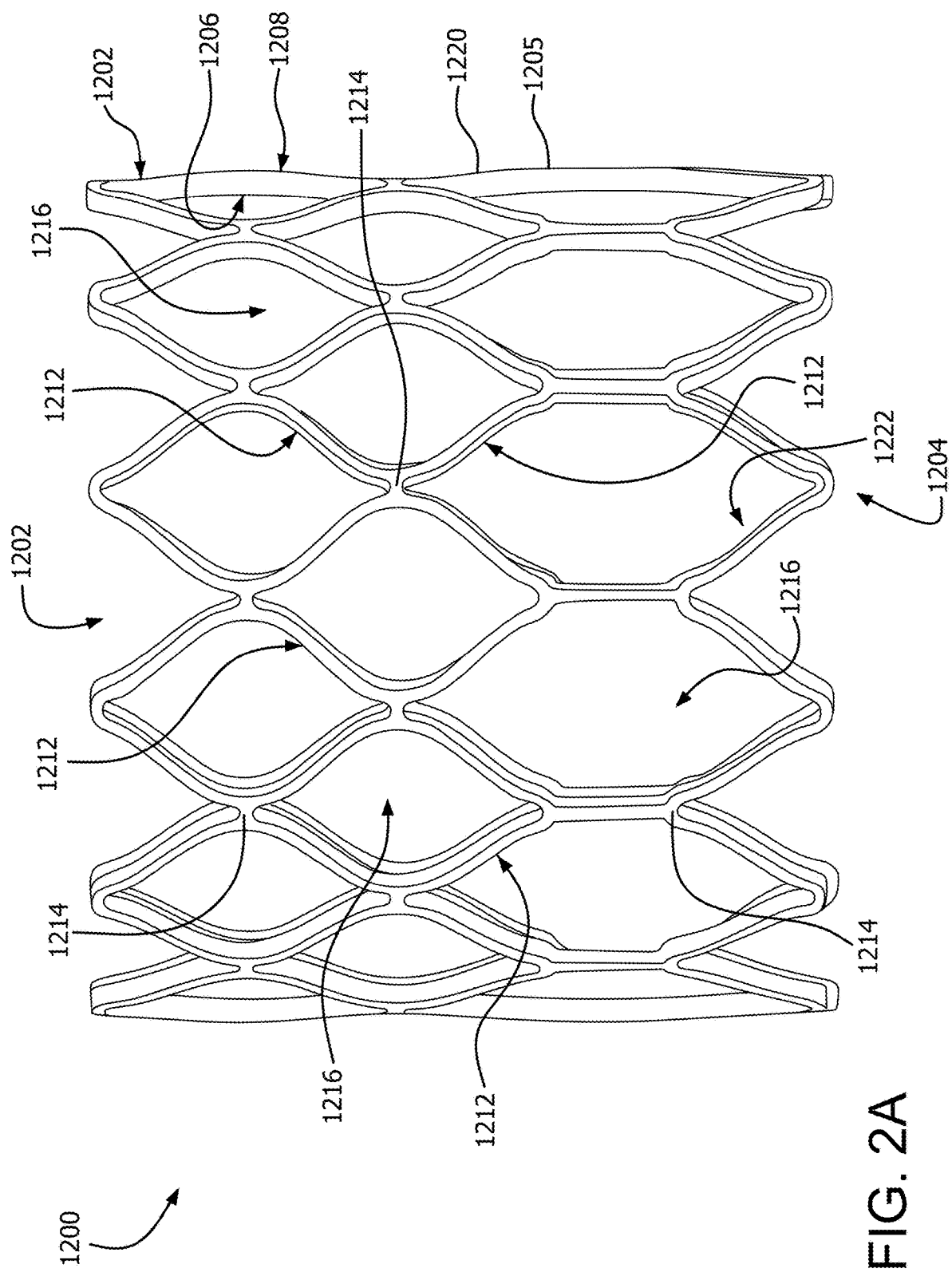
FIG. 2A is a side view of a leaflet frame subcomponent in the expanded configuration of a prosthetic valve, according to some embodiments.
Figure 2B:
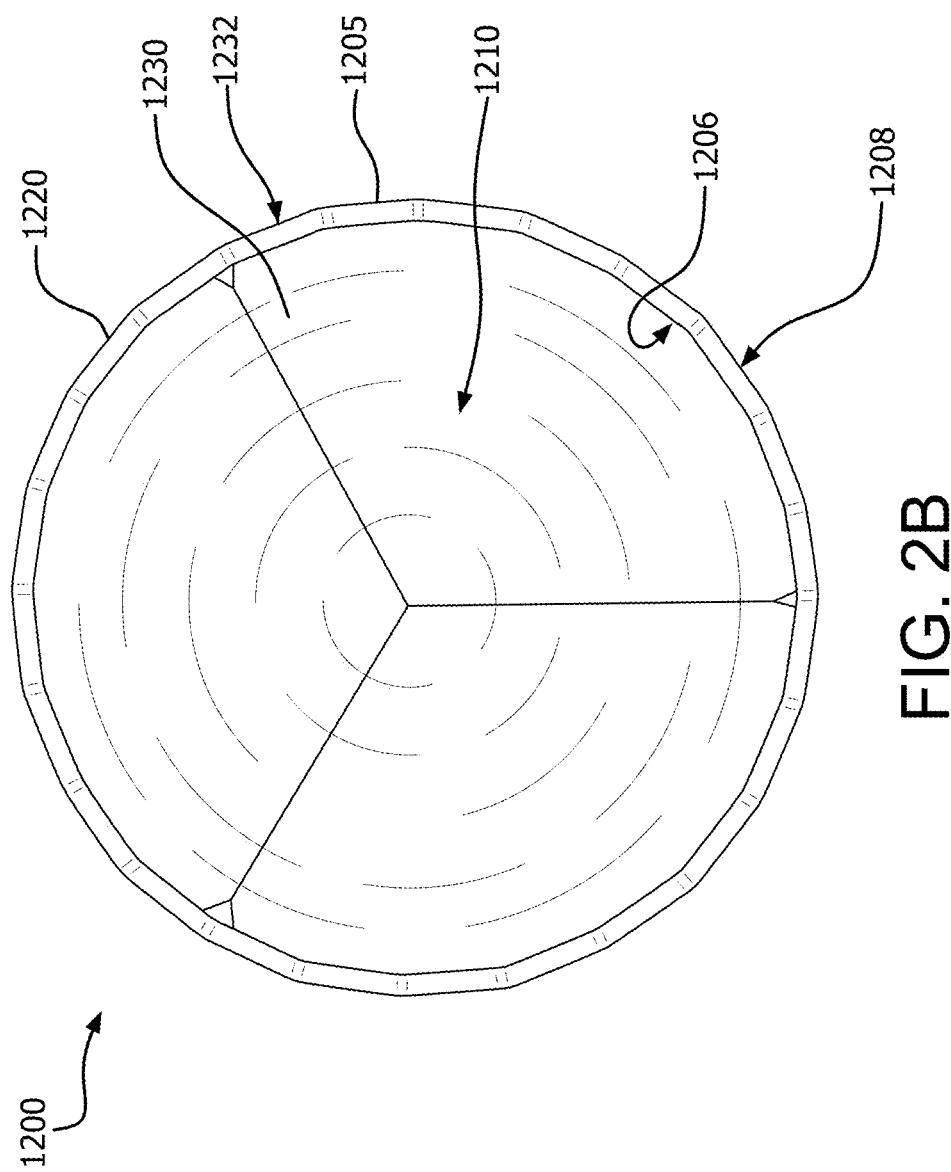
FIG. 2B is an axial view of the leaflet frame subcomponent of FIG. 2A, according to some embodiments.

FIG. 2A is a side view of the leaflet frame 1220 without leaflets 1230 nor leaflet frame cover 1232 shown for clarity. FIG. 2B is an axial view of the leaflet frame 1220 showing a plurality of leaflets 1230 therein. The leaflet frame wall 1205 of the leaflet frame 1220 may be at least partially covered with a leaflet frame cover 1232, such as an impermeable film or fabric, suitable for a particular purpose, such as to restrict fluid from passing through the leaflet frame wall 1205 of the leaflet frame 1220. For illustrative purposes, the following examples are suitable especially for a transcatheter application, but are also suitable for a surgical application.

Referring to FIG. 2A, the leaflet frame 1220 is a generally tubular member having a leaflet frame inflow end 1222 corresponding to a leaflet frame subcomponent inflow end 1202, a leaflet frame outflow end 1224 corresponding to a leaflet frame subcomponent outflow end 1204, a leaflet frame inner surface 1206 and a leaflet frame outer surface 1208 defining a leaflet frame wall 1205, wherein the leaflet frame inner surface 1206 defining a leaflet frame subcomponent lumen 1210 therethrough. The leaflet frame subcomponent lumen 1210 is a generally cylindrical void defined between the leaflet frame inflow end 1222 and the leaflet frame outflow end 1224, and the leaflet frame inner surface 1206.

The leaflet frame 1220 defines a tubular framework defining apertures or voids 1216. For example, as shown, the leaflet frame 1220 includes a plurality of frame members 1212 that are interconnected and arranged in one or more patterns. In various examples, the frame members 1112 are connected to one another at various joints 1214. In some examples, these joints 1214 operate as flex points so as to provide a preferential flexing location for the leaflet frame subcomponent 1200, such as to flex when compressed to a smaller delivery diameter such as required for transcatheter delivery. In some examples, a flex point or joint 1214 comprises a site on the leaflet frame 1220 that undergoes a high degree of bending. In some examples, the flex points or joints 1214 may comprise a geometry, structural modification or material modification, among others, that biases the leaflet frame 1220 to bend at the joint 1214 when compressed or expanded between a larger diameter and a smaller diameter.

In some examples, one or more closed cell apertures or voids 1216 are defined between the joints 1214 and the interconnected frame members 1212 of the leaflet frame subcomponent 1200. In some examples, these apertures or voids 1216 extend from the leaflet frame outer surface 1208 to the leaflet frame inner surface 1206 of the leaflet frame wall 1205 of the leaflet frame 1220. As illustrated in the embodiments of FIG. 2A, one or more of the apertures or voids 1216 define a diamond shape when the leaflet frame subcomponent 1200 is in a deployed configuration. Upon compression to a smaller diameter (e.g., a delivery diameter), one or more of the joints 1214 and the frame members 1212 deform such that the apertures or voids 1216 generally define an elongated diamond shape (e.g., as shown generally in FIG. 1A). Upon expanding the leaflet frame subcomponent 1200 to a larger diameter during deployment at a treatment site, the apertures or voids 1216 expand to define the generally wider diamond shape.

It should be appreciated that while the frame members 1212 illustrated and described herein are interconnected and define apertures or voids 1216 having generally a diamond shape, the interconnected frame members 1212 may be arranged in a number of alternative patterns without departing from the spirit or scope of the disclosure. That is, a number of alternative patterns are envisioned where the arrangement of frame members 1212 is configured in such a manner as to provide for a leaflet frame subcomponent 1200 that can be compressed to a smaller diameter for transcatheter delivery and subsequently expanded (or allowed to expand) to a larger diameter at a treatment site during deployment of the prosthetic valve 1000. Accordingly, the disclosure should not be limited to arrangements of the frame members 1212 that define diamond-shaped apertures or voids 1216. For example, a framework of the leaflet frame 1220 can define any number of features, repeatable or otherwise, such as geometric shapes and/or linear or meandering series of sinusoids. Geometric shapes can comprise any shape that facilitates circumferential compressibility and expandability.

In various embodiments, the leaflet frame 1220 may comprise or otherwise be formed from a cut tube, or any other element suitable for the particular purpose of the leaflet frame 1220 as described herein. In some examples, the leaflet frame 1220 may be etched, cut, laser cut, or stamped into a tube or a sheet of material, with the sheet then formed into a tubular structure. Alternatively, an elongated material, such as a wire, bendable strip, or a series thereof, can be bent or braided and formed into a substantially tubular structure wherein the wall of the tube comprises an open framework that is compressible to a smaller diameter and expandable to a larger diameter as illustrated and described herein.

The leaflet frame 1220 may comprise, such as, but not limited to, any elastically deformable metallic or polymeric biocompatible material, in accordance with embodiments. The leaflet frame 1220 may comprise a shape-memory material, such as nitinol, a nickel-titanium alloy. Other materials suitable for the leaflet frame 1220 include, but are not limited to, other titanium alloys, stainless steel, cobalt-nickel alloy, polypropylene, acetyl homopolymer, acetyl copolymer, other alloys or polymers, or any other biocompatible material having adequate physical and mechanical properties to function as a leaflet frame subcomponent 1200 as described herein.

In various examples, as the leaflet frame 1220 is elastically deformable so as to be self-expanding under spring loads, as those of skill will appreciate. In some examples, the leaflet frame 1220 is plastically deformable so as to be mechanically expanded such as with a balloon, as those of skill will appreciate. In yet some other examples, the leaflet frame 1220 is plastically deformable as well as elastically deformable. That is, in some examples, the leaflet frame 1220 includes one or more elastically deformable components or features and one or more plastically deformable components or features. Thus, it should be appreciated that the examples of the leaflet frame 1220 presented herein are not to be limited to a specific design or mode of expansion.

In accordance with some embodiments, the leaflet frame 1220 comprises a shape memory material operable to flex under load and retain its original shape when the load is removed, thus allowing the leaflet frame subcomponent 1200 to self-expand from a compressed shape to a predetermined shape. The leaflet frame subcomponent 1200 and the anchor frame subcomponent 1100 may comprise the same or different materials. In accordance with an embodiment, the leaflet frame 1220 is plastically deformable to be expanded by a balloon. In another embodiment the leaflet frame 1220 is elastically deformable so as to be self-expanding.

In various embodiments, the leaflet frame subcomponent 1200 supports or otherwise includes a one-way valve 1030. In some examples, the one-way valve 1030 includes one or more leaflets 1230 as shown in FIGS. 1D and 2B. A variety of mechanical valve, biological leaflet, and synthetic leaflet designs are known in the medical technology arts, any of which may be incorporated into the leaflet frame subcomponent 1200 of the present disclosure. Examples of suitable leaflet constructs and methods of attachment to leaflet frame subcomponents are illustrated and described in U.S. patent application Ser. Nos. 13/833,650, 14/973,589, and 14/622,599, the contents of each of which are incorporated herein by reference. Further examples of suitable leaflet material are presented below.

In the embodiments of FIGS. 1D and 2B, the leaflet frame subcomponent 1200 further comprises one or more flexible leaflets 1230 coupled to the leaflet frame 1220 that are operable to open to allow flow from the leaflet frame subcomponent inflow end 1202 and to pass through the leaflet frame subcomponent outflow end 1204, as shown in FIGS. 1B1-1B3, also referred to as the forward flow direction, and are operable to close to restrict flow from flowing from the leaflet frame subcomponent outflow end 1204 through the leaflet frame subcomponent inflow end 1202, also referred to as the retrograde flow direction.

In some examples, the one-way valve 1030 or leaflets 1230 are coupled to the leaflet frame inner surface 1206 of the leaflet frame 1220. In other examples, a film that comprises a leaflet material is coupled to the leaflet frame outer surface 1208 and extends through a leaflet window defined by the leaflet frame 1220. Such a configuration minimizes a potential for the leaflet 1230 to peel or delaminate, as compared to configurations where the leaflets 1230 are coupled to a leaflet frame inner surface 1206 of the leaflet frame 1220. In some examples, one or more portions of the leaflets 1230 are wrapped about one or more portions of the leaflet frame subcomponent 1200.

The leaflet frame subcomponent 1200 further comprises a leaflet frame cover 1232 that is operable to prevent the flow of fluid through the wall of the leaflet frame 1220 such that the fluid can only flow through a lumen defined by the open leaflets 1230. FIGS. 1B1-1B3 provide embodiments wherein the voids 1216 of the leaflet frame 1220 are covered by the leaflet frame cover 1232 so as to block flow through the portion of the leaflet frame 1220 that is upstream of the attachment of leaflets 1230 to the leaflet frame 1220. In accordance with an example, the leaflet frame cover 1232 may be an impermeable film, sheet or membrane material that is wrapped around and coupled to the leaflet frame outer surface 1208. The leaflet frame cover 1232 may comprise any suitable material known in the art. By way of example, the leaflet frame cover 1232 may be a film, fabric, among others.

The leaflet frame cover 1232 may be a sheet-like material that is biologically compatible and configured to couple to the leaflet frame 1220. In various examples, the biocompatible material is a film that is not of a biological source and that is sufficiently flexible and strong for the particular purpose, such as a biocompatible polymer. In an embodiment, the film comprises a biocompatible polymer (e.g., ePTFE). In some examples, the film is a composite of two or more materials. The film may comprise one or more of a membrane, composite material of two or more components, or laminate of more than one layer of material. In various examples, the construction of and materials used in the film are such that the leaflet frame cover 1232 is impermeable to fluid flow.

Anchor Frame Subcomponent

Figure 3A:
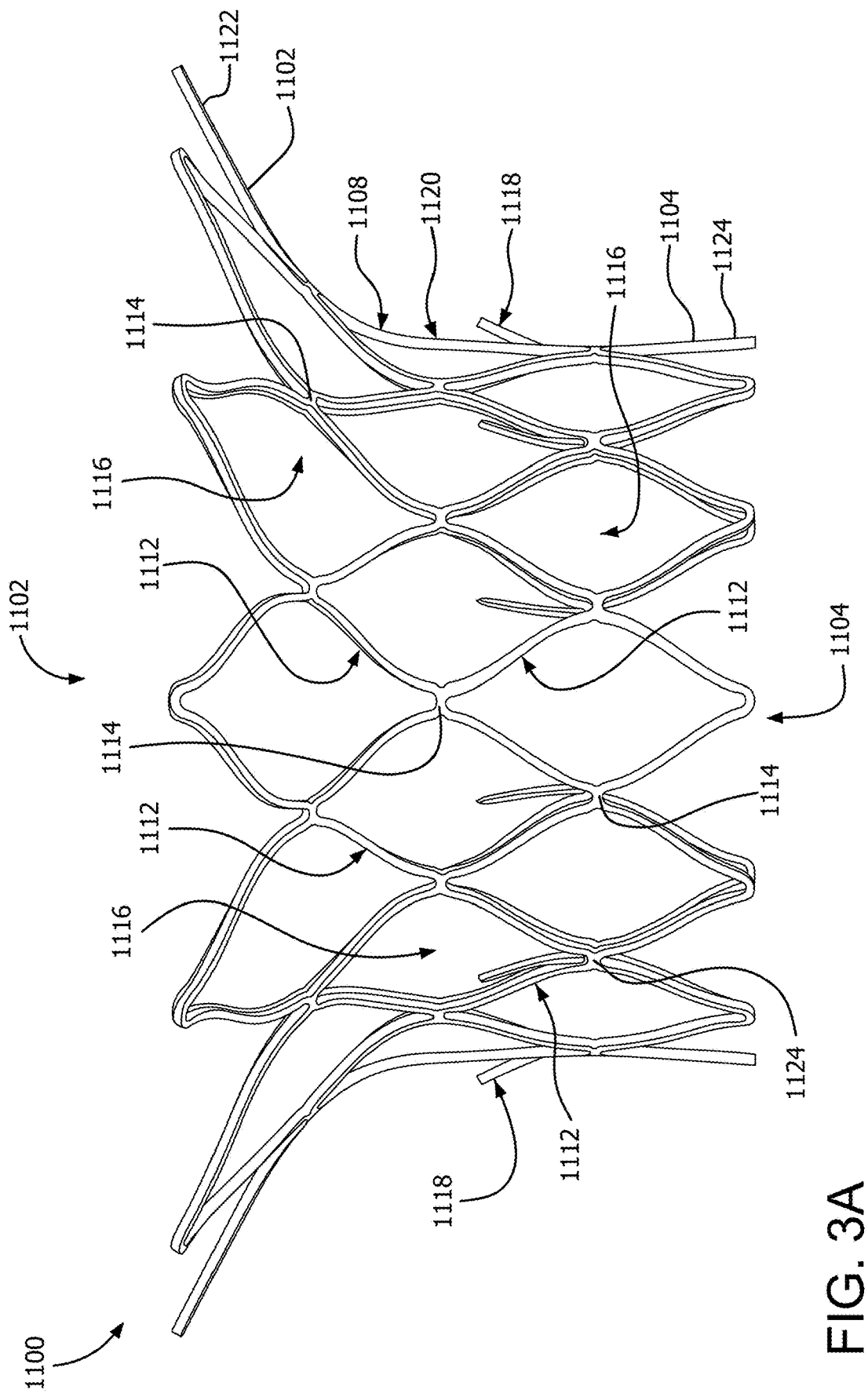
FIG. 3A is a side view of an anchor frame subcomponent in the expanded configuration of a prosthetic valve, according to some embodiments.
Figure 3B:
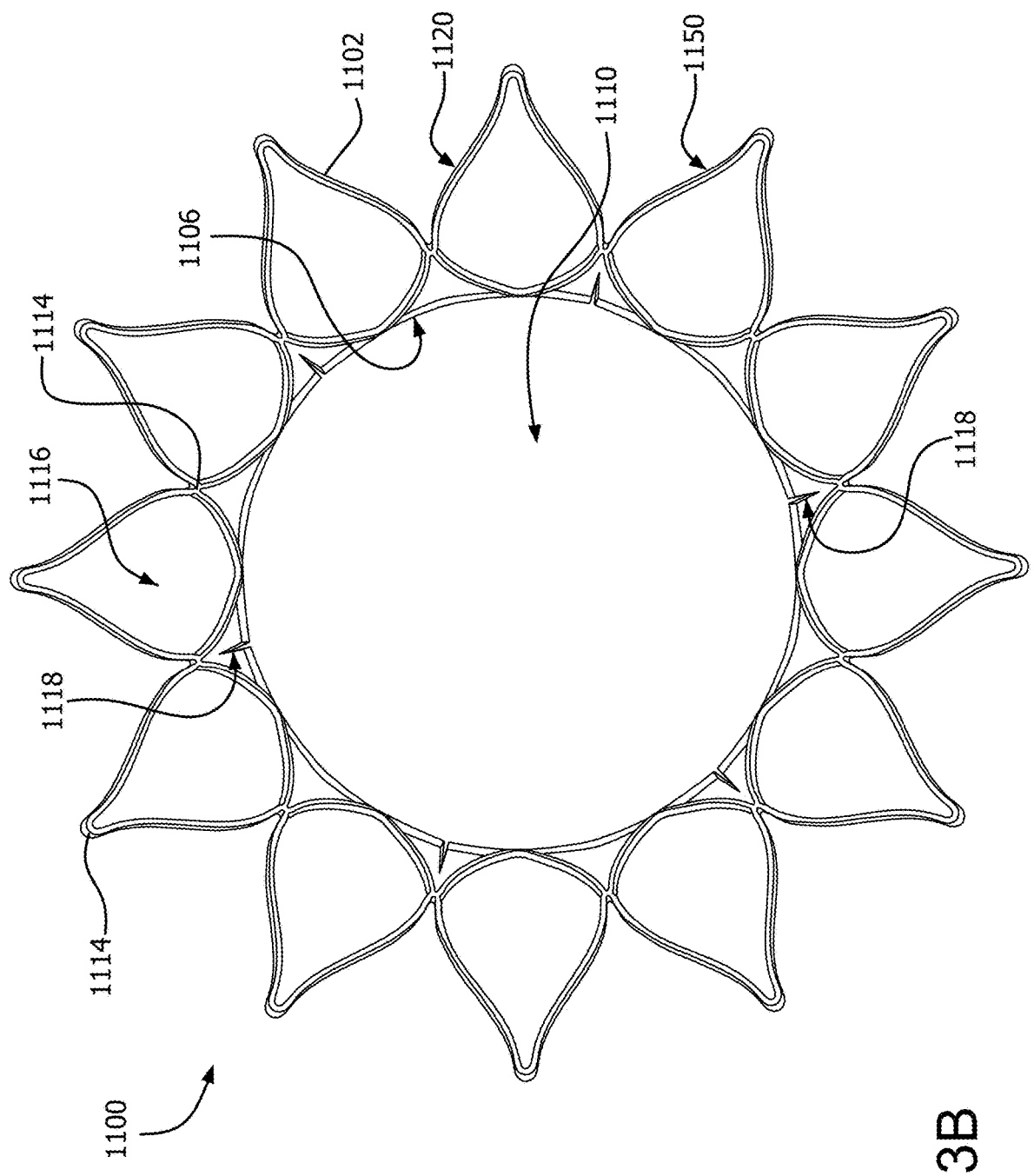
FIG. 3B is an axial view of the anchor frame subcomponent of FIG. 3A.

In accordance with an embodiment, the anchor frame subcomponent 1100 includes an anchor frame 1120 and an anchor frame cover 1132 as shown in FIGS. 1B1-1B3. FIG. 3A is a side view of the anchor frame 1120. FIG. 3B is an axial view of the anchor frame 1120. The anchor frame wall 1105 of the anchor frame 1120 may be at least partially covered, such as with a film or fabric, not shown for clarity, suitable for a particular purpose, such as to restrict fluid from passing through the anchor frame wall 1105 of the anchor frame 1120, or to encourage tissue ingrowth of the anchor frame subcomponent 1100 with the implant site. The anchor frame cover 1132 may be coupled to the inner surface, outer surface, or both inner surface and outer surface of the anchor frame 1120. For illustrative purposes, the following examples are suitable especially for a transcatheter application, but are also suitable for a surgical application.

FIGS. 3A and 3B are side and axial views, respectively, of the anchor frame 1120 without the anchor frame cover 1132 for clarity, in accordance with an embodiment. The anchor frame 1120 is a generally tubular member having an anchor frame inflow end 1122 corresponding to an anchor frame subcomponent inflow end 1102, an anchor frame outflow end 1124 corresponding to an anchor frame subcomponent outflow end 1104, an anchor frame inner surface 1106 and an anchor frame outer surface 1108 defining an anchor frame wall 1105, wherein the anchor frame inner surface 1106 defining an anchor frame subcomponent lumen 1110 therethrough. The anchor frame subcomponent lumen 1110 is a generally cylindrical void defined between the anchor frame subcomponent inflow end 1102 and the anchor frame subcomponent outflow end 1104, and the anchor frame inner surface 1106 of the anchor frame subcomponent 1100. However, in-situ, the anchor frame subcomponent lumen 1110 may adopt an irregular cross section, depending on the geometry of the tissue orifice into which it is placed and the conformity of the anchor frame subcomponent 1100 to the tissue annulus at the implant site.

In various examples, the anchor frame 1120 is configured to couple to a native valve orifice. Accordingly, in various examples, a diameter of the anchor frame 1120 (e.g., a diameter of the anchor frame outer surface 1108, and essentially the diameter of the anchor frame subcomponent outer surface 1109, shown in FIG. 1D, of the anchor frame subcomponent 1100) is sized in accordance with patient anatomy. It will be appreciated that nonlimiting examples of an anchor frame subcomponent 1100 can be provided with a diameter (e.g., a diameter of an exterior surface of the anchor frame subcomponent 1100) in a range of between twenty five (25) millimeters and fifty (50) millimeters, depending on a patient's anatomy. However, anchor frames 1120 having diameters (e.g., a diameter of an anchor frame outer surface 1106 of the anchor frame 1120) in excess of fifty (50) millimeters are also envisioned and fall within the scope of the present disclosure, depending on patient anatomy. Note that the anchor frame subcomponent inner surface 1107, shown in FIG. 1D, of the anchor frame subcomponent 1100 has a diameter at least slightly larger than the leaflet frame outer surface 1208 of the leaflet frame subcomponent 1200 such that the leaflet frame subcomponent 1200 may telescopically nest within the anchor frame subcomponent 1100.

In another embodiment the anchor frame 1120 is elastically deformable so as to be self-expanding. In accordance with some embodiments, the anchor frame 1120 comprises a shape memory material operable to flex under load and retain its original shape when the load is removed, thus allowing the anchor frame subcomponent 1100 to self-expand from a compressed shape to a predetermined larger shape. The anchor frame 1120 may comprise the same or different materials as the leaflet frame 1220. In accordance with an embodiment, the anchor frame 1120 is plastically deformable, such that it may be mechanically expanded such as by a balloon.

In some embodiments, the anchor frame 1120 defines a tubular mesh having a framework defining apertures or voids 1116 as shown in FIG. 3A. For example, as shown, the anchor frame 1120 includes a plurality of frame members 1112 that are interconnected and arranged in one or more patterns. In some examples, these patterns repeat one or more times. In some such examples, the frame members 1112 are arranged and interconnected such that the anchor frame 1120 includes a plurality of patterned rows. In various examples, the frame members 1112 are connected to one another at various joints 1114. In some examples, these joints 1114 operate as flex points so as to provide a preferential flexing location for the anchor frame 1120 to flex when compressed to a smaller delivery diameter and when forces from the surrounding anatomy act to compress the anchor frame 1120 during normal operation after delivery and deployment of the prosthetic valve 1000. In some examples, a flex point or joint 1114 comprises a site on the anchor frame 1120 that undergoes a high degree of bending. In some examples, the joints 1114 may comprise a geometry, structural modification or material modification, among others, that biases the anchor frame 1120 to bend at the flex point or joint 1114 when compressed.

In some embodiments, one or more closed cell apertures or voids 1116 are defined between the joints 1114 and the interconnected frame members 1112 of the anchor frame 1120. In some examples, these apertures or voids 1116 extend from the anchor frame outer surface 1108 to the anchor frame subcomponent inner surface 1107 of the anchor frame 1120. As illustrated in the embodiments of FIGS. 3A and 3B, one or more of the apertures or voids 1116 define a diamond shape when the anchor frame 1120 is in a deployed configuration. Upon compression to a smaller diameter (e.g., a delivery diameter), one or more of the joints 1114 and the frame members 1112 deform such that the apertures or voids 1116 generally define an elongated diamond shape (e.g., as shown generally in FIG. 1A). Upon expanding the anchor frame 1120 to a larger diameter during deployment at a treatment site, the apertures or voids 1116 expand to define the generally wider diamond shape.

It should be appreciated that while the frame members 1112 illustrated and described herein are interconnected and define apertures or voids 1116 having generally a diamond shape, the interconnected frame members 1112 may be arranged in a number of alternative patterns. For example, a framework of the anchor frame 1120 can define any number of features, repeatable or otherwise, such as geometric shapes and/or linear or meandering series of sinusoids. Geometric shapes can comprise any shape that facilitates circumferential compressibility and expandability of the anchor frame 1120. That is, a number of alternative patterns are envisioned where the arrangement of frame members 1112 is configured in such a manner as to provide for an anchor frame 1120 that can be compressed to a smaller diameter for transcatheter delivery and subsequently expanded (or allowed to expand) to a larger diameter at a treatment site during deployment of the prosthetic valve 1000. Accordingly, the disclosure should not be read as being limited to arrangements of the frame members 1112 that define diamond-shaped apertures or voids 1116.

In various embodiments, the anchor frame 1120 may comprise or otherwise be formed from a cut tube, or any other element suitable for the particular purpose of the anchor frame 1120 as described herein. In some examples, the anchor frame 1120 may be etched, cut, laser cut, or stamped into a tube or a sheet of material, with the sheet then formed into a tubular structure. Alternatively, an elongated material, such as a wire, bendable strip, or a series thereof, can be bent or braided and formed into a tubular structure wherein the wall of the tube comprises an open framework that is compressible to a smaller diameter in a generally uniform and circumferential manner and expandable to a larger diameter as illustrated and described herein.

The anchor frame 1120 can comprise any metallic or polymeric biocompatible material. For example, the anchor frame 1120 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

In various examples, the anchor frame 1120 is elastically deformable so as to be self-expanding under spring loads, as those of skill will appreciate. In some examples, the anchor frame 1120 is plastically deformable so as to be mechanically expanded such as with a balloon, as those of skill will appreciate. In yet some other examples, the anchor frame 1120 is plastically deformable as well as elastically deformable. That is, in some examples, the anchor frame 1120 includes one or more elastically deformable components or features and one or more plastically deformable components or features. Thus, it should be appreciated that the examples of the anchor frame 1120 presented herein are not to be limited to a specific design or mode of expansion.

In various embodiments, the anchor frame subcomponent 1100 is configured to provide positive engagement with an implant site to firmly anchor the prosthetic valve 1000 to the site. Such positive engagement with the implant site may be facilitated by one or more of the following, but not limited thereto: expansion spring bias of the anchor frame 1120; hoop strength of the expanded anchor frame 1120, tissue engagement features, and the geometric shape, contour and/or texture of the anchor frame subcomponent outer surface 1109.

For instance, in various examples, the anchor frame subcomponent 1100 includes one or more tissue engagement features 1118 that are configured to engage one or more regions of tissue at the tissue orifice surrounding the prosthetic valve 1000. In various examples, the tissue engagement features 1118 comprise one or more barbs or tissue anchors. The tissue engagement features 1118 will be discussed in detail later.

In some embodiments, the anchor frame 1120 defines a flange or a flared portion 1130 at the anchor frame subcomponent inflow end 1102 that flares or tapers radially outward when in the deployed configuration. For example, as shown in at least FIGS. 1B1, 1B2, 1B3, 2A, 5A-5C, 5E, and 10B-10M, the anchor frame subcomponent inflow end 1102 is flared or otherwise tapered radially outward when in the deployed configuration. That is, as shown, the anchor frame subcomponent inflow end 1102 has a larger deployed diameter than does the anchor frame subcomponent outflow end 1104. In various examples, as discussed in greater detail below, such a configuration operates to minimize migration risks and helps facilitate abutment of the anchor frame subcomponent 1100 with native tissue annulus at the implant site.

In some embodiments, the anchor frame subcomponent 1100 further comprises a flange element 1150 separate from, adjacent to, and coaxial with the anchor frame inflow end 1122 of the anchor frame 1120. FIG. 1B2 is a side view of the prosthetic valve 1000 in an expanded pre-deployed configuration showing the leaflet frame subcomponent 1200 and the anchor frame subcomponent 1100 having been expanded to larger diameters so as to show the details of the flange element 1150 as compared with an integral flange or flared portion 1130 of the anchor frame inflow end 1122 of anchor frame 1120 of the embodiment of FIG. 1B1. The flange element 1150 defines a flange or a flared portion 1130 of the anchor frame subcomponent 1100 that also defines the anchor frame subcomponent inflow end 1102 that flares or tapers radially outward when in the deployed configuration. The flange element 1150 is a generally tubular member of substantially the same construction as the anchor frame 1120. The flange element 1150 has a flange element inflow end 1152, a flange element outflow end 1154, a flange element inner surface 1156, and a flange element outer surface 1158 defining a flange element wall 1155 defining flange voids 1157. The flange element inner surface 1156 defines a portion of the anchor frame subcomponent lumen 1110 therethrough. In-situ, the flange element 1150 may adopt an irregular cross section, depending on the geometry of the tissue orifice into which it is placed and the conformity of the flange element 1150 to the tissue annulus at the implant site.

The flange element 1150 is coupled to the anchor frame inflow end 1122 by the anchor frame cover 1132 which is described below. The flange element 1150 defines a flange element inflow end 1152 and a flange element outflow end 1154. The flange element 1150 is located adjacent to, coaxial with, and axially spaced apart from the anchor frame 1120, with the flange element outflow end 1154 adjacent to but separate from the anchor frame inflow end 1122.

FIG. 1B2 shows the flange element 1150 flaring outward in a trumpet shape having a concave curvature to the flange element outer surface 1158. FIG. 1B3 shows another embodiment of the flange element 1150 wherein the flange element outer surface 1158 defines a convex curvature. The shape of the anatomy into which the anchor frame subcomponent 1100 is placed will determine the best choice of shape for the flange element 1150 of FIGS. 1B2-1B3 or the flared portion 1130 of the anchor frame subcomponent 1100 of FIG. 1B1. The flared portion 1130 of the anchor frame subcomponent 1100 of FIG. 1B1 may also define the convex curvature of the embodiment of FIG. 1B3 suitable for a particular anatomy into which is it placed.

The anchor frame subcomponent 1100 further comprises an anchor frame cover 1132 that is operable to prevent the flow of fluid through the anchor frame wall 1105 of the anchor frame 1120. The anchor frame cover 1132 may also be operable to provide a favorable surface for tissue abutment at the tissue annulus, and further, may be operable to facilitate tissue ingrowth which may be advantageous for fixation of the prosthetic valve 1000 to the tissue annulus, facilitate a favorable biological response of the blood (e.g., to prevent a thrombotic response), and/or facilitate sealing of the prosthetic valve 1000 with the tissue orifice to minimize para-valvular leakage. FIG. 1B provides an embodiment wherein all of the voids 1116 of the anchor frame 1120 are covered by the anchor frame cover 1132 so as to block flow through the anchor frame wall 1105. In accordance with an example, the anchor frame cover 1132 may be an impermeable film, sheet or membrane material that is wrapped around and coupled to the anchor frame outer surface 1108. The anchor frame cover 1132 may comprise any suitable material known in the art. By way of example, the anchor frame cover 1132 may be a film, fabric, among others.

The anchor frame cover 1132 may be a sheet-like material that is biologically compatible and configured to couple to the anchor frame 1120. In various examples, the biocompatible material is a film that is not of a biological source and that is sufficiently flexible and strong for the particular purpose, such as a biocompatible polymer. In an embodiment, the film comprises a biocompatible polymer (e.g., ePTFE). In some examples, the film is a composite of two or more materials. The film may comprise one or more of a membrane, composite material, or laminate. In various examples, the construction of and materials used in the film are such that the anchor frame cover 1132 is impermeable to fluid flow. In various examples, the construction of and materials used in the film are such that the anchor frame cover 1132 promotes cellular ingrowth, adhesion, and/or attachment. That is, in various examples, the anchor frame cover 1132 is constructed in a manner that promotes the ingrowth of tissue into one or more portions of the anchor frame cover 1132. It will be appreciated that cellular ingrowth may further increase sealing of the prosthetic valve with the tissue orifice and helps minimize para-valvular leakage, that is, leakage between the prosthetic valve and the tissue into which it is coupled.

Connecting Sheath

In accordance with embodiments of the prosthetic valve 1000, the anchor frame subcomponent 1100 and the leaflet frame subcomponent 1200 are coupled together by the connecting sheath 1300. Referring to FIGS. 1A-1C2, the connecting sheath 1300 is coupled to the anchor frame subcomponent outflow end 1104 of the anchor frame subcomponent 1100 at a connecting sheath inflow end 1322 and is coupled to the leaflet frame subcomponent inflow end 1202 at a connecting sheath outflow end 1324. The connecting sheath 1300 is a thin-walled flexible tubular member that defines a connecting sheath lumen 1340 in fluid communication with the anchor frame subcomponent lumen 1140 and the leaflet frame subcomponent lumen 1240 when in the pre-deployed configuration. When the leaflet frame subcomponent 1200 is nested into the anchor frame subcomponent 1100 the connecting sheath 1300 is operable to fold and evert so as to lie between the leaflet frame subcomponent 1200 and the anchor frame subcomponent 1100. The connecting sheath 1300 may comprise any suitable material known in the art. By way of example, the connecting sheath 1300 may be a film, fabric, membrane, among others, that is flexible and impermeable to fluid flow.

Referring to FIG. 4, showing a side view of the prosthetic valve 1000 in a pre-deployed configuration on a delivery catheter 1504 of a delivery device 1500, in some examples, the connecting sheath 1300 is disposed within and/or about the anchor frame subcomponent 1100 and the leaflet frame subcomponent 1200. In some examples, the connecting sheath 1300 is a contiguous film that at least extends between and operates to couple the anchor frame subcomponent 1100 and the leaflet frame subcomponent 1200 to one another. In some examples, the connecting sheath 1300 extends not only between but also over or within either or both of the anchor frame subcomponent 1100 and the leaflet frame subcomponent 1200. In some examples, the connecting sheath 1300 is a contiguous film with that of the anchor frame cover 1132 and/or the leaflet frame cover 1232 that at least extends between and operates to couple the anchor frame subcomponent 1100 and the leaflet frame subcomponent 1200 to one another. In some examples, the connecting sheath 1300 is formed from a generally tubular material and at least partially covers one or more of the anchor frame subcomponent 1100 and the leaflet frame subcomponent 1200. In some examples, the connecting sheath 1300 is formed by wrapping a film over and around a cylindrical mandrel that defines a variable diameter to match the respective inner diameter of each of the leaflet frame 1220 and anchor frame 1120 with a tapered portion therebetween to transition from the smaller diameter of the leaflet frame 1220 to the larger diameter of the anchor frame 1120. Either or both of the anchor frame 1120 and the leaflet frame 1220 are slid over the film and bonded thereto to the inner surface of the frames. In some examples, the connecting sheath 1300 is formed by wrapping the film over and around either or both of the anchor frame 1120 and the leaflet frame 1220 and bonded thereto to the outer surface of the frames.

The connecting sheath 1300 is generally any sheet-like material that is biologically compatible and configured to couple to the anchor frame subcomponent 1100 and the leaflet frame subcomponent 1200. In various examples, the biocompatible material is a film that is not of a biological source and that is sufficiently flexible and strong for the particular purpose, such as a biocompatible polymer. In an embodiment, the film comprises a biocompatible polymer (e.g., ePTFE). In some examples, the film is a composite of two or more materials. The film may comprise one or more of a membrane, composite material, or laminate. In various examples, the construction of and materials used in the film are such that the connecting sheath 1300 is impermeable to fluid flow.

Figure 6D:
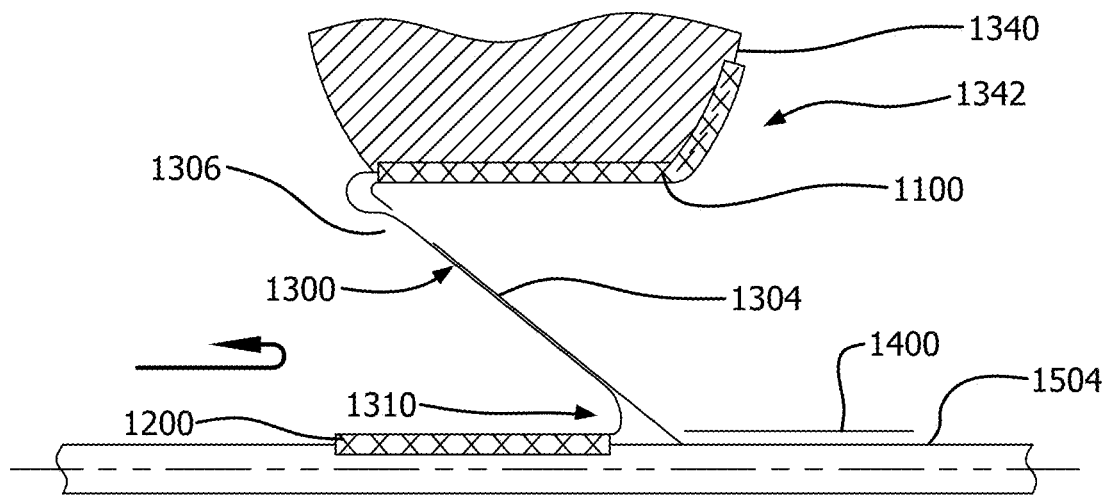
FIG. 6D is a simplified representation cross-sectional view of the prosthetic valve deployed within a native valve orifice, in accordance with the embodiment of FIG. 6A.
Figure 6D:
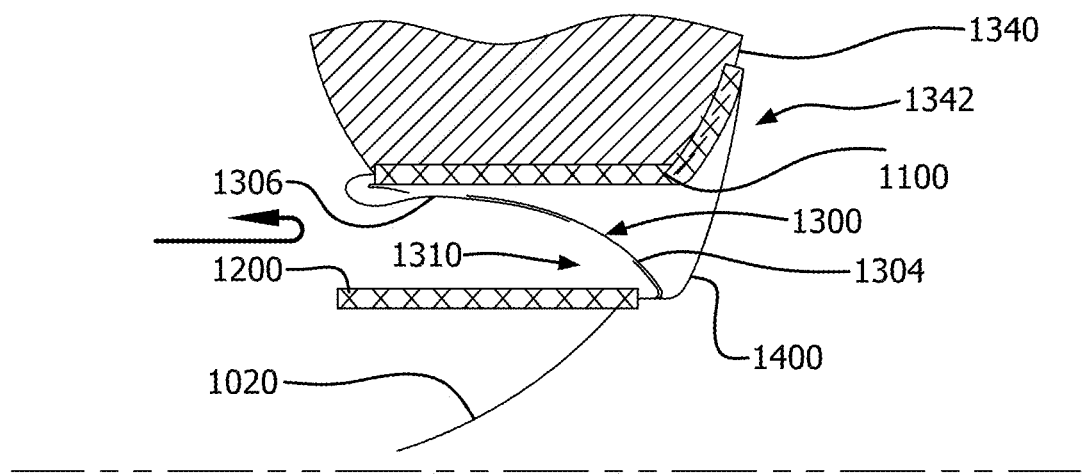

In various examples, the connecting sheath 1300 is a tubular member having a connecting sheath wall 1305 that is impervious to fluid flow and controls the flow of fluid only through the connecting sheath lumen 1340 particularly during deployment of the prosthetic valve 1000 into the tissue orifice, as shown in FIGS. 6B1-6C2, and acts as an impermeable seal between the leaflet frame subcomponent 1200 and the anchor frame subcomponent 1100 when in the deployed nested configuration as shown in FIG. 6D. As will be discussed further below, during deployment of the prosthetic valve 1000, with the anchor frame subcomponent 1100 deployed within the tissue annulus and the leaflet frame subcomponent 1200 still mounted on the delivery catheter 1504, as shown in FIGS. 6B1-6C2, blood flow may be occluded until which time the leaflet frame subcomponent 1200 is released from the delivery catheter 1504 and/or after the leaflet frame subcomponent 1200 is deployed within the anchor frame subcomponent 1100 and the delivery catheter 1308 removed from the leaflet frame subcomponent 1200.

Figure 5C:
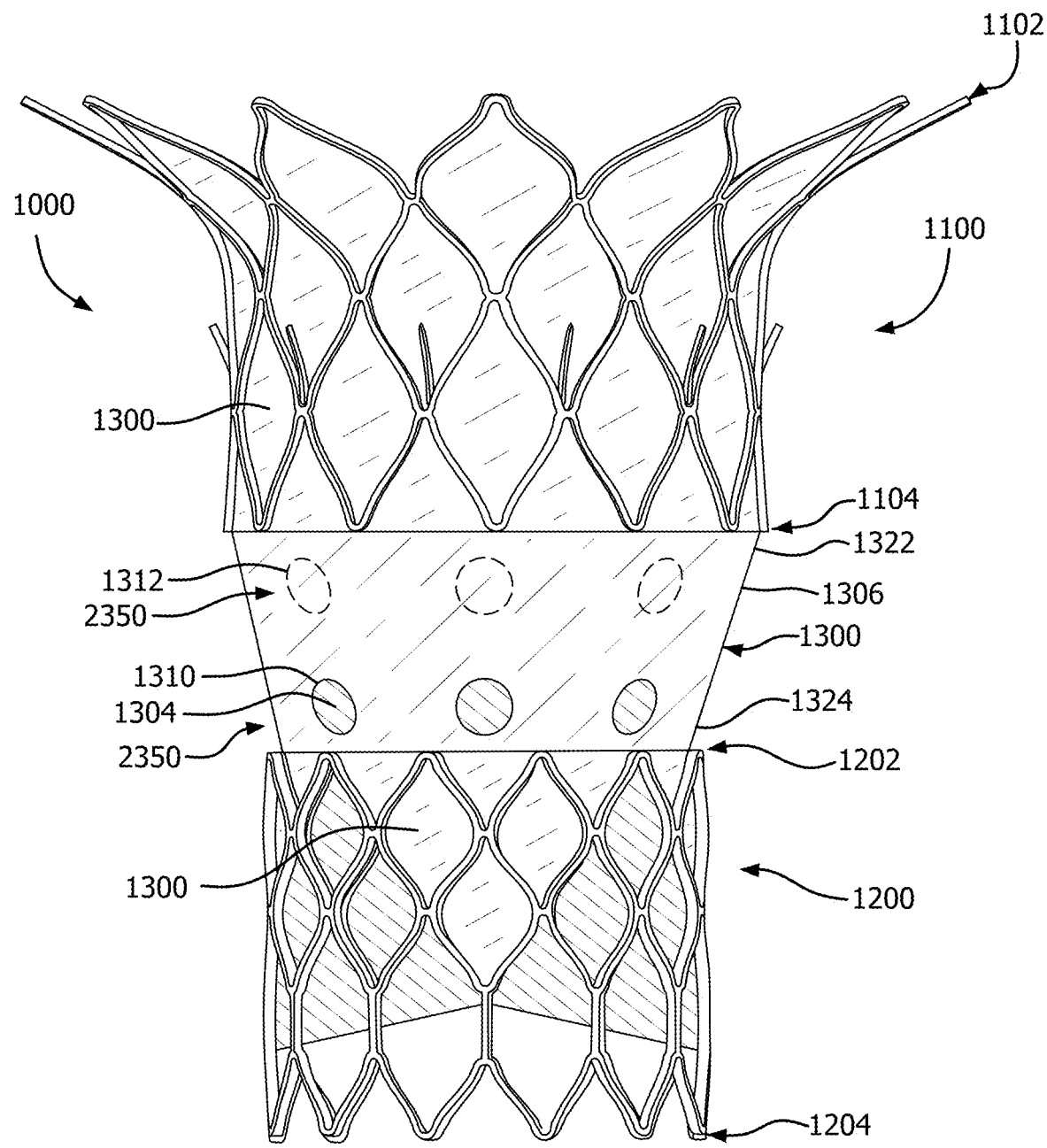
FIG. 5C is a side view of a connecting sheath coupled to a leaflet frame subcomponent and an anchor frame subcomponent including flow enabling features, according to some embodiments.

In various examples, the connecting sheath 1300 is operable to allow antegrade fluid flow, (i.e., blood perfusion) through the connecting sheath wall 1305 during deployment of the prosthetic valve 1000 into the tissue orifice. For example, and with reference to FIGS. 5A-5C and 5E, a prosthetic valve 2000 includes one or more flow enabling features 2350 formed in the connecting sheath 1300 extending between the anchor frame subcomponent 1100 and the leaflet frame subcomponent 1200. FIG. 5A is a side view of the prosthetic valve 2000 with the flow enabling features 2350 in an open configuration where antegrade flow (denoted by arrow "A") is permitted. FIG. 5B is a side view of the prosthetic valve 2000 with the flow enabling features 2350 in a closed configuration where retrograde (denoted by arrow "R") flow is obstructed. In some examples, the one or more flow enabling feature 2350 include one or more perforations or apertures. The flow enabling features 2350 are operable to enable antegrade flow and prevent retrograde flow through the flow enabling features 2350 prior to the anchor frame subcomponent 2100 and the leaflet frame subcomponent 2200 being nested together and in a fully deployed configuration. Further, the flow enabling features 2350 are configured to be fully closed and sealed when the leaflet frame subcomponent 2200 is nested into the anchor frame subcomponent 1100 and in a fully deployed configuration.

In some examples, the one or more flow enabling features 2350 additionally or alternatively include one or more mechanisms that facilitate unidirectional flow. For instance, in some examples, the flow enabling features are configured as one-way valves. In some examples, one-way valves include an aperture or perforation and a flap or element of material that overlays and is larger than the aperture or perforation so as to cover and seal the aperture or perforation under retrograde flow pressure. In some examples, the one-way valve is oriented to permit antegrade flow through the prosthetic valve, while minimizing or preventing retrograde flow through the prosthetic valve.

FIGS. 5A-5E are side views as if the prosthetic valve 1000, as shown in FIG. 4, was unconstrained from a constrained pre-nested configuration in order to more clearly show the particular elements. As shown in FIGS. 5A-5B, an example of flow enabling features 2350 include an aperture 2352 and a flap 2354 that operate to enable antegrade flow through the prosthetic valve 2000 prior to the anchor frame subcomponent 2100 and the leaflet frame subcomponent 2200 being nested together (i.e., while the anchor frame subcomponent 2100 and the leaflet frame subcomponent 2200 are longitudinally offset as illustrated and described herein). The flap 2354 is oversized relative to the aperture 2352 to cover the aperture 2352 under retrograde flow pressure and restrict or minimize retrograde flow through the aperture 2352, while during antegrade flow the flap 2354 lifts away from the aperture 2352 permitting antegrade flow through the aperture 2352. Further, the flap 2354 is configured to cover and seal the aperture 2352 when the leaflet frame subcomponent 2200 is nested into the anchor frame subcomponent 1100 and in a fully deployed configuration.

Figure 5D:
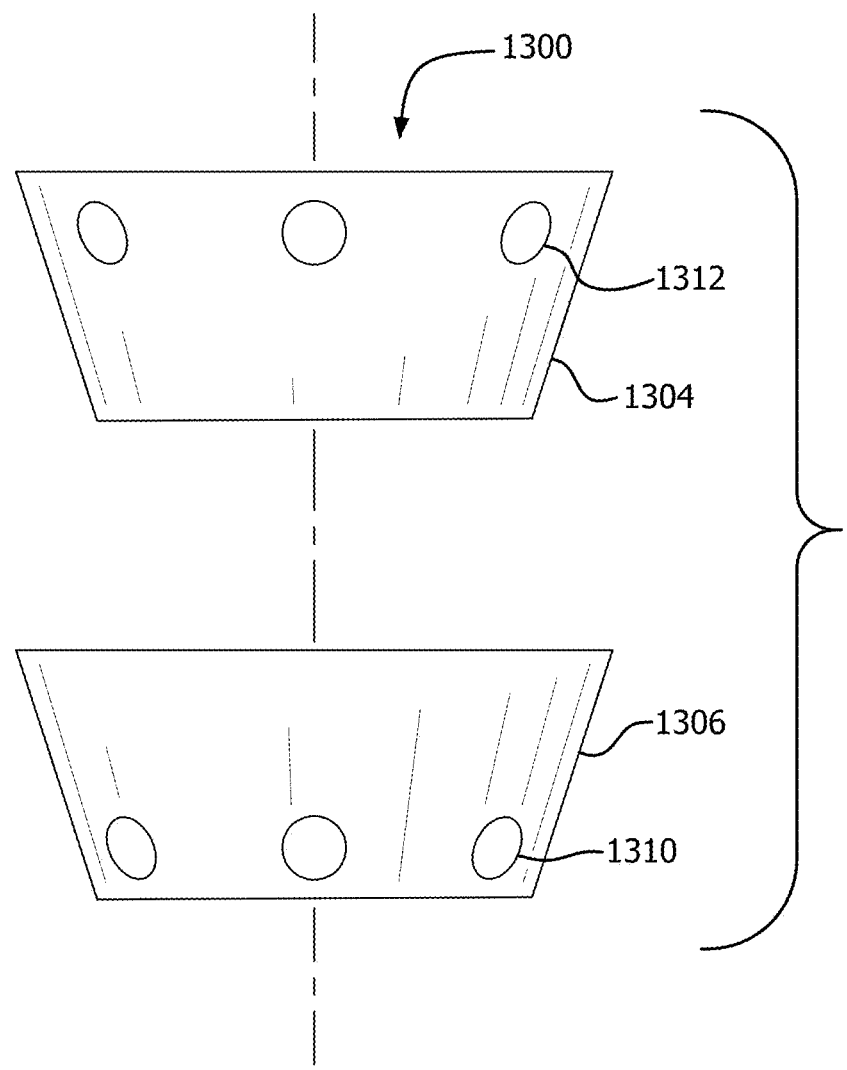
FIG. 5D is an exploded view of the connecting sheath of FIG. 5C.

In some embodiments as will be described below, the connecting sheath 1300 comprises two layers of film, an inner film layer 1304 and an outer film layer 1306 (as shown in FIG. 5C-5D) with both layers coupled to either the inner or outer surface of the anchor frame 1120 and leaflet frame 1220, or the inner film layer 1304 bonded to the inner surfaces of the anchor frame 1120 and leaflet frame 1220 and the outer film layer 1306 coupled to the outer surfaces of the anchor frame 1120 and leaflet frame 1220.

FIG. 5C is a side view of another embodiment of the connecting sheath 1300 as shown coupled to the leaflet frame subcomponent 1200 and anchor frame subcomponent 1100. FIG. 5D is an exploded view of the connecting sheath 1300. In accordance with this embodiment, the connecting sheath 1300 is a double layer of film, an inner film layer 1304 that is a conical tubular member that defines an inner layer of the connecting sheath 1300 and an outer film layer 1306 that is a conical tubular member that is slightly larger than the inner film layer 1304 that defines an outer layer of the connecting sheath 1300 when in the partially deployed configuration shown in FIG. 5C. The inner film layer 1304 and the outer film layer 1306 are coupled together at least at the leaflet frame subcomponent inflow end 1202 of the leaflet frame subcomponent 1200 and the anchor frame subcomponent outflow end 1104 of the anchor frame subcomponent 1100. The inner film layer 1304 defines at least one inner film aperture 1312 therethrough adjacent the anchor frame subcomponent 1100 and the outer film layer 1306 defines at least one outer film aperture 1310 therethrough adjacent the leaflet frame subcomponent 1200. A respective inner film aperture 1312 is offset in the radial direction from a respective outer film aperture 1310 to facilitate operation as provided below. The inner film layer 1304 and the outer film layer 1306 are not coupled at least between one of the inner film apertures 1312 and one of the outer film apertures 1310 so as to define a flow space 1320 therebetween such that the outer film layer 1306 lifts away from the inner film apertures 1312 to enable antegrade flow through the inner film apertures 1312 and the outer film apertures 1310 prior to the anchor frame subcomponent 2100 and the leaflet frame subcomponent 2200 being nested (i.e., while the anchor frame subcomponent 2100 and the leaflet frame subcomponent 2200 are longitudinally offset as illustrated and described herein). The inner film layer 1304 and the outer film layer 1306 come together to close the flow space and to cover and seal the inner film apertures 1312 and outer film apertures 1310 under retrograde flow pressure and restrict or minimize retrograde flow through the inner film apertures 1312 and outer film apertures 1310. Further, the inner film layer 1304 and the outer film layer 1306 are configured to cover and seal the inner film apertures 1312 and outer film apertures 1310 when the leaflet frame subcomponent 2200 is nested into the anchor frame subcomponent 1100 and in a fully deployed configuration.

In the above embodiment, the inner film layer 1304 and the outer film layer 1306 are coupled together at least at the leaflet frame subcomponent inflow end 1202 of the leaflet frame subcomponent 1200 and the anchor frame subcomponent outflow end 1104 of the anchor frame subcomponent 1100. It is appreciated that in accordance with an embodiment, the outer film layer 1306 may not be coupled together at or adjacent to the anchor frame subcomponent outflow end 1104 and still function to cover the inner film aperture 1312 during retrograde flow conditions. A provided in the above embodiment related to the flap 2354, the outer film layer 1306 may function as does the flap 2354; that is to occlude the inner film aperture 1312 during retrograde flow conditions.

Figure 5E:
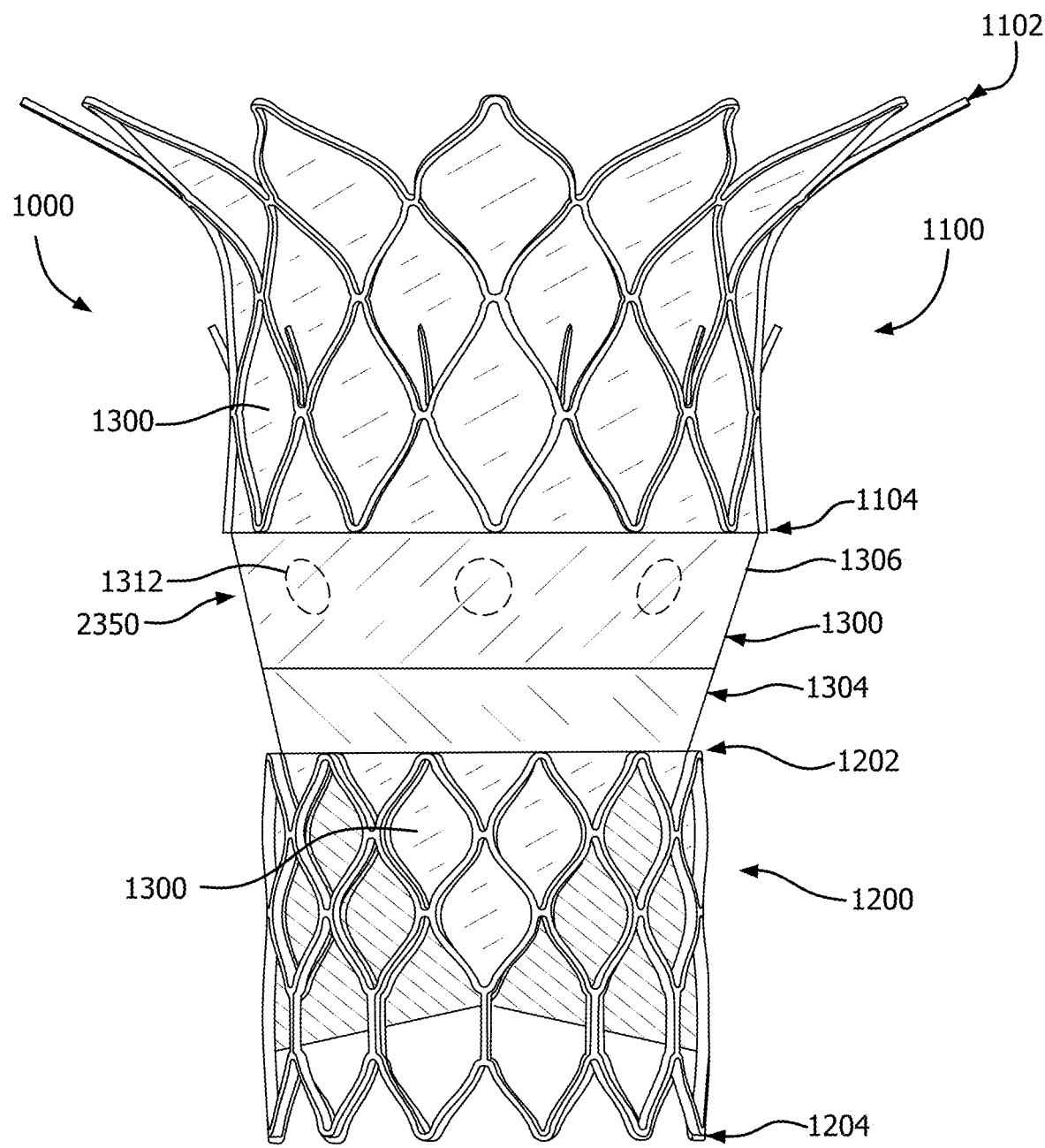
FIG. 5E is a side view of a connecting sheath coupled to a leaflet frame subcomponent and an anchor frame subcomponent including flow enabling features, according to some embodiments.

FIG. 5E is a side view of an embodiment of the connecting sheath 1300 as shown coupled to the leaflet frame subcomponent 1200 and anchor frame subcomponent 1100. In accordance with this embodiment, the connecting sheath 1300 is a double layer of film, an inner film layer 1304 that is a conical tubular member that defines an inner layer of the connecting sheath 1300 and an outer film layer 1306 that is a conical tubular member that is slightly larger but shorter than the inner film layer 1304 that defines an outer layer of the connecting sheath 1300 when in the partially deployed configuration shown in FIG. 5C. The inner film layer 1304 and the outer film layer 1306 are coupled together at least at the anchor frame subcomponent outflow end 1104 of the anchor frame subcomponent 1100 but are not coupled at the leaflet frame subcomponent inflow end 1202 of the leaflet frame subcomponent 1200.

The inner film layer 1304 defines at least one inner film aperture 1312 therethrough adjacent the anchor frame subcomponent 1100 and the outer film layer 1306 is configured to cover the at least one inner film aperture 1312. Under antegrade flow conditions, the outer film layer 1306 lifts away from the inner film layer 1304 and uncovers the at least one inner film aperture 1312 so as to define a flow space 1320 therebetween such that the outer film layer 1306 lifts away from the inner film apertures 1312 to enable antegrade flow through the inner film apertures 1312 prior to the anchor frame subcomponent 2100 and the leaflet frame subcomponent 2200 being nested (i.e., while the anchor frame subcomponent 2100 and the leaflet frame subcomponent 2200 are longitudinally offset as illustrated and described herein). The inner film layer 1304 and the outer film layer 1306 come together to close the flow space and to cover and seal the inner film apertures 1312 under retrograde flow pressure and restrict or minimize retrograde flow through the inner film apertures 1312. Further, the inner film layer 1304 and the outer film layer 1306 are configured to cover and seal the inner film apertures 1312 when the leaflet frame subcomponent 2200 is nested into the anchor frame subcomponent 1100 and in a fully deployed configuration FIG. 6A is a greatly simplified cross-sectional view of a representation of the prosthetic valve 1000 constrained onto a delivery catheter 1504 and placed within a tissue annulus 1342, in accordance with an embodiment. In accordance with the above embodiment, as shown in FIGS. 6B1 and 6B2, while the anchor frame subcomponent 1100 is being deployed within the tissue annulus 1342 and the leaflet frame subcomponent 1200 is translated and nested into the anchor frame subcomponent 1100 in the pre-deployed configuration, whereby everting or folding/rotating the connecting sheath 1300, antegrade flow pressure causes the outer film layer 1306 to move away from the inner film layer 1304 so as to define the flow space 1320 between the inner film layer 1304 and outer film layer 1306. Blood may flow in the antegrade direction into the inner film aperture 1312 and out of the outer film aperture 1310 especially during deployment of the prosthetic valve 1000 when the anchor frame subcomponent 1100 and the still mounted on the delivery catheter leaflet frame subcomponent 1200 are blocking antegrade flow and the leaflets 1230 are not yet functional. In this example, blood profusion may be maintained during substantially the entire deployment process of the prosthetic valve 1000.

Under retrograde flow pressure, blood is prevented from flowing through the flow enabling features 2350 in a retrograde direction. Retrograde flow pressure causes the outer film layer 1306 to move toward and against the inner film layer 1304 so as to close the flow space 1320 between the inner film layer 1304 and outer film layer 1306, with the inner film layer 1304 covering the outer film aperture 1310 and/or the outer film layer 1306 covering the inner film aperture 1312 due to the radial offset of the inner film aperture 1312 and the outer film aperture 1310. Blood is prevented from flowing in the retrograde direction into the outer film aperture 1310 and out of the inner film aperture 1312 especially during deployment of the prosthetic valve 1000 when the deployed anchor frame subcomponent 1100 and the still mounted on the delivery catheter leaflet frame subcomponent 1200 are blocking retrograde flow.

As shown in FIG. 6D the leaflet frame subcomponent 1200 is expanded into its final deployed configuration. The inner film layer 1304 and the outer film layer 1306 are caused to come together under antegrade and retrograde fluid pressure and/or mechanical pressure narrowing or closing the flow space 1320 and with the inner film layer 1304 covering the outer film aperture 1310 and/or the outer film layer 1306 covering the inner film aperture 1312 closing the respective outer film aperture 1310 and inner film aperture 1312 due to the radial offset of the inner film aperture 1312 and the outer film aperture 1310, preventing flow therethrough. In this example, blood profusion may be maintained during substantially the entire deployment process, and with the delivery catheter 1504 removed from the prosthetic valve 1000, the leaflets 1230 become functional.

Retention Element

Referring again to FIGS. 1A-1B3, in various embodiments, the retention element 1400 is operable to position and/or retain the leaflet frame subcomponent 1200 within the anchor frame subcomponent. In accordance with an embodiment, the retention element 1400 is operable to control the axial position of the leaflet frame subcomponent 1200 within the anchor frame subcomponent 1100. In accordance with another embodiment, the retention element 1400 is configured to cover an inflow annular groove formed between the anchor frame subcomponent 1100 and the connecting sheath 1300 which had been everted during the deployment process.

In accordance with an embodiment, the retention element 1400 defines a retention element first end 1403 and a retention element second end 1405. The retention element second end 1405 is coupled to the sheath outflow end 1316 but is not directly coupled to the leaflet frame 1220 at the leaflet frame subcomponent inflow end 1202, there being a portion of the connecting sheath 1300 therebetween. In examples of the retention element 1400, the retention element second end 1405 is coupled only to the connecting sheath 1300 adjacent the leaflet frame subcomponent inflow end 1202 allowing the retention element 1400 to hinge or pivot about the retention element second end 1405. The retention element 1400 is an elongated element that is operable to extend generally parallel to axis X of the prosthetic valve 1000, as shown in FIGS. 1B1-1B3, 6A-6C2, 10D-10F, and 10I, when in the pre-deployed configuration, and operable to extend at an angle, and in some examples, in a generally lateral direction to the axis X when in the deployed configuration, as shown in FIGS. 1C2, 1D, 6D, 7B-7C, and 10J-10K. As shown, the axis X is optionally a central, longitudinal axis of the prosthetic valve 1000. The retention element 1400 is operable to translate through the anchor frame subcomponent 1100 during the deployment process, as shown in FIGS. 6A-6C2 and 10D-10J while the connecting sheath 1300 is operable to fold and evert within the anchor frame subcomponent lumen 1140 of the anchor frame subcomponent 1100 and lie between the leaflet frame subcomponent 1200 and the anchor frame subcomponent 1100.

In accordance with an embodiment, the retention element 1400 comprises a continuous sinuous element 1702. The sinuous element 1702 is configured to have a spring bias toward a planar star-shaped configuration defining elongated elements 1412 bending about apices 1414, as shown in FIGS. 7B-7C. The elongated elements 1412 have an elongated element first end 1402 and an elongated element second end 1404. In the star-shaped configuration, the elongated elements 1412 extend radially with the elongated element first ends 1402 and respective apices 1414 defining an inner circumference 1422 at a retention element first end 1403 and the elongated element second ends 1404 and respective apices 1414 defining an outer circumference 1424 at a retention element second end 1405. The sinuous element 1702 is operable to be elastically restrained to a tubular configuration wherein the elongated elements 1412 are rotated about the apices 1414 at the elongated element first ends 1402 such that the elongated element second ends 1404 are rotated toward each other to define a tubular or conical configuration. With the sinuous element 1702 defining a first tubular diameter, the tubular diameter may be further reduced by bringing the elongated elements 1412 into closer arrangement while bending at the apices 1414; that is, the elongated elements 1412 extend laterally to the axis X and along the connecting sheath 1300 and lateral with the anchor frame subcomponent 1100 and leaflet frame subcomponent 1200 as shown in FIG. 1A.

The sinuous element 1702 may be restrained to define a small tubular diameter in the constrained pre-deployment configuration at relatively the same diameter as that of the constrained leaflet frame subcomponent 1200 and the constrained anchor frame subcomponent 1100 and extending therebetween, with the retention element 1400 within the connecting sheath lumen 1340, as shown in FIG. 1A. The connecting sheath 1300 may be folded and/or pleated to facilitate reduction to a smaller diameter. In the deployed configuration, the retention element first end 1403 of the sinuous element 1702 retains substantially the same diameter as the expanded leaflet frame subcomponent 1200, wherein the elongated element second ends 1404 flare away from the elongated element first ends 1402 to define substantially the diameter of the anchor frame subcomponent inflow end 1102, bridging the distance between the leaflet frame subcomponent inflow end 1202 and the anchor frame subcomponent inflow end 1102 and extending across an inflow annular groove 1704 defined by the anchor frame subcomponent inflow end 1102 and the connecting sheath 1300. The retention element first end 1403 is coupled to and restrained by the connecting sheath outflow end 1324. The retention element second end 1405 may be restrained by a retention means 1710 such as a lasso 1712, noose, tether element 1714, draw string, removable clip, or other restraining element whether on the prosthetic valve 1000 or on a delivery device, as shown in FIGS. 6I-6K, 7A.

The retention element 1400 is operable to retain the relative position of the leaflet frame subcomponent 1200 and the anchor frame subcomponent 1100 by virtue of the spring bias of the sinuous element 1702 resisting forces in opposition to the retention element 1400 being biased to a planar configuration. Spring bias forces may be predetermined such that fluid dynamic forces on the prosthetic valve 1000 are not sufficient to overcome the spring bias needed to bend the elongated elements 1412 to a tubular configuration which would lead to the leaflet frame subcomponent 1200 moving an unacceptable distance axially within the anchor frame subcomponent lumen 1140 and maintain a relative axial position (or at least minimize relative axial movement) between the anchor frame subcomponent 1100 and the leaflet frame subcomponent 1200.

It is understood that the retention element 1400 may be provided with a predetermined spring bias, such that the retention element 1400 is operable as a shock absorber, to allow a predetermined amount of movement of the leaflet frame subcomponent 1200 during the operation of the prosthetic valve 1000. Such predetermined amount of movement may reduce stresses within various components of the prosthetic valve 1000, such as, but not limited to, the leaflets or other valve structures.

In accordance with embodiments, a non-permeable cover 1432 is coupled to the sinuous element 1702 such that fluid is prevented from passing through the retention element 1400 when in the deployed configuration, as shown in FIGS. 7B-7C. The cover 1432 extends from the apices 1414 at the elongated element first ends 1402 of the elongated elements 1412 to the apices 1414 at the elongated element second ends 1404. In the deployed configuration, the cover 1432 extends from the leaflet frame subcomponent inflow end 1202 to the anchor frame subcomponent inflow end 1102 effectively covering the inflow annular groove 1704 formed between the anchor frame subcomponent 1100 and the connecting sheath 1300.

It is desired to cover or seal off the inflow annular groove 1704 from blood flow for various reasons. In accordance with an embodiment, covering the inflow annular groove 1704 provides a smoother flow into the leaflet frame subcomponent inflow end 1202 of the leaflet frame subcomponent 1200 compared with flow that would otherwise flow antegrade into and retrograde out of the inflow annular groove 1704. Further, covering the inflow annular groove 1704 might prevent embolus that might be formed within the inflow annular groove 1704 from being dislodged and flow through the prosthetic valve 1000.

Manual Deployment

In accordance with embodiments, the retention element 1400 is advanced through the anchor frame subcomponent 1100 while in a compressed configuration constrained to the delivery catheter 1504 by withdrawing the delivery catheter 1504 upon which the retention element 1400 is mounted. The retention element 1400 is subsequently deployed when positioned adjacent to the anchor frame subcomponent inflow end 1102. In accordance with an example, a tether element 1714 is coupled to the retention element 1400, such as at the retention element second end 1405 of the retention element 1400, such that an operator may pull the tether element 1714 to affect advancement of the retention element 1400 through the anchor frame subcomponent 1100. The retention element second end 1405 of the retention element 1400 may be held in a compressed state by a predetermined amount of tension on the tether element 1714. Tension of the tether element 1714 may be released and thus release the elongated element second end 1404 of the retention element 1400 so as to allow expansion and deployment of the retention element 1400.

In accordance with an example, the leaflet frame subcomponent 1200 is nested and deployed within the anchor frame subcomponent 1100 prior to the deployment of the retention element 1400. In another example, the retention element 1400 is deployed before the deployment of the leaflet frame subcomponent 1200 with in the anchor frame subcomponent 1100. In accordance with another example, the leaflet frame subcomponent 1200 and the retention element 1400 are deployed simultaneously.

Although various examples include one or more of the anchor frame 1120, flange or flared portion 1130, leaflet frame 1220, and/or retention element 1400 being discrete, separate components that are directly or indirectly coupled together, it should be understood that various examples also include one or more (e.g., all of) the anchor frame 1120, flange or flared portion 1130, leaflet frame 1220, and retention element 1400 being formed as an integral unit (e.g., cut or formed from a single tube of material).

Passive Deployment

In accordance with other embodiments, after deployment or expansion of the anchor frame subcomponent 1100 into the tissue annulus, the connecting sheath 1300 presents a tapered configuration having a smaller diameter at the leaflet frame subcomponent inflow end 1202 to a larger diameter at the anchor frame subcomponent outflow end 1104. The retention element 1400 may be released or deployed while still within the connecting sheath 1300, wherein the apices 1414 at the retention element second end of the retention element 1400 may abut and slide along the taper of the connecting sheath inner surface 1314 of the connecting sheath 1300, as shown in FIGS. 1C1, 1C2 and 6G, and subsequently the anchor frame subcomponent inner surface 1107 of the anchor frame subcomponent 1100 while expanding under spring bias, until the apices 1414 at the retention element second end are fully expanded about the anchor frame subcomponent inflow end 1102 of the anchor frame subcomponent 1100. The spring bias may be configured such that sufficient force is produced to advance the retention element 1400 through the taper of the connecting sheath 1300 and the anchor frame subcomponent inner surface 1107 of the anchor frame subcomponent 1100 toward the anchor frame subcomponent inflow end 1102 while pulling the leaflet frame subcomponent 1200 into the anchor frame subcomponent 1100. In accordance with embodiments, the leaflet frame subcomponent 1200 may be either retained on the delivery catheter 1504 or deployed to the expanded configuration prior to being pulled into the anchor frame subcomponent 1100. In this embodiment, release of the constrained retention element 1400 allows for a passive means for advancing the leaflet frame subcomponent 1200 into the anchor frame subcomponent 1100, that is, the operator does not need to manipulate the position of the delivery catheter 1504 during deployment of the leaflet frame subcomponent 1200.

In accordance with another embodiment, the length of the retention element 1400 is predetermined such that the apices 1414 at the retention element second end 1405 of the retention element 1400 extend within the anchor frame subcomponent 1100 while in the pre-deployed configuration. When deployed, the apices 1414 at the retention element second end 1405 may abut and slide along the anchor frame subcomponent inner surface 1107 of the anchor frame subcomponent 1100 while expanding under spring bias, until the apices 1414 at the retention element second end 1405 are fully expanded about the anchor frame subcomponent inflow end 1102. The spring bias may be configured such that sufficient force is produced to advance the retention element 1400 through the anchor frame subcomponent 1100 toward the anchor frame subcomponent inflow end 1102 while pulling the leaflet frame subcomponent 1200 into and nesting the anchor frame subcomponent 1100. In accordance with embodiments, the leaflet frame subcomponent 1200 may be either retained on the delivery catheter 1504 or deployed to the expanded configuration prior to being pulled into and nested in the anchor frame subcomponent 1100. In this embodiment, release of the constrained retention element 1400 allows for a passive means for advancing the leaflet frame subcomponent 1200 into the anchor frame subcomponent 1100, that is, the operator does not need to manipulate the position of the delivery catheter 1504 during deployment of the leaflet frame subcomponent 1200.

As will be discussed below, the delivery device may incorporate elements to facilitate the advancement and deployment of the anchor frame subcomponent 1100, the leaflet frame subcomponent 1200, and the retention element 1400. In accordance with embodiments, the advancement of the leaflet frame subcomponent 1200, and the retention element 1400 into the anchor frame subcomponent 1100 is facilitated by moving or staged withdraw of the delivery catheter. In accordance with other embodiments, the advancement of the leaflet frame subcomponent 1200 and the retention element 1400 into or through, respectively, the anchor frame subcomponent 1100 is facilitated by moving internal components of the delivery catheter 1504, such as, but not limited to the leaflet frame subcomponent 1200 riding on a trolley advanced by a pulling of a tether element 1714 or by spring bias of the retention element 1400 or an internal component of the delivery device. An embodiment of a sliding trolley may be a larger diameter tubular member operable to be slidingly received onto a smaller diameter delivery catheter 1504. The trolley may be constrained from sliding on the delivery catheter 1504 by a retention means, such as, but not limited to, a tether element 1714 or a latch.

LVOT Taper

Referring again to the anchor frame subcomponent 1100, as shown in FIGS. 1B1-1B3, the length of the anchor frame 1120 and thus the anchor frame subcomponent 1100, is predetermined for a particular purpose. In accordance with embodiments, the length of the anchor frame 1120 is predetermined based on, among other things, the anatomy of the tissue annulus into which the prosthetic valve 1000 is implanted, including, but not limited to, the shape of the annulus, the amount of tissue available to support the anchor frame subcomponent 1100, the proximity with flow paths, other tissues, and nerves, and the structural characteristics of the anchor frame subcomponent (urging engagement spring bias or plastic deformation hoop strength, fixation barbs, proper compliance, reforming/reshaping).

Figure 8A:
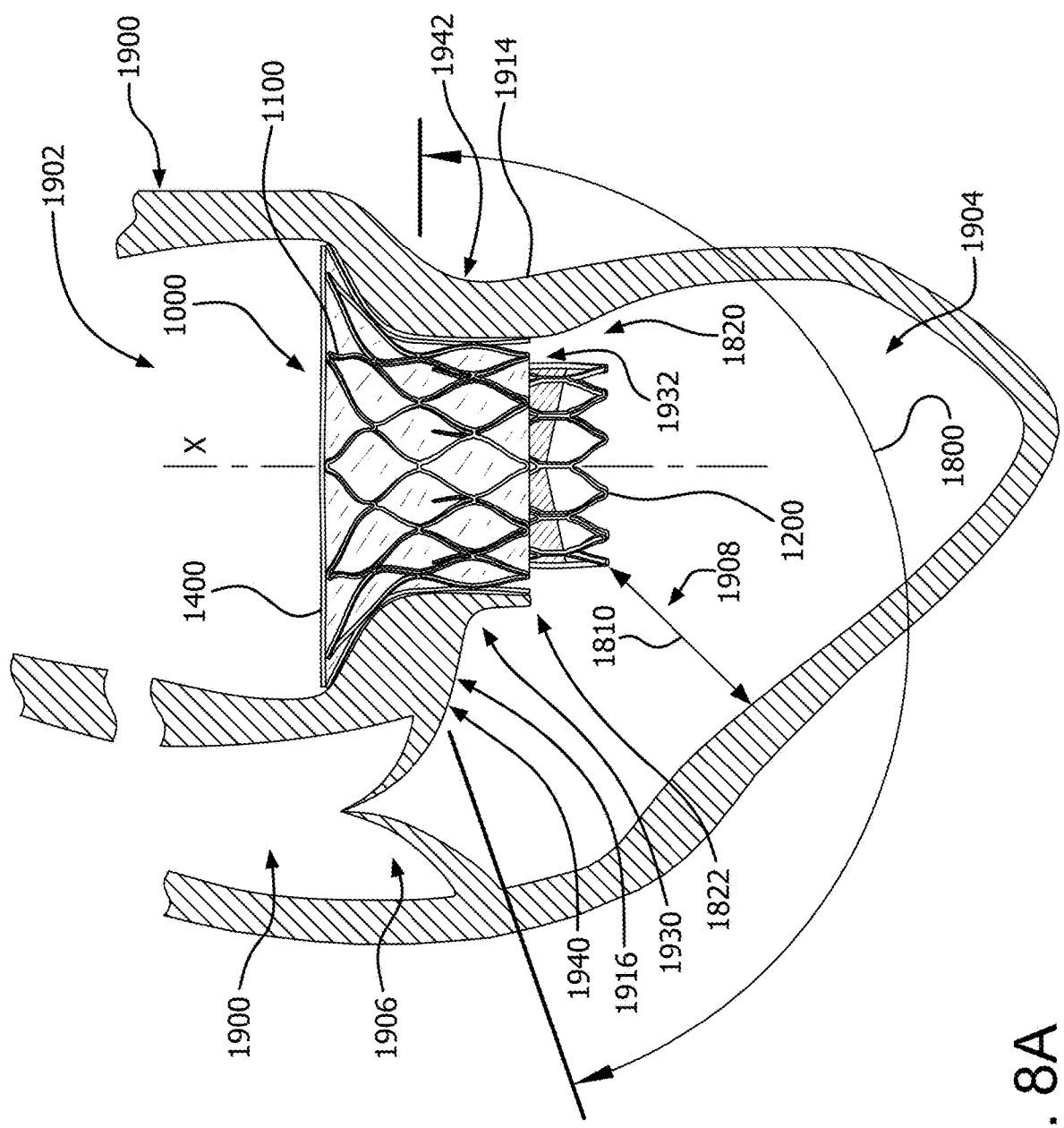
FIG. 8A is partial cross-sectional view of a prosthetic valve deployed in an anatomy with a larger aortomitral angle with an anchor frame having a constant length along a circumference, according to some embodiments.
Figure 8B:
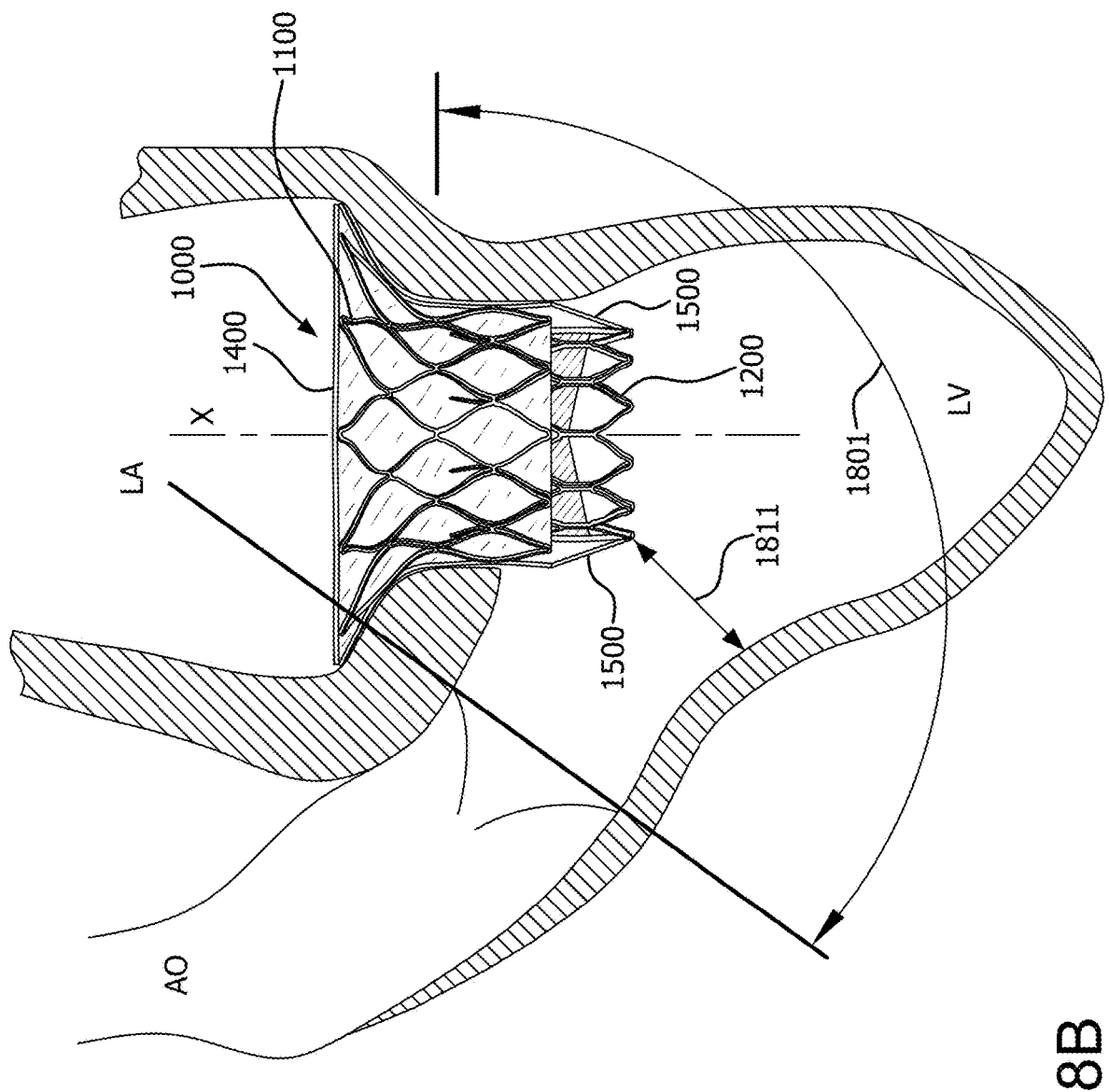
FIG. 8B is partial cross-sectional view of a prosthetic valve deployed in anatomy with a smaller aortomitral angle with an anchor frame having a constant length along a circumference, according to some embodiments.
Figure 8C:
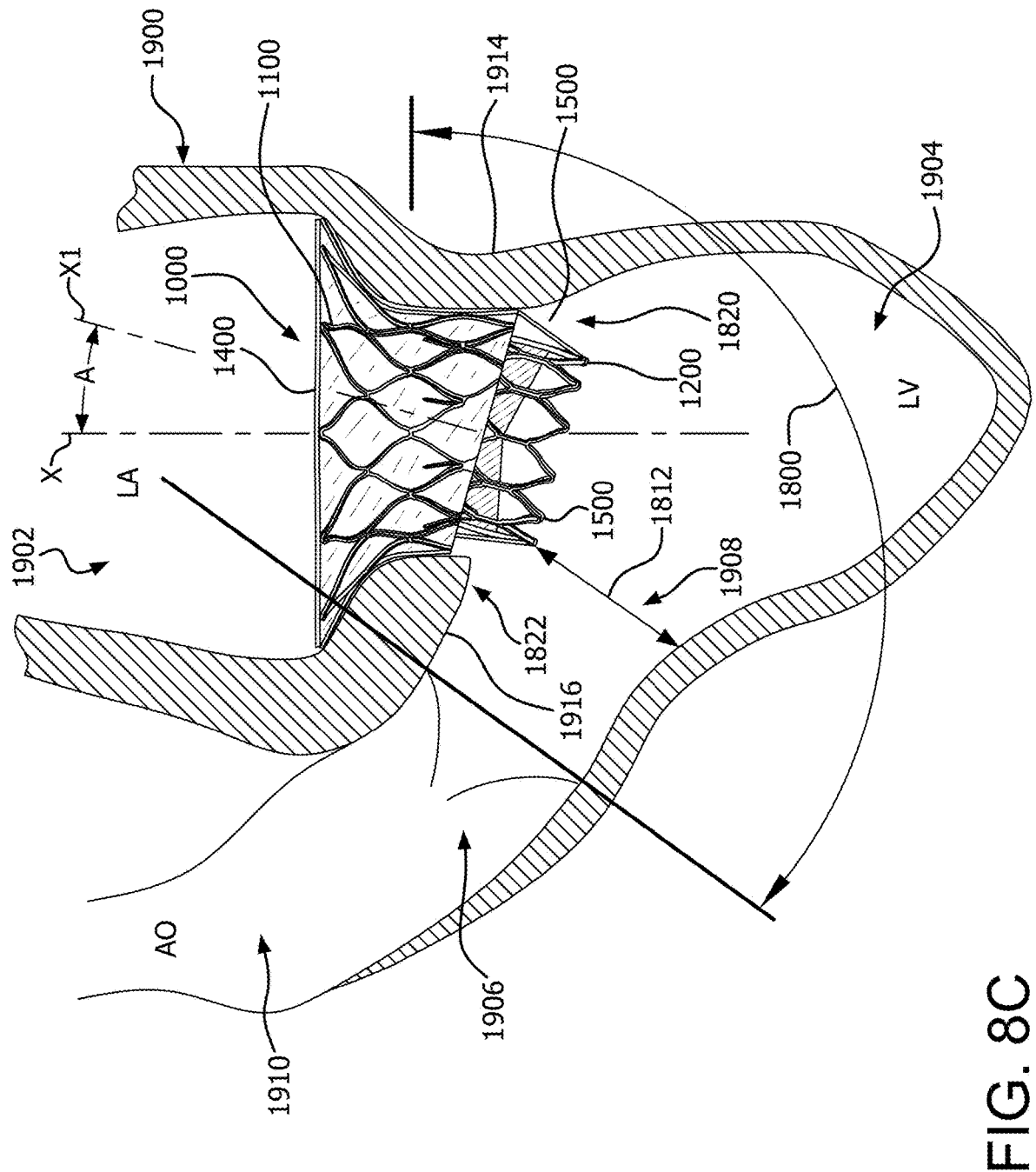
FIG. 8C is partial cross-sectional view of a prosthetic valve deployed in anatomy with a smaller aortomitral angle with an anchor frame having a variable length along a circumference, according to some embodiments

FIG. 8A is a cross-sectional view of the heart and the prosthetic valve 1000 deployed within a tissue annulus of a mitral valve. In accordance with embodiments, the length of the anchor frame subcomponent 1100 is the uniform along its circumference. In other embodiments, the length of the anchor frame subcomponent 1100 varies along the circumference, for example, when viewed transverse to the axis X, the anchor frame subcomponent outflow end 1104 has a tapered geometry, as shown in FIG. 8C. By way of example, discussion of the mitral valve anatomy follows with the application of the prosthetic valve 1000 being used to replace a mitral valve 1920 (obscured and deformed by the prosthetic valve 1000). Referring to FIG. 8A, the mitral valve 1920 is a one-way valve that allows blood flow from the left atrium 1902 to the left ventricle 1904. Blood leaves the left ventricle 1904 through the aortic valve 1906 and into the aorta 1910. Immediately before the aortic valve 1906, the anatomy defines the left ventricular outflow tract (LVOT) 1908, a conduit though which blood enters the aortic valve 1906. Cardiac output is directly related to the smallest diameter of the LVOT 1908 to permit the flow of blood to the aortic valve 1906. An LVOT 1908 that is reduced in diameter or restricted by tissue or an implanted device reduces cardiac output and can lead to debilitating cardiac function. Therefore, minimizing the blocking of the LVOT 1908 by the prosthetic valve 1000 is imperative.

The mitral valve 1920 and the aortic valve 1906 are adjacent each other and form an aortomitral angle 1800 relative to their transverse axes, which can vary between patients. One can see from FIG. 8A that where the aortomitral angle 1800 is much greater than 90 degrees and approaching 180 degrees, the degree of interference of the anchor frame subcomponent 1100 extending into the LVOT 1908 is less than if the aortomitral angle is closer to 90 degrees, as shown in FIG. 8B. As the aortomitral angle approaches 90 degrees, the extension of an anchor frame subcomponent anterior portion 1822 of the anchor frame subcomponent outflow end 1104 of the anchor frame subcomponent 1100 of a given constant length into the LVOT 1908 becomes greater.

In accordance with an embodiment of the prosthetic valve 1000 for mitral valve replacement, the length of the anchor frame subcomponent 1100 is determined by considering one or more of at least the following parameters: the aortomitral angle 1800, and the degree of obstruction or blockage by the prosthetic valve 1000 of the LVOT 1908, the dimensions of the tissue annulus 1930 and the amount of tissue available for engagement with the prosthetic valve 1000. In accordance with an embodiment, to minimize blockage of the LVOT 1808 for smaller aortomitral angles 1800, the length of the anchor frame subcomponent 1100 varies along its circumference, for example, when viewed transverse to the axis X, the anchor frame subcomponent outflow end 1104 has a tapered geometry. The anchor frame subcomponent outflow end 1104 is tapered such that the anchor frame subcomponent outflow end 1104 extends further into the left ventricle 1904 adjacent to a posterior side 1914 of the left ventricle 1904 and extends less into the LVOT 1908 on the anterior side 1916 of the left ventricle 1904.

As shown in FIG. 8C, the length of the anchor frame subcomponent 1100 varies along the circumference, for example, when viewed transverse to the axis X, the anchor frame subcomponent outflow end 1104 has a tapered geometry, in some embodiments. As shown, the anchor frame subcomponent 1100 can be oriented along the X-axis and the leaflet frame subcomponent 1200 can be oriented along the X1-axis which is off-set to the X-axis. FIG. 8C shows an embodiment in which "off-set" can refer to an arrangement wherein the X1-axis can be angled from the X1-axis (e.g., the X-axis and the X1-axis are non-collinear or non-parallel) such that the leaflet frame subcomponent 1200 is generally tilted with respect to the anchor frame subcomponent 1100. In one embodiment, the second longitudinal axis is disposed at a tilt angle A between 15° and 45° relative to the first longitudinal axis. In another embodiment, the leaflet frame subcomponent outflow end 1204 is generally parallel with the anchor frame subcomponent outflow end 1104, wherein the anchor frame subcomponent outflow end 1104 has a taper as characterized as having a length that varies around the circumference. In this orientation, the extension of the leaflet frame subcomponent outflow end 1204 into the LVOT is reduced as compared with a coaxial anchor frame subcomponent 1100 and leaflet frame subcomponent 1200, as shown in FIG. 8B.

It has been found that fixation of the anchor frame subcomponent 1100 may be greater on the anchor frame subcomponent anterior portion 1822 of the prosthetic valve 1000 adjacent the aortic valve 1906, that is the anterior side 1916 of the left ventricle 1904, as compared with the anchor frame subcomponent posterior portion 1932 of the prosthetic valve 1000 adjacent the posterior side 1914 of the left ventricle 1904. In such a case, the prosthetic valve 1000 may want to preferentially pivot about the anchor frame subcomponent anterior portion 1822. The taper as described above having more extension and tissue engagement with the posterior side 1914 of the left ventricle 1904, will act to further resist the movement of the anchor frame subcomponent posterior portion 1932 of the prosthetic valve 1000. Fluid pressure in the left ventricle 1904 acting on the closed leaflets of the prosthetic valve 1000 will tend to provide a camming force to further engage the anchor frame subcomponent posterior portion 1932 with the posterior side 1914 of the left atrium 1902.

Anchor Frame Variable Stiffness

In accordance with other embodiments, the hoop strength of the anchor frame subcomponent 1100 can be relatively invariable along the length and circumference of the anchor frame 1120. In accordance with other embodiments, the hoop strength of the anchor frame subcomponent 1100 can be variable along the length and/or the circumference of the anchor frame 1120. By way of example and in reference to the anatomy of the mitral valve tissue annulus 1930, the tissue at the aortomitral junction 1940 side of the tissue annulus 1930 may be stiffer than the annulus posterior side 1942 of the tissue annulus 1930. The variable stiffness of the anchor frame 1120 may be predetermined to have a greater stiffness at the smaller tapered portion of the anchor frame subcomponent anterior portion 1822 of the anchor frame subcomponent outflow end 1104 to match the stiffness of the aortomitral junction 1940, as shown in FIG. 8A, whereas the stiffness may be relatively less at the longer prosthetic valve posterior portion 1820 adjacent the posterior side 1914 of the left ventricle 1904.

Retrieval

In accordance with another embodiment, during a transcatheter procedure, the prosthetic valve 1000 is operable to be removable after deployment of the anchor frame subcomponent 1100 but before deployment of the leaflet frame subcomponent 1200 into the anchor frame subcomponent 1100. In accordance with an embodiment, the anchor frame subcomponent 1100 has a predetermined flexibility such that the anchor frame subcomponent 1100 may be everted into the anchor frame subcomponent lumen 1110. In an embodiment, the bending of the anchor frame subcomponent 1100 during eversion occurs along the length of the anchor frame 1120, such that the anchor frame subcomponent 1100 peels away from the tissue annulus 1342, as shown in FIG. 9C1. In accordance with another embodiment, a portion of the anchor frame subcomponent 1100 may pivot and compress about a location adjacent to the anchor frame subcomponent inflow end 1102, such as at the flared portion 1130, such that the anchor frame subcomponent 1100 may pivot or fold inwardly into the anchor frame subcomponent lumen 1110 and be drawn out of the anchor frame subcomponent lumen 1110 having been everted, as shown in FIG. 9C2.

In accordance with a method of retrieving the prosthetic valve 1000, a distal end of a retrieval sheath 1950 is positioned adjacent to the anchor frame subcomponent inflow end 1102 of the prosthetic valve 1000. The retrieval sheath 1950 is an elongated tubular member, such as a catheter, that defines a retrieval sheath lumen 1952 operable to receive the at least partially compressed prosthetic valve 1000. The leaflet frame subcomponent 1200 is reduced in diameter if fully deployed within the anchor frame subcomponent lumen 1110 by use of a retraction means 1956, such as a noose, tether, or the like to a diameter small enough to enter the retrieval sheath lumen 1952. The retracting means 1956 extends from the retrieval sheath lumen 1952 and is operable to pull the prosthetic valve 1000 into the retrieval sheath lumen 1952.

Figure 9A:
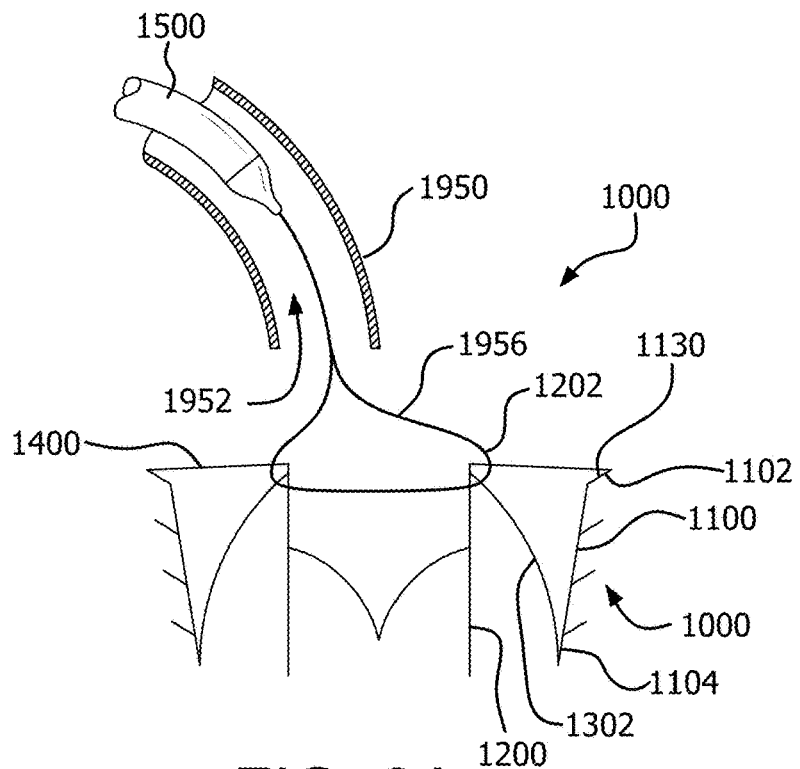
FIG. 9A is a highly simplified side partial cross-sectional representation of a prosthetic valve in a deployed configuration with a retrieval means illustrating an exemplary prosthetic valve retrieval procedure, according to some embodiments.
Figure 9B:
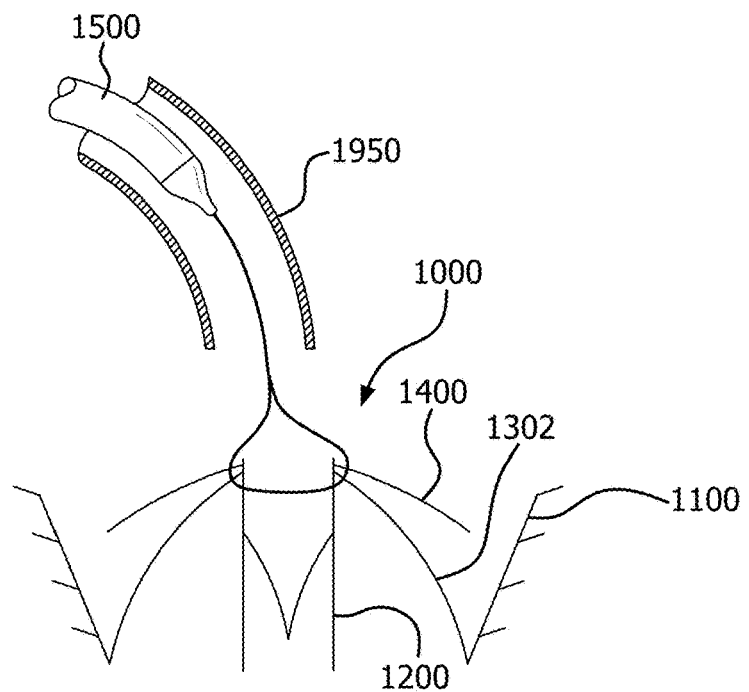
FIG. 9B is a highly simplified side partial cross-sectional representation of the prosthetic valve of FIG. 9A in a partially compressed configuration with a retrieval means illustrating an exemplary prosthetic valve retrieval procedure, according to some embodiments.
Figure 9D:
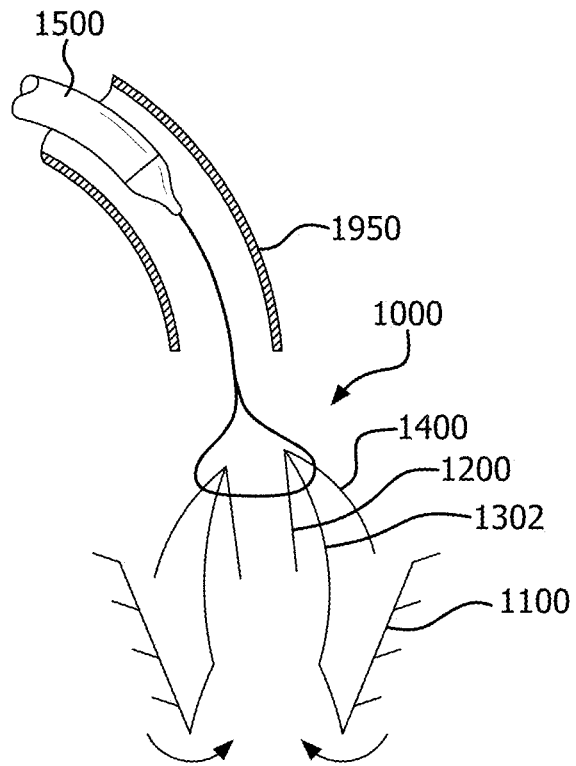
FIG. 9D is a highly simplified side partial cross-sectional representation of the prosthetic valve of FIG. 9A in a compressed deconstructed configuration within a retrieval sheath illustrating an exemplary prosthetic valve retrieval procedure, according to some embodiments.
Figure 9D:
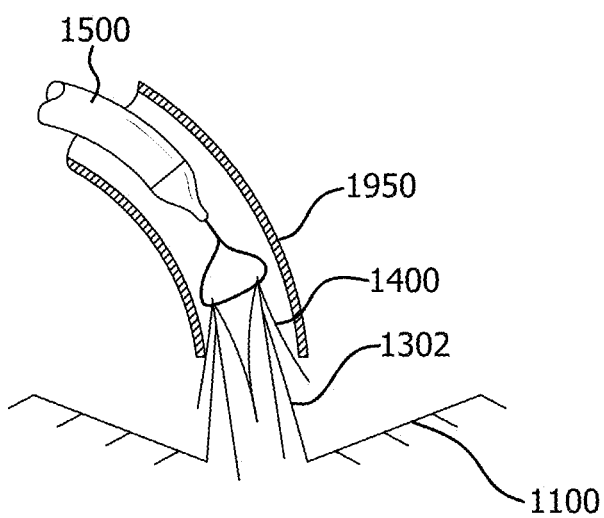
Figure 9D:
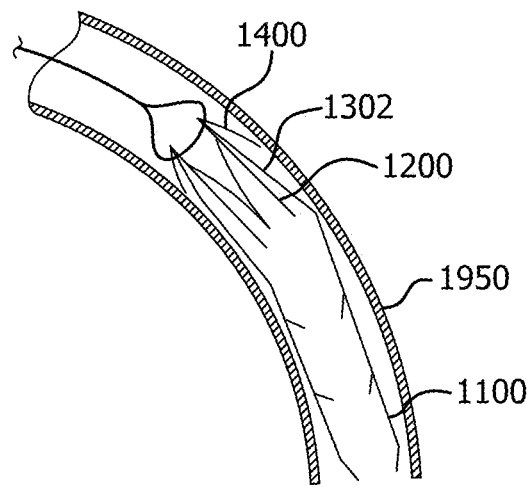

The leaflet frame subcomponent 1200 is reduced in diameter and pulled into the retrieval sheath lumen 1952 by the retraction means 1956, as shown in FIG. 9A. As the leaflet frame subcomponent 1200 and the connecting sheath 1300 is pulled into the retrieval sheath lumen 1952, the anchor frame subcomponent 1100 is pulled away from the tissue annulus 1930. In an embodiment, the bending of the anchor frame subcomponent 1100 during eversion occurs along the length of the anchor frame 1120, such that the anchor frame subcomponent 1100 peels away from the tissue annulus 1342, as shown in FIG. 9B1. In accordance with another embodiment, a portion of the anchor frame subcomponent 1100 may pivot and compress about a location adjacent to the anchor frame subcomponent inflow end 1102, such as at the flared portion 1130, such that the anchor frame subcomponent 1100 may pivot or fold inwardly into the anchor frame subcomponent lumen 1110 and be drawn out of the anchor frame subcomponent lumen 1110 having been everted, as shown in FIG. 9B2. The anchor frame subcomponent 1100 is operable to compress to a smaller diameter to be received within the retrieval sheath lumen 1952 as shown in FIGS. 9A-9D.

It is appreciated that the anchor frame subcomponent 1100 may further comprises tissue engagement features 1118, as shown in FIGS. 1B1-1B3. In consideration of retrieval, the tissue engagement features 1118 are operable to minimize trauma as they are pulled from the tissue annulus 1930 during retrieval. In accordance with an embodiment, the tissue engagement features 1118 have a predetermined angle to the axis X such that when the anchor frame subcomponent 1100 is everted, the tissue anchors will radially extract from the tissue annulus.

Outflow Annular Groove Cover

FIG. 7D3 is a side view of an embodiment of a prosthetic valve 1000 in an expanded pre-deployed configuration. In various examples of the prosthetic valve 1000, when in the deployed configuration, an outflow annular groove is defined by the leaflet frame subcomponent 1200 and the connecting sheath, as shown in FIG. 7D1. FIG. 7D1 is a simplified side cross-sectional view along cut line 7D2 of the prosthetic valve 1000 of FIG. 7D3 in a deployed configuration as shown by way of example in FIG. 7C, but further comprising an outflow annular groove cover 1440. The outflow annular groove cover 1440 is an annular element that is coupled to and extends from a leaflet frame cover outflow edge 1233 of the leaflet frame subcomponent outflow end 1204 to the anchor frame subcomponent outflow end 1104 effectively covering the outflow annular groove 1706 formed between the connecting sheath 1300 and the leaflet frame subcomponent 1200 and closing the volume defined by the leaflet frame cover 1232 of the leaflet frame subcomponent 1200, the connecting sheath 1300, and the outflow groove cover 1432. In accordance with another embodiment, the outflow groove cover 1432 extends between the leaflet frame subcomponent outflow end 1204 and the anchor frame subcomponent outflow end 1104 such that fluid is prevented from entering into an outflow annular groove 1706.

It is desired to cover or seal off the outflow annular groove 1706 from blood flow for various reasons. In accordance with an embodiment, covering the outflow annular groove 1706 provides a smoother flow at the leaflet frame subcomponent outflow end 1204 of the leaflet frame subcomponent 1200 compared with flow that would otherwise flow antegrade into and retrograde out of the outflow annular groove 1706. Further, covering the outflow annular groove 1706 might prevent embolus that might be formed within the outflow annular groove 1706 from being dislodged and flow downstream of the prosthetic valve 1000.

In various embodiments, the outflow annular groove cover 1440 may assist with maintaining the relative positioning of the leaflet frame subcomponent 1200 within the anchor frame subcomponent 1100 when the prosthetic valve 1000 is fully deployed. For example, the outflow annular groove cover 1440 may be resiliently retractable and extendible, such that the outflow annular groove cover 1440 is able to be transitioned between extended and retracted configurations.

The outflow annular groove cover 1440 can present from the extended configuration to the retracted configuration during nesting and expansion of the leaflet frame subcomponent 1200 within the anchor frame subcomponent 1100 such that the outflow annular groove cover 1440 takes on relatively flatter shapes as the outflow annular groove cover 1440 contracts. For example, the outflow annular groove cover 1440 may have an angular wall that is defined as the outflow annular groove cover 1440 contracts and angulates as it transitions from a lower angle (shallower angle) relative to a longitudinal axis X of the prosthetic valve 1000 to a higher angle (steeper angle) relative to the longitudinal axis X of the prosthetic valve 1000. In some examples, the outflow annular groove cover 1440 extends approximately perpendicularly between the walls of the leaflet frame subcomponent 1200 and the anchor frame subcomponent 1100 in the retracted configuration. In some examples, the outflow annular groove cover first end 1444 can be coupled to the anchor frame subcomponent outflow end 1104 and the outflow annular groove cover second end 1442 can be coupled to the leaflet frame subcomponent outflow end 1204.

In the deployed, or retracted configuration, the outflow annular groove cover 1440 extends between the leaflet frame subcomponent outflow end 1204 and the anchor frame subcomponent outflow end 1104 with the outflow annular groove cover 1440 operable to cover and restrict fluid flow into, or out from, the outflow annular groove 1706. In various embodiments of the prosthetic valve 1000 that include flow enabling features 2350 as shown in FIGS. 5A-E, the outflow annular groove cover 1440 is required to be permeable to fluid when the prosthetic valve is in the pre-deployed configuration so at to allow fluid to pass through the flow enabling features. In accordance with an embodiment, the outflow annular groove cover 1440 is less permeable to blood (e.g., blood impermeable under physiologic conditions) when in the retracted configuration wherein the prosthetic valve 1000 is in the deployed configuration. The outflow annular groove cover 1440 may be configured to be blood permeable under physiologic conditions when in the extended configuration wherein the prosthetic valve 1000 is in the pre-deployed configuration. For example, after initiation, but prior to completion of transitioning the prosthetic valve 1000 to a fully deployed configuration the outflow annular groove cover 1440 is configured to be blood permeable.

In various examples, the outflow annular groove cover 1440 is a flexible elastic element that is operable to resiliently stow into a low radial profile in a delivery configuration and is operable to extend between the leaflet frame subcomponent 1200 and the anchor frame subcomponent 1100. The outflow annular groove cover 1440 can be implemented to inhibit flood flow into or out from between the anchor frame subcomponent 1100 and the leaflet frame subcomponent 1200.

In some examples, the outflow annular groove cover 1440 is under elastic bias when in a deployed position such that they are held relatively taught. Engagement of the outflow annular groove cover 1440 with the anchor frame subcomponent 1100 and the leaflet frame subcomponent 1200 may assist in maintaining the relative position of the leaflet frame subcomponent 1200 within an anchor frame subcomponent lumen 1140, according to some embodiments.

As shown in FIGS. 7D1-7D3, the outflow annular groove cover 1440 defines an outflow annular groove cover first end 1444 and an outflow annular groove cover second end 1442. The outflow annular groove cover first end 1444 is coupled to the anchor frame subcomponent outflow end 1104. The outflow annular groove cover second end 1442 is coupled to the leaflet frame subcomponent 1200 about the leaflet frame cover outflow edge 1233 of the leaflet frame cover 1232 adjacent to the leaflet frame subcomponent outflow end 1204. As shown in FIGS. 7D1-7D3, the outflow annular groove cover second end 1442 may be contiguously attached to the leaflet frame cover outflow edge 1233 of the leaflet frame cover 1232. For example, the outflow annular groove cover 1440 may be coupled to and circumferentially extend from adjacent the anchor frame subcomponent outflow end 1104 and a leaflet frame cover outflow edge 1233 of the leaflet frame cover 1232, to avoid blood flow through the leaflet frame 1220 into the space or volume corresponding to the outflow annular groove 1706. In some examples, the leaflet frame cover 1232 optionally couples to the anchor frame subcomponent outflow end 1104 and correspondingly, the outflow annular groove cover 1440 is coupled to the leaflet frame subcomponent outflow end 1204 wherein the leaflet frame cover 1232 extends thereto to define a closed volume with the connecting sheath 1300 and the leaflet frame subcomponent 1200. In such instances, it may be desirable for the leaflet frame cover 1232 to also extend to the leaflet frame subcomponent outflow end 1204 to avoid blood flow through the leaflet frame 1220 into the space corresponding to the outflow annular groove 1706.

The outflow annular groove cover 1440 is a tubular element that is operable to extend generally parallel to the longitudinal axis X of the prosthetic valve 1000 (or at a relatively small, or shallow angle relative to the longitudinal axis X), when in the pre-deployed/expanded configuration (e.g., FIG. 7D2) and operable to extend at an angle, and in some examples, in a generally lateral direction to the longitudinal axis X (or at a relatively large, or steep angle relative to the longitudinal axis X) when in the deployed/retracted configuration (e.g., FIG. 7D1). The outflow annular groove cover 1440 is operable to retract during the deployment process, as shown in FIG. 7D1 while the connecting sheath 1300 is operable to fold and evert within the anchor frame subcomponent lumen 1140 of the anchor frame subcomponent 1100 and lie between the leaflet frame subcomponent 1200 and the anchor frame subcomponent 1100 as shown in FIG. 7D1.

The outflow annular groove cover 1440 may be configured to facilitate delivery of the prosthetic valve 1000, and is operable to be elastically restrained to an extended tubular or conical configuration as shown in FIG. 7D2. In particular, the outflow annular groove cover 1440 may also be restrained to define a small tubular diameter in the constrained pre-deployment configuration, such as shown in FIG. 4, at relatively the same diameter as that of the constrained leaflet frame subcomponent 1200 and the constrained anchor frame subcomponent 1100 with the outflow annular groove cover 1440 extending within the anchor frame subcomponent 1100. For reference, as indicated above, in some embodiments, the delivery device 1500 is configured to longitudinally restrain the prosthetic valve 1000 in the un-nested configuration until the time in the delivery sequence at which the leaflet frame subcomponent 1200 is nested into the anchor frame subcomponent 1100.

In some embodiments, the outflow annular groove cover 1440 can help retain the relative position of the leaflet frame subcomponent 1200 and the anchor frame subcomponent 1100 by virtue of an elastic bias of the outflow annular groove cover 1440. For example, the outflow annular groove cover 1440 optionally resists forces in opposition to the outflow annular groove cover 1440 being biased to the retracted configuration.

If desired, the bias may be predetermined to assist with centering or other desirable positioning of the leaflet frame subcomponent 1200 within the anchor frame subcomponent 1100 under physiologic loading conditions. In other embodiments, the bias may be selected to permit some resilient deflection, or adjustment of the position of the leaflet frame subcomponent 1200 within the anchor frame subcomponent 1100 to accommodate physiologic loading, or potentially even better replicate natural physiologic action (e.g., to more closely match movement of a natural valve during a cardiac cycle). In different terms, the bias may be predetermined the such that fluid dynamic forces on the prosthetic valve 1000 are not sufficient to overcome the elastic bias needed to stretch/expand the outflow annular groove cover 1440 which would lead to the leaflet frame subcomponent 1200 moving an unacceptable distance axially or radially within the anchor frame subcomponent lumen 1140 and maintain a relative axial and/or radial position (or at least minimize relative axial or radial movement) between the anchor frame subcomponent 1100 and the leaflet frame subcomponent 1200.

In accordance with an embodiment, the outflow annular groove cover 1440 comprises a pleated, or folded configuration that has a continuous sinuous and/or zig-zag configuration. The pleated, or folded configuration may facilitate reduction of the outflow annular groove cover 1440 to a smaller diameter. The pleated configuration may have an elastic bias, or otherwise resiliently return to the contracted, or retracted configuration.

Although various features are described above, they are provided by way of example and additional or alternative features, associated advantages, and other inventive aspects are contemplated and will be apparent from the disclosure read as a whole.

Annular Groove Cover Materials

In some examples, the outflow annular groove cover 1440 is formed from a retracted microstructure membrane such as those described in U.S. Pat. No. 10,166,128, issued Jan. 1, 2019. Such retracted microstructures exhibit a high degree of recoverable elongation such that they can be extended and resilient retract. They may be formed of fluoropolymer membranes (e.g., porous synthetic fluoropolymer membranes) such that they exhibit high elongation while substantially retaining the strength properties associated with the fluoropolymer membrane. Such retracted microstructure membranes characteristically possess a microstructure of serpentine fibrils that curve or turn generally one way then generally another way. It is to be understood that the amplitude and/or frequency of the serpentine-like fibrils may vary. In some embodiments, the fluoropolymer membranes that go through a retraction process to provide a precursor retracted membrane are formed of expandable fluoropolymers. Non-limiting examples of expandable fluoropolymers include, but are not limited to, expanded PTFE, expanded modified PTFE, and expanded copolymers of PTFE.

The high elongation is facilitated by forming relatively straight fibrils into serpentine fibrils that substantially straighten upon the application of a force in a direction opposite to the compressed direction. The creation of the serpentine fibrils can be achieved through a thermally-induced controlled retraction of the expanded polytetrafluoroethylene (ePTFE), through wetting the article with a solvent, such as, but not limited to, isopropyl alcohol or Fluorinert® (a perfluorinated solvent commercially available from 3M, Inc., St. Paul, MN), or by a combination of these two techniques. The retraction of the article does not result in visible pleating, folding, or wrinkling of the ePTFE, unlike what occurs during mechanical compression. During the retraction process, the fibrils not only become serpentine in shape but also may also increase in width.

The retracted membranes described above can be imbibed with an elastomeric material prior, during, or subsequent to retraction to form a composite such that at least a portion of the pores of a porous material such as ePTFE or the like are filled. Suitable elastomeric materials may include, but are not limited to, PMVE-TFE (perfluoromethylvinyl ether-tetrafluoroethylene) copolymers, PAVE-TFE (perfluoro (alkyl vinyl ether)-tetrafluoroethylene) copolymers, silicones, polyurethanes, and the like. It is to be noted that PMVE-TFE and PAVE-TFE are fluoroelastomers. Other fluoroelastomers include suitable elastomeric materials as identified by those of skill in the art. The resultant retracted membrane composite possesses resilient elongation capability while substantially retaining the strength properties of the fluoropolymer membrane. Moreover, such retracted membranes have the ability to be free of creases, folds or wrinkles visible to the naked eye (i.e., on a gross scale) in both retracted and extended configurations.

In addition to or as an alternative to a membrane or other sheet-like component having elastic recovery (e.g., by coating or imbibing a membrane with elastomer), one or more elastomeric elements may otherwise be associated with a membrane or sheet-like member to provide desired properties. For example, one or more elastomeric bands, members, or other feature may be associated (e.g., bonded, adhered, or mechanically fastened) with a sheet-like member, such as a membrane or film, to provide resilient elongation capabilities to the annular groove cover(s).

In some examples, wherein the material of the outflow annular groove cover 1440 includes a porous elastic film that when in the extended configuration defines pores large enough to render the porous elastic film blood permeable under physiologic conditions and when in the retracted configuration the pores are small enough to render the porous elastic film low-permeability, such as blood impermeable under physiologic conditions.

The materials utilized for the outflow annular groove cover 1440 may also be configured for tissue ingrowth (i.e., to facilitate or promote tissue ingrowth or adhesion) or to resist tissue ingrowth. Moreover, one or more portions of the cover(s) may be configured for tissue ingrowth, whereas other portions are configured to resist tissue ingrowth.

Filler materials may also be utilized in addition to the inflow and outflow annular groove covers. Whether separately injectable (e.g., utilizing a syringe or other delivery mechanism) or associated with the annular groove cover(s) as a coating or other treatment, such filler materials may serve to help fill the inflow annular groove and inflow annular groove 1704 and/or the outflow annular groove 1706 as desired. Examples of such materials include biocompatible filler agents or bulking agents operable to fill a volume and may include at least one of hydrogel, alginate, foam, porous bulking material, collagen, hyaluronic acid, alginic salt, cellulose, chitosan, gelatin, agarose, glycosaminoglycans, polysaccharides, and combinations thereof, among others.

Tissue Engagement Features

In various examples, the one or more tissue engagement features 1118 project away from the anchor frame inner surface 1106 and/or the anchor frame outer surface 1108 of the anchor frame subcomponent 1100, radially outward from a longitudinal axis of the anchor frame subcomponent 1100, and toward the tissue surrounding the prosthetic valve 1000. Generally, the tissue engagement features 1118 are operable to project away from the anchor frame subcomponent 1100 when the anchor frame subcomponent 1100 is deployed (e.g., when a constraining member is withdrawn or otherwise removed). In some examples, with the anchor frame subcomponent 1100 in the deployed configuration, the tissue engagement features 1118 are operable to engage the tissue proximate the anchor frame subcomponent 1100 such that the tissue engagement features 1118 secure the anchor frame subcomponent 1100 to the surrounding tissue, as will be discussed in greater detail below.

In some examples, in a deployed configuration, the tissue engagement features project away from an exterior surface of the anchor frame subcomponent in a range of between thirty (30) and sixty (60) degrees. In some such examples, the tissue engagement features project away from an exterior surface of the anchor frame subcomponent at an angle of approximately forty five (45) degrees, though other configurations are contemplated and fall within the scope of the present application. Generally, any angle of projection is suitable provided that the tissue engagement features operate for their intended purpose of engaging the tissue surrounding the anchor frame subcomponent and causing the anchor frame subcomponent to be secured to the surrounding tissue.

Though the tissue engagement features may include a variety of different lengths (depending on the angle from which they project from the anchor frame subcomponent), it will be appreciated that the tissue engagement features are of a length suitable for engaging tissue and securing the anchor frame subcomponent to the surrounding tissue, but not so long as to risk detrimental damage to the native valve orifice. One nonlimiting example configuration includes tissue engagement features projecting from the anchor frame subcomponent in a range of between thirty (30) and sixty (60) degrees and having a length of between fifty (50) micron and two hundred (200) micron.

Generally, the tissue engagement features 1118 are positioned along the anchor frame subcomponent 1100 such that they are operable to engage tissue proximate the anchor frame subcomponent 1100 when the anchor frame subcomponent 1100 is expanded in-situ. The tissue engagement features 1118 may be arranged in one or more rows along a longitudinal axis of the anchor frame subcomponent 1100. That is, in various examples, the anchor frame subcomponent 1100 may include a first set (or row) of anchors and a second set (or row) of anchors longitudinally offset relative to the first set of anchors. In one such example, the first set of anchors is more proximate the anchor frame subcomponent outflow end 1104 of the anchor frame subcomponent 1100 than is the second set of anchors.

In various embodiments, the one or more tissue engagement features 1118 are circumferentially arranged about the anchor frame subcomponent 1100. In some examples, the one or more tissue engagement features 1118 are evenly dispersed about the circumference of the anchor frame subcomponent. For example, the tissue engagement features 1118 are dispersed about the frame and are offset from one another by ninety (90) degrees depending on the number of anchors. Alternatively, the tissue engagement features 1118 may be dispersed about the frame and offset from one another by sixty (60) degrees depending on the number of anchors. Generally, the angular offset between the anchors is a function of the number of anchors dispersed about the anchor frame subcomponent 1100, as those of skill will appreciate. In some examples, the angular offset between the anchors is additionally or alternatively based on an arrangement or pattern of the frame members 1112.

In various examples, while the tissue engagement features 1118 project away from the anchor frame subcomponent 1100 when the anchor frame subcomponent 1100 is in the deployed configuration, the tissue engagement features 1118 are stowed or do not otherwise project away from the anchor frame subcomponent 1100 when the anchor frame subcomponent 1100 is compressed in the delivery configuration. Thus, in various examples, the tissue engagement features 1118 are stowable during delivery and are configured to transition to a deployed configuration where they project away from the anchor frame subcomponent 1100. In some examples, a constraining member disposed about the anchor frame subcomponent 1100 during delivery facilitates stowing of the tissue engagement features 1118. In some examples, the tissue engagement features 1118 are stowed in associated apertures or voids 1116 of the anchor frame subcomponent 1100.

In various embodiments, the tissue engagement features 1118 are integral to the anchor frame subcomponent 1100. For example, one or more of the tissue engagement features 1118 are formed in conjunction with and from the same material as the frame members 1112. In other examples, one or more of the tissue engagement features 1118 are separate components additionally or alternatively coupled or attached to the anchor frame subcomponent 1100. For instance, some non-limiting examples include crimping and/or welding one or more tissue engagement features to the anchor frame subcomponent 1100.

Leaflet Materials

For simplicity of discussion, when referring to materials from which leaflets 1230 are made, it is appreciated that the same material may also be used to make one or more portions or an entirety of a leaflet construct comprised of one or more leaflets. Therefore, in this context, the description of leaflet materials applies to options that may be employed for one or more individual leaflets, and also one or more portions of a leaflet construct, as well as for an entirety of the leaflet construct. In the examples that follow, the leaflets that are formed with the leaflet materials described are flexible and are comprised of flexible materials.

Suitable leaflet materials include natural materials (e.g., repurposed tissue, including bovine tissue, porcine tissue, or others), synthetic materials (e.g., biocompatible polymers), and combinations of natural and synthetic materials. Suitable leaflet forming processes include, but are not limited to, casting, molding, extruding, wrapping, coating, imbibing, laminating, combinations thereof and others.

Suitable synthetic leaflet materials include urethanes, silicones (e.g., organopolysiloxanes), copolymers of silicon-urethane, styrene/isobutylene copolymers, polyisobutylene, polyethylene, polyethylene-co-poly(vinyl acetate), polyester copolymers, nylon copolymers, fluorinated hydrocarbon polymers, fluoroelastomers (e.g., copolymers of tetrafluoroethylene and perfluoromethyl vinyl ether (TFE/PMVE copolymer) and (per)fluoroalkylvinylethers (PAVE)), and copolymers and/or mixtures of each of the foregoing and composite materials made therewith. Suitable biocompatible polymers, such as one or more of those described above, may exhibit the physical properties of an elastomer, elastomeric, or non-elastomeric material.

Leaflet materials may include composite materials. Suitable composite leaflet materials include, but are not limited to, one or more membranes combined with one or more polymers. In accordance with some examples, the composite material comprises a membrane material (e.g., porous synthetic polymer membrane) by weight in a range of about 10% to about 90%. The one or more polymers may be coatings or layers on the one or more membranes and/or may be imbibed into the one or more membranes (e.g., where the one or more membranes include a microporous structures), for example. Composite materials may include additional or alternative components, such as but not limited to, inorganic fillers, therapeutic agents, radiopaque markers, and others. In some examples, composite leaflet material includes at least one porous synthetic polymer membrane layer having a plurality of pores and/or spaces and a polymer that is an elastomer and/or an elastomeric material filling the pores and/or spaces. In other examples, the composite leaflet material further comprises a layer or coating of elastomer and/or elastomeric material and/or non-elastomeric material on one or both sides of the composite leaflet material.

Suitable membrane materials that is suitable for use in composite leaflet materials include, but are is not limited to, porous synthetic polymer membranes, such as microporous polyethylene and expanded fluoropolymer membranes such as expanded polytetrafluoroethylene (ePTFE). Such membranes can comprise PTFE homopolymer, blends of PTFE, expandable modified PTFE and/or expanded copolymers of PTFE. As referenced, the membranes may have a microporous structures (e.g., such as ePTFE membranes including a matrix of fibrils defining a plurality of spaces within the matrix).

Suitable polymers of composite leaflet materials include polymers that exhibit elastomer, elastomeric, and/or non-elastomeric material properties. Such polymers may include elastomers and elastomeric materials, such as fluoroelastomers. Examples of suitable polymers include TFE-PMVE copolymers, which may exhibit elastomer, elastomeric, and/or non-elastomeric material properties based on the wt % or mol % of the respective polymers. By way of example of a suitable elastomer, TFE/PMVE copolymer is an elastomer when comprising essentially of between 60 and 20 weight percent tetrafluoroethylene and respectively between 40 and 80 weight percent perfluoromethyl vinyl ether. By way of example of a suitable elastomeric material, TFE/PMVE copolymer is an elastomeric material when comprising essentially of between 67 and 61 weight percent tetrafluoroethylene and respectively between 33 and 39 weight percent perfluoromethyl vinyl ether. By way of example of a suitable non-elastomeric material, TFE/PMVE copolymer is a non-elastomeric material when comprising essentially of between 73 and 68 weight percent tetrafluoroethylene and respectively between 27 and 32 weight percent perfluoromethyl vinyl ether. In the foregoing examples, the TFE and PMVE components of the TFE-PMVE copolymer are presented in wt %. For reference, the wt % of PMVE of 40, 33-39, and 27-32 corresponds to a mol % of 29, 23-28, and 18-22, respectively.

In some examples, the composite leaflet material includes an expanded polytetrafluoroethylene (ePTFE) membrane having been imbibed with TFE-PMVE copolymer comprising from about 60 to about 20 weight percent tetrafluoroethylene and respectively from about 40 to about 80 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces. In other examples the leaflet is an ePTFE membrane having been imbibed with TFE-PMVE copolymer comprising from about 70 to about 61 weight percent tetrafluoroethylene and respectively from about 33 to about 39 weight percent perfluoromethyl vinyl ether, the leaflet further including a coating of TFE-PMVE copolymer comprising from about 73 to about 68 weight percent tetrafluoroethylene and respectively about 27 to about 32 weight percent perfluoromethyl vinyl ether on the blood-contacting surfaces.

Although some examples of suitable leaflet materials have been provided, the foregoing examples are not meant to be read in a limiting sense, and additional or alternative materials are contemplated.

In some examples, the leaflet frame cover 1232 and/or the anchor frame cover 1132 and/or connecting sheath 1300 and/or the outflow annular groove cover 1440 may comprise any of the leaflet materials as described above.

Delivery

Figure 10A:
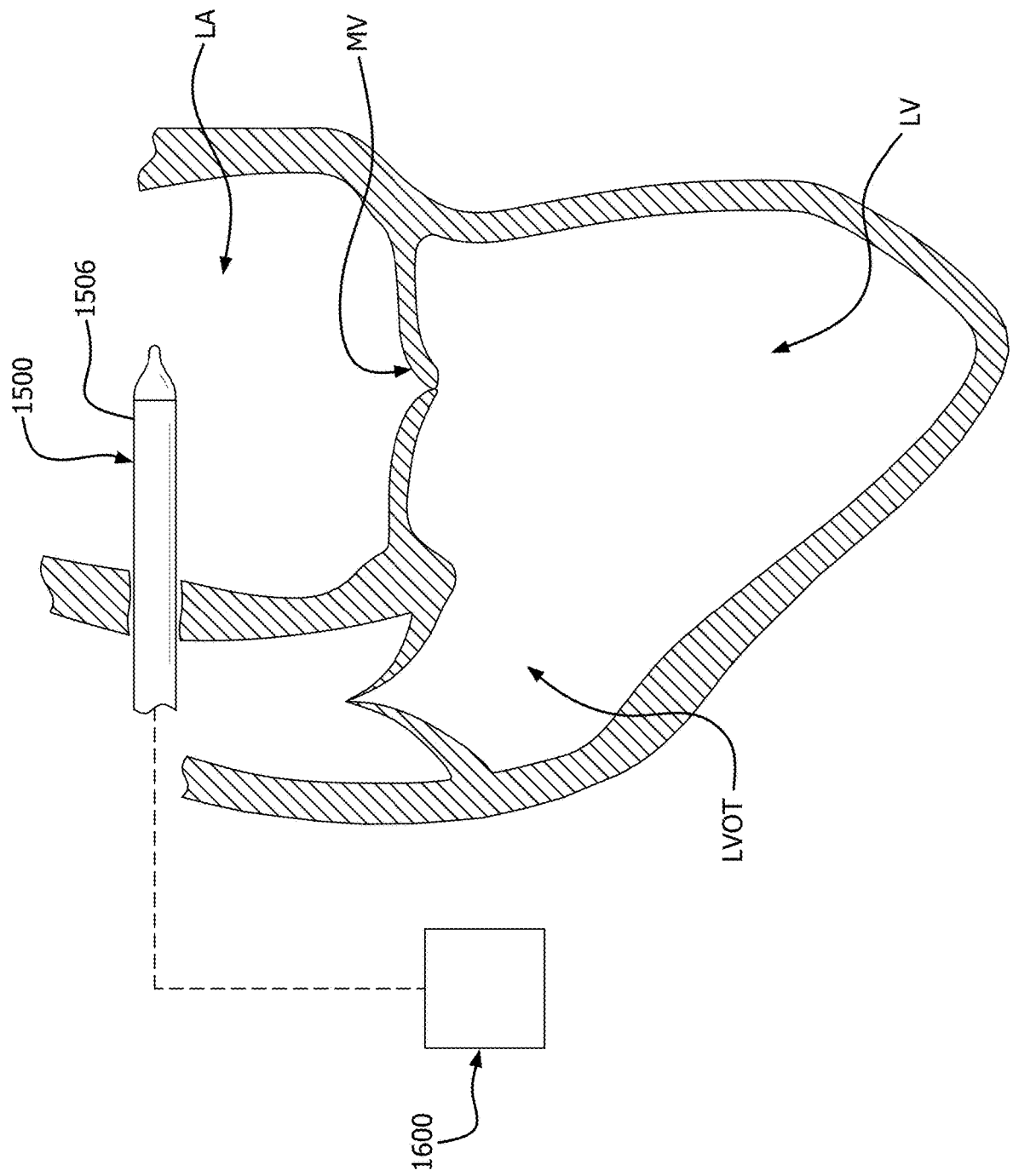
FIG. 10A is a cross-sectional view of a heart illustrating an exemplary medical device delivery procedure, according to some embodiments.

With reference to FIGS. 10A-10M a non-limiting exemplary deployment sequence and nesting configuration of the prosthetic valve 1000 in-situ during a mitral valve ("MV") replacement procedure is shown, with a cross-section of a portion of the heart for illustrative purposes. In FIG. 10A, the left atrium ("LA") is accessed transseptally by a delivery device 1500. In various examples, the delivery device 1500 delivered percutaneously and is coupled to a control system 1600 outside of the body. Accessing the left atrium transseptally can be done in accordance with techniques as known those of skilled in the art. Upon gaining access to the left atrium transseptally, the delivery device 1500 is positioned for deployment of the prosthetic valve 1000. For example, as shown in FIG. 10B, the delivery device 1500 is advanced through the mitral valve and into the left ventricle ("LV"). In some examples, advancement of the delivery device 1500 through the mitral valve causes the anterior leaflet ("AL") and the posterior leaflet ("PL") of the mitral valve to deflect into the left ventricle.

Figure 10C:
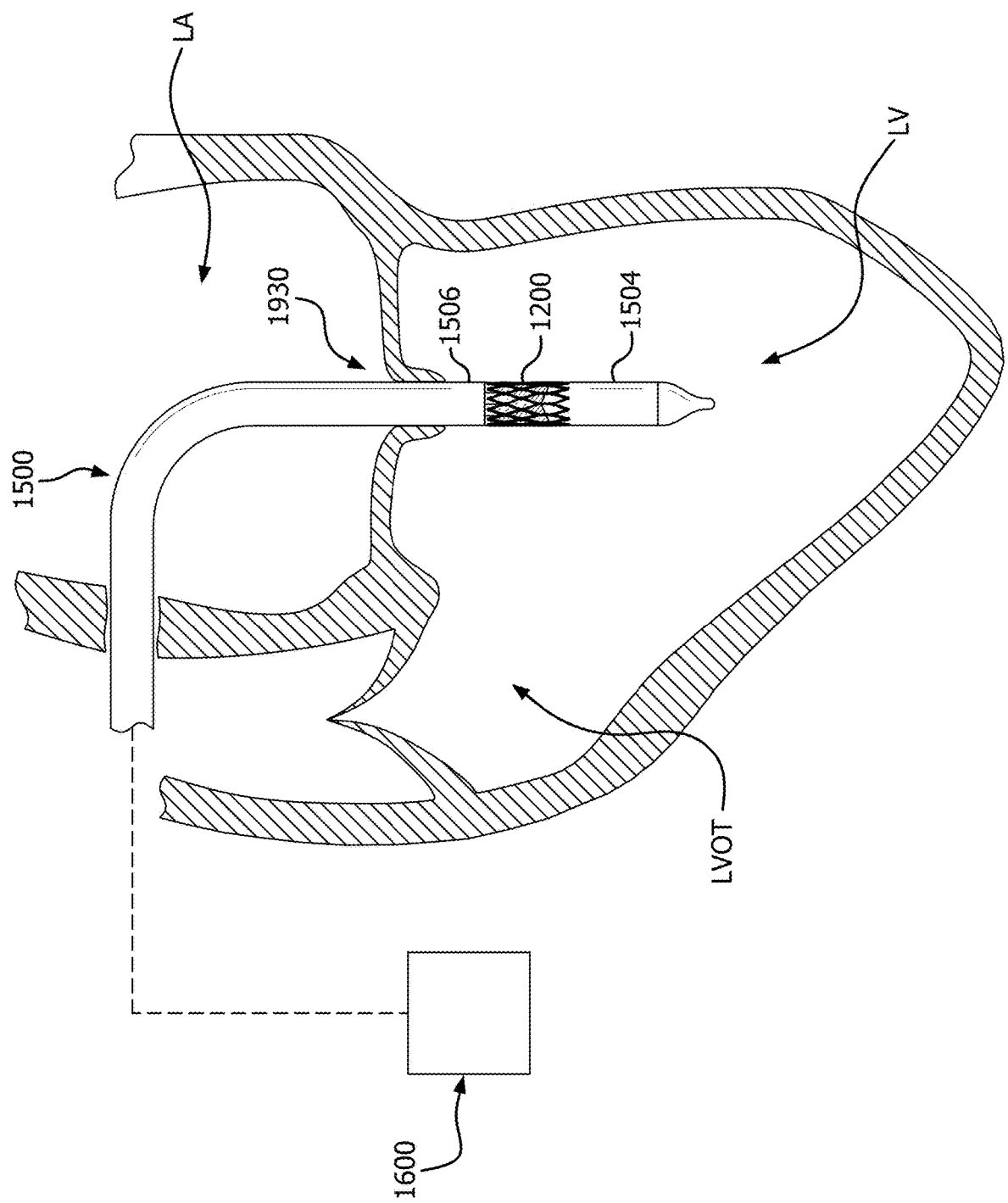
FIG. 10C is a partial cross-sectional view of a prosthetic valve being partially deployed into a mitral valve tissue annulus illustrating an exemplary delivery procedure, according to some embodiments.
Figure 10D:
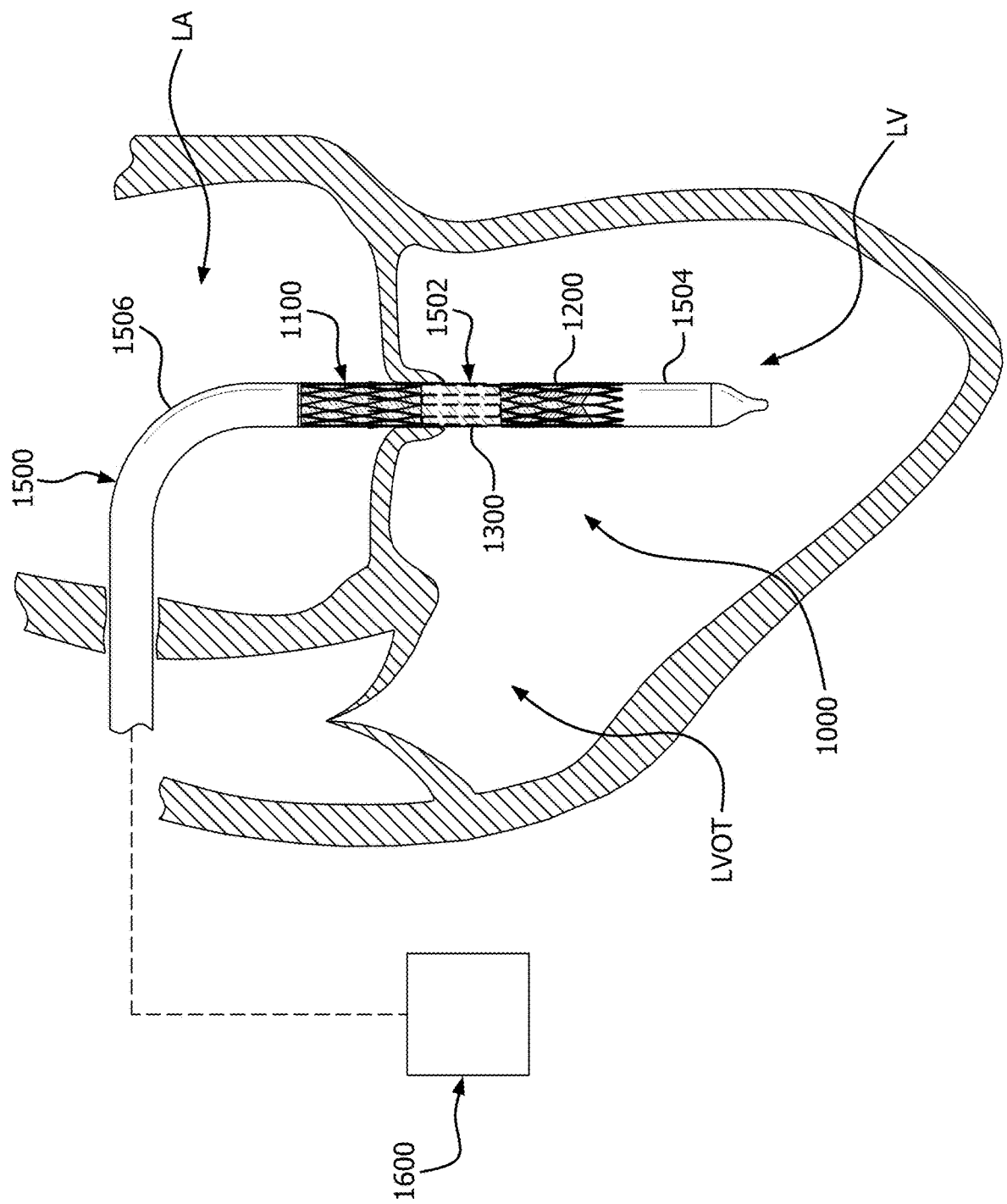
FIG. 10D is a partial cross-sectional view of a prosthetic valve being partially deployed into a mitral valve tissue annulus illustrating an exemplary delivery procedure, according to some embodiments.

FIGS. 10A-10M show a cross-sectional view of a heart illustrating an exemplary medical device delivery procedure using a delivery device 1500 to implant a prosthetic valve 1000 into a mitral valve tissue annulus 1930, according to some embodiments. FIG. 10A shows the delivery device 1500 including a constraining sheath 1506 covering the prosthetic valve (1000, hidden from view). The constraining sheath 1506 is a tubular member that is operable to cover at least a portion of the prosthetic valve 1000 while constrained on the delivery device 1500. Covering a portion or all of the prosthetic valve 1000 with the constraining sheath 1506 presents, among other things, a smoother profile when traversing the anatomical structures and/or protection of the prosthetic valve 1000. The delivery device 1500 is entering the left atrium (LA) in a transseptal procedure to access the mitral valve (MV), in this example. The delivery device 1500 is steerable and flexible to traverse the anatomy. FIG. 10B shows the distal end of the delivery device 1500 being positioned through the mitral valve tissue annulus 1930. FIG. 10C shows the constraining sheath 1506 partially retracted to uncover the leaflet frame subcomponent 1200. FIG. 10D shows the constraining sheath 1506 further retracted to fully uncover the connecting sheath 1300 and partially uncover the anchor frame subcomponent 1100. As now seen, the prosthetic valve 1000 is mounted on a delivery catheter 1504 in a pre-deployed, un-nested configuration with the anchor frame subcomponent 1100 and the leaflet frame subcomponent 1200 being longitudinally offset from one another (also referred to as being delivered in series) and coupled together with the connecting sheath 1300 therebetween, which is also shown in FIG. 4. The retention element 1400 is hidden by the connecting sheath 1300.

As previously discussed and shown in FIG. 4, the leaflet frame subcomponent inflow end 1202 of the leaflet frame subcomponent 1200 is positioned distal to the anchor frame subcomponent outflow end 1104 of the anchor frame subcomponent 1100 with the connecting sheath 1300 coupled thereto and positioned therebetween coupling them together.

Figure 10E:
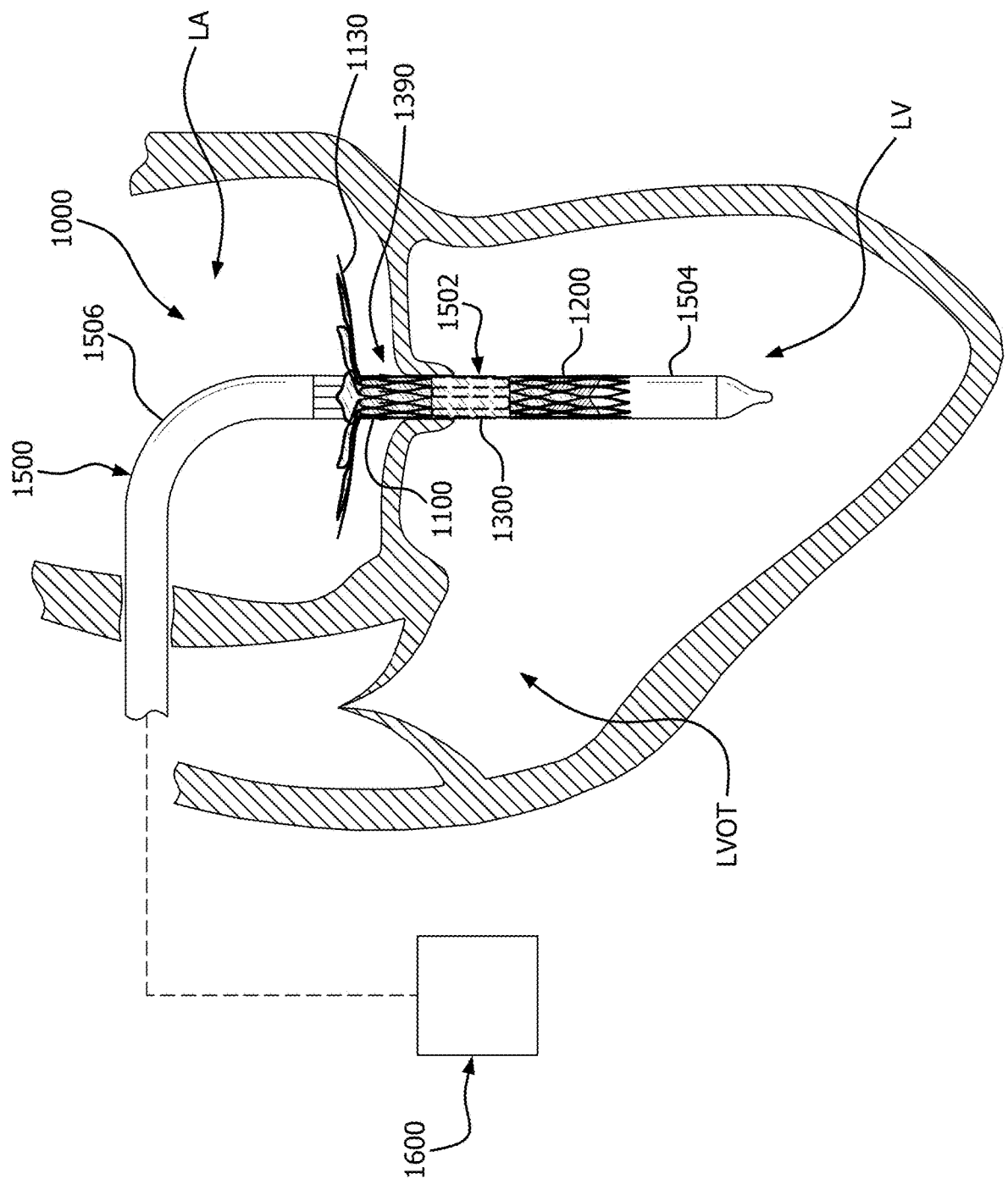
FIG. 10E is a partial cross-sectional view of a prosthetic valve being partially deployed into a mitral valve tissue annulus illustrating an exemplary delivery procedure, according to some embodiments.
Figure 10F:
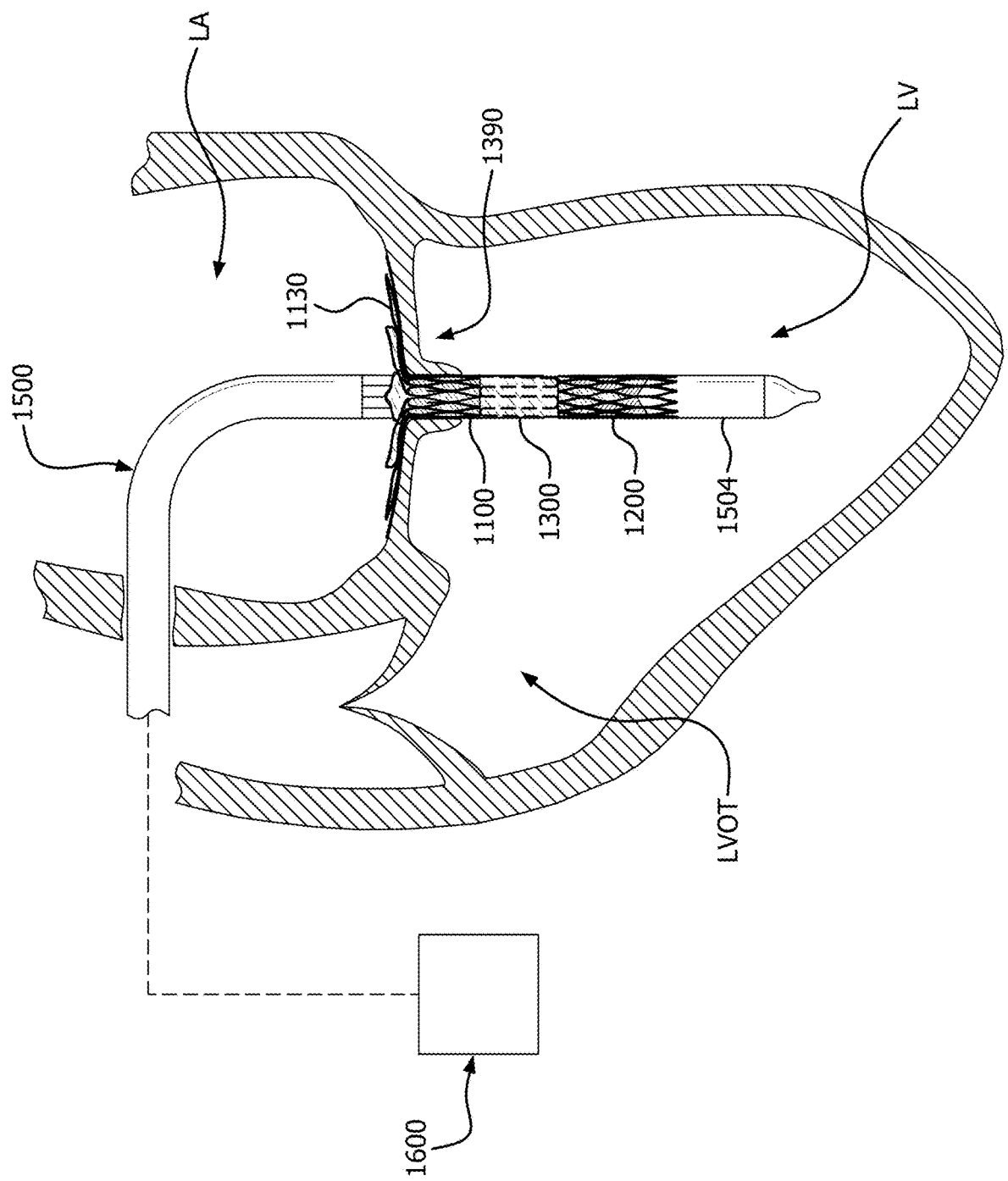
FIG. 10F is a partial cross-sectional view of a prosthetic valve being partially deployed into a mitral valve tissue annulus illustrating an exemplary delivery procedure, according to some embodiments.
Figure 10G:
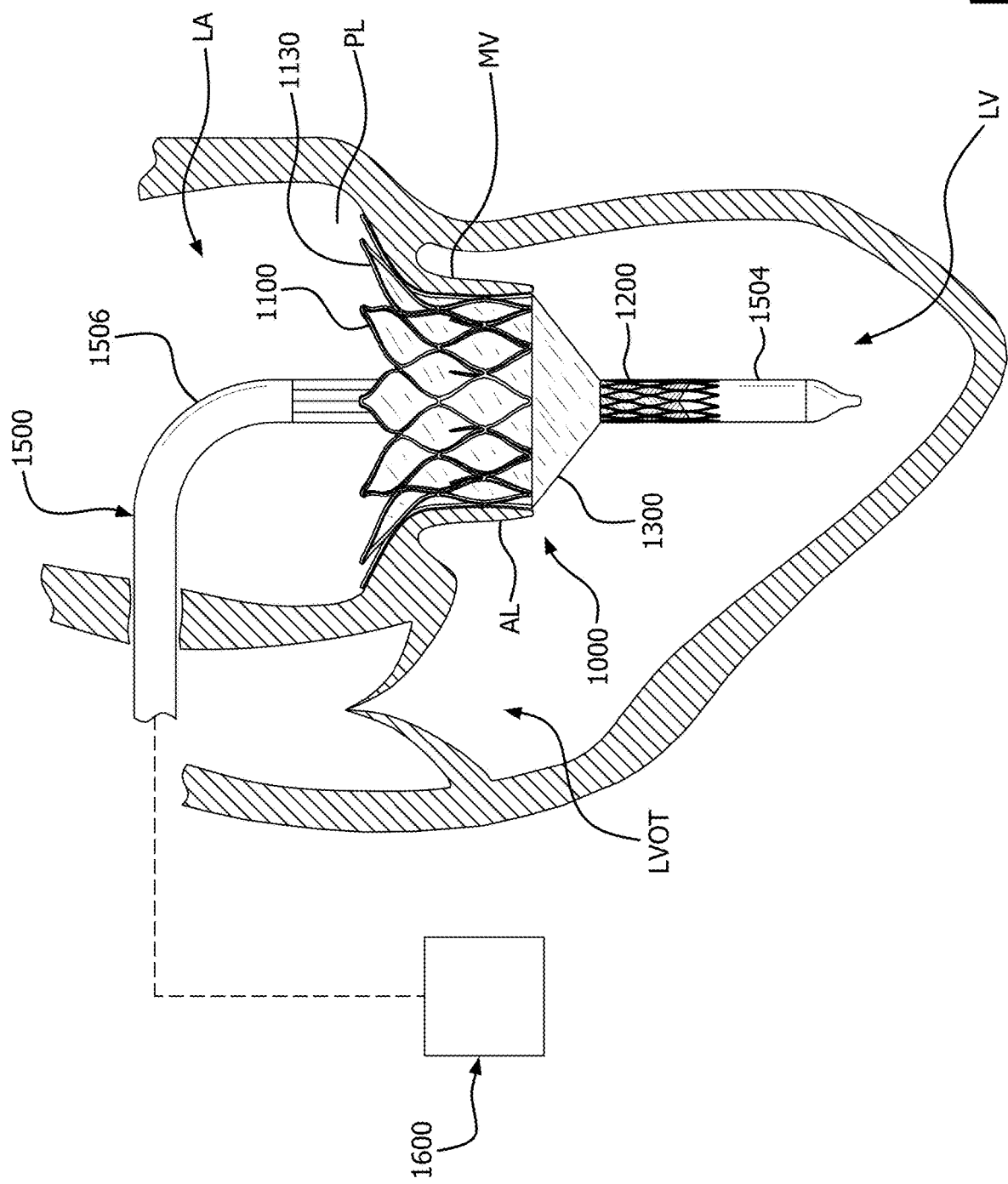
FIG. 10G is a partial cross-sectional view of a prosthetic valve being partially deployed into a mitral valve tissue annulus illustrating an exemplary delivery procedure, according to some embodiments.

FIG. 10E shows the constraining sheath 1506 further retracted to fully uncover the anchor frame subcomponent 1100 which allows the flared portion 1130 to expand to a deployed configuration from the constrained configuration. In this example, the constraining sheath 1506 constrained the flared portion 1130, wherein in other examples other means of constraining may be used. The remaining portion of the anchor frame subcomponent 1100 and the leaflet frame subcomponent 1200 remain constrained to the delivery catheter 1504 by constraining elements 1716 as shown in FIG. 4. In various examples, withdrawal of a constraining sheath 1506 releases the flared portion 1130 as shown in FIG. 1B1 or flange element of FIG. 1150 as shown in FIGS. 1B2-1B3 which engages the tissue annulus 1390, as shown in FIGS. 10E-10G. The other portions of the prosthetic valve 1000 are restrained to the delivery catheter 1504 by use of constraining elements 1716 such as fiber loops shown in FIG. 4. The prosthetic valve 1000 may be positioned and oriented within the tissue annulus 1390 by advancing and withdrawing and otherwise manipulating the delivery catheter 1504 or delivery device 1500 as a whole, for a particular purpose, such as to ensure correct orientation and engagement with the anatomical structure of the tissue annulus 1390 and surrounding tissue.

FIG. 10F shows the flared portion 1130 advanced to and placed in contact with the tissue annulus 1390. The delivery catheter 1504 or delivery device 1500 as a whole may be manipulated such that the flared portion 1130 and thus the anchor frame subcomponent 1100 may be positioned and repositioned suitable fora particular purpose. FIG. 10G shows the anchor frame expanded to a larger diameter of the deployed configuration. Before disengagement of the constraining element 1716 that constrains the anchor frame subcomponent 1100 to the delivery catheter 1504, the position of the anchor frame subcomponent 1100 is verified, and if incorrect, the constraining element 1716 may be used, such as by instilling tension to the constraining element 1716 via a tether, for example, to re-constrain the anchor frame subcomponent 1100 back onto the delivery catheter 1504 for repositioning or removal.

In various examples wherein the anchor frame subcomponent 1100 includes tissue engagement features 1118, such as shown in FIGS. 1B1, the constraining element 1716 may constrain the deployment of the tissue engagement features 1118 so as to allow for repositioning or withdrawal of the anchor frame subcomponent 1100 from within the tissue annulus 1390. With the constraining element 1716 constraining the deployment of the tissue engagement features 1118, such as tissue anchors, re-constraining and repositioning of the anchor frame subcomponent 1100 may be done without trauma to the tissue.

Figure 10H:
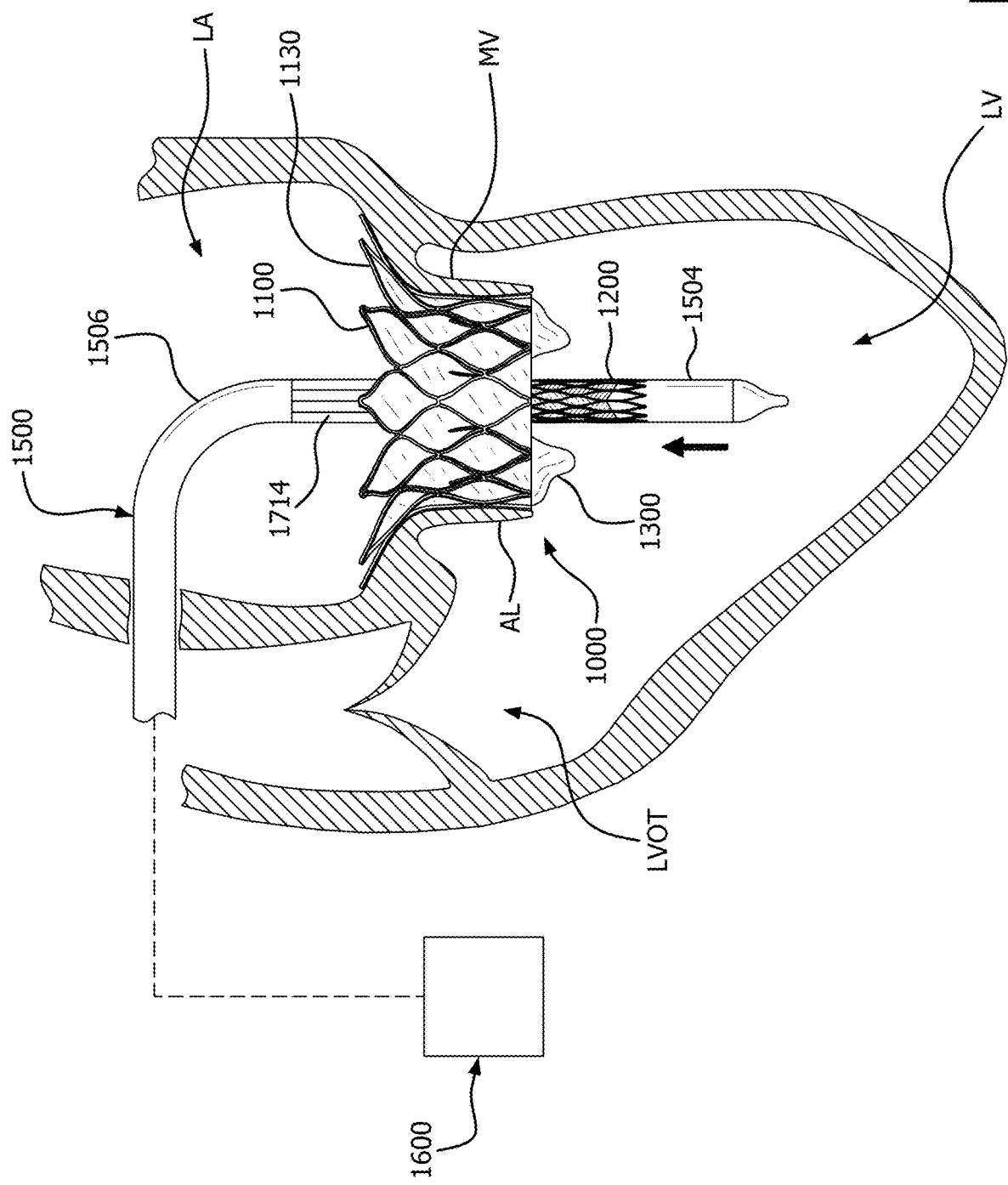
FIG. 10H is a partial cross-sectional view of a prosthetic valve being partially deployed into a mitral valve tissue annulus illustrating an exemplary delivery procedure, according to some embodiments.

In various examples, after the anchor frame subcomponent 1100 is expanded, the anchor frame subcomponent 1100 and the leaflet frame subcomponent 1200 are nested together. In various examples, nesting of the anchor frame subcomponent 1100 and the leaflet frame subcomponent 1200 in-situ involves proximally advancing the leaflet frame subcomponent 1200 relative to the anchor frame subcomponent 1100. FIG. 10H illustrates the leaflet frame subcomponent 1200 as it is proximally advanced relative to the anchor frame subcomponent 1100 as indicated by the arrow. FIG. 10H shows the delivery catheter 1504 being withdrawn from the anchor frame subcomponent 1100 which pulls the connecting sheath 1300 and a portion of the leaflet frame subcomponent within the anchor frame subcomponent 1100 with the connecting sheath 1300 in the process of being everted therebetween.

Figure 10I:
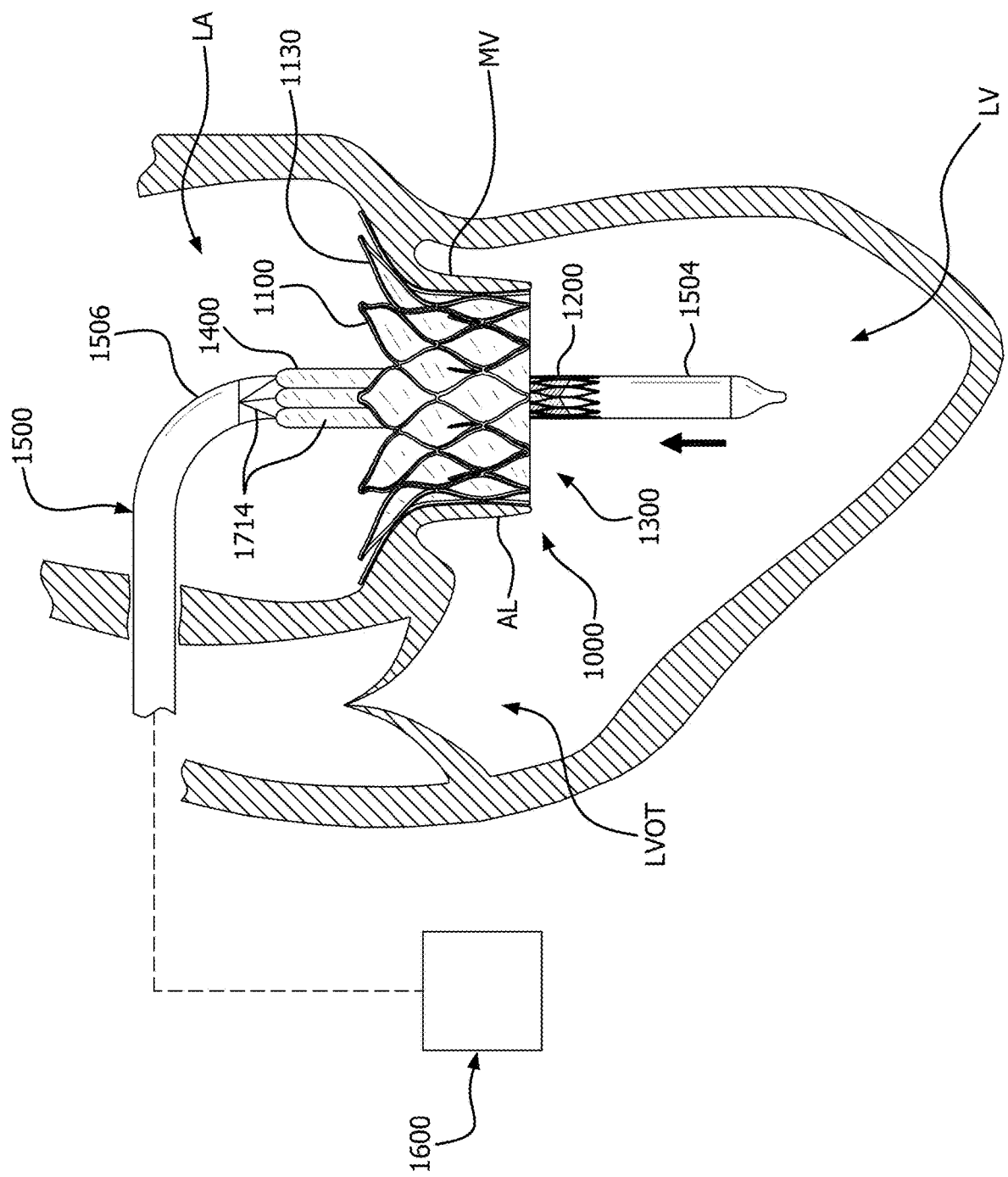
FIG. 10I is a partial cross-sectional view of a prosthetic valve being partially deployed into a mitral valve tissue annulus illustrating an exemplary delivery procedure, according to some embodiments.

Alternatively, or in addition thereto, FIG. 10I shows the delivery catheter 1504 being further withdrawn from the anchor frame subcomponent 1100, and/or the pulling of tethers as discussed below, which pulls the connecting sheath 1300 and a portion of the leaflet frame subcomponent 1200 within the anchor frame subcomponent 1100 with the connecting sheath 1300 having been everted therebetween. As shown in FIG. 10I, one or more tether elements 1714 are coupled to the retention element 1400 as shown, and alternatively shown as a lasso or loop in FIG. 7A and discussed further below, which may be used to pull the retention element 1400 through the anchor frame subcomponent 1100, and therefore also pull the leaflet frame subcomponent 1200 therewith into the anchor frame subcomponent 1100.

As will be discussed below, if it is required to remove the prosthetic valve 1000 from the heart at this point in the deployment, the leaflet frame subcomponent 1200 may be recompressed by the tether elements 1714 and the tether elements 1714 may be used to pull the retention element 1400, and thus the leaflet frame subcomponent 1200 and subsequently the anchor frame subcomponent 1100 into the constraining sheath 1506 or a larger retrieval sheath 1950, shown in FIGS. 9A-9D, that had been advanced over the delivery device 1500. In this case, the anchor frame subcomponent 1100 is caused to evert initiating at the anchor frame subcomponent outflow end 1104 such that it is drawn, peeled or pulled away from the tissue annulus 1930, such as illustrated in FIGS. 9A-9D. Thus, this method provides a means for removing a prosthetic valve 1000 that is experiencing a failed deployment without the need for invasive surgical care.

Figure 10J:
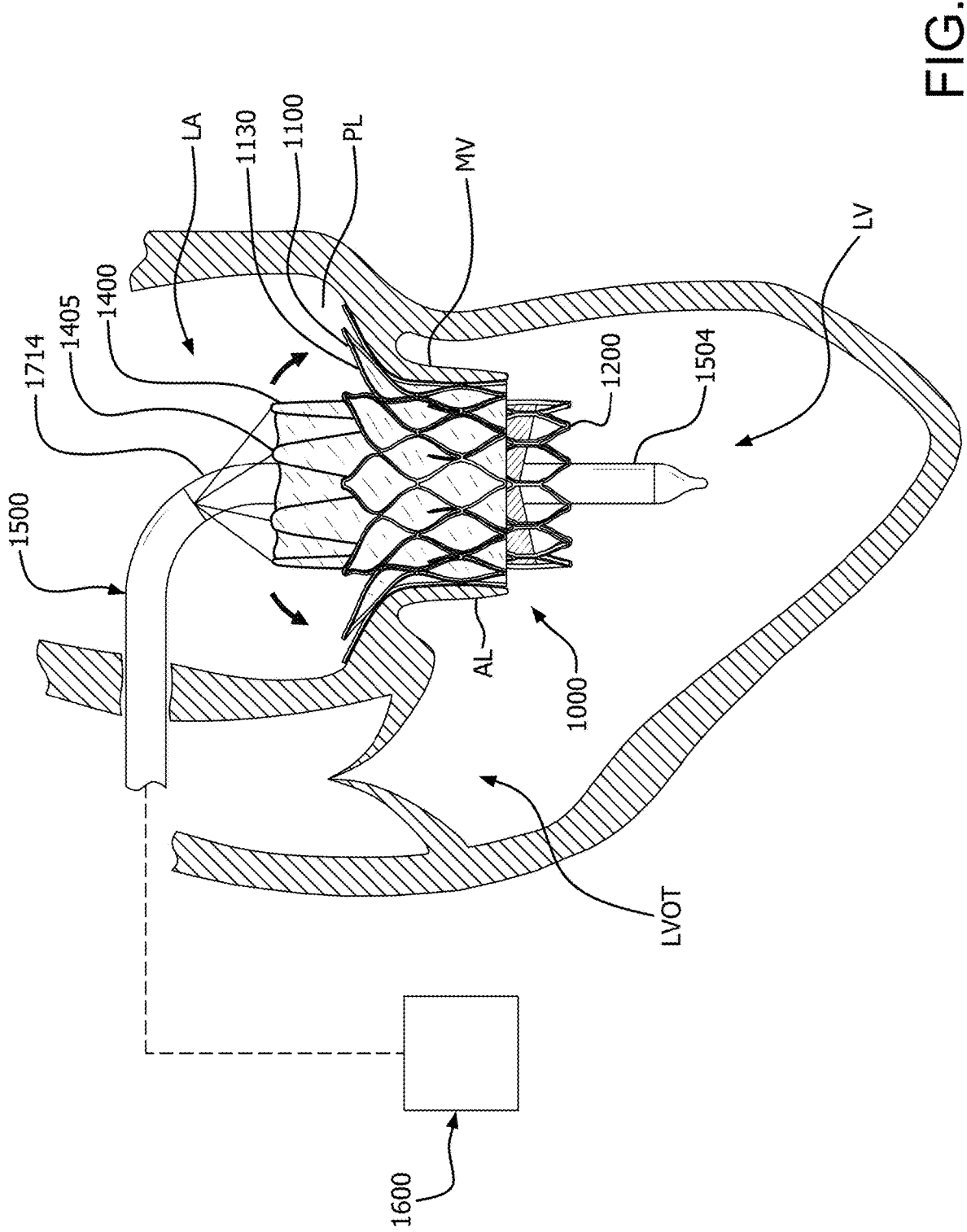
FIG. 10J is a partial cross-sectional view of a prosthetic valve being partially deployed into a mitral valve tissue annulus illustrating an exemplary delivery procedure, according to some embodiments.
Figure 10K:
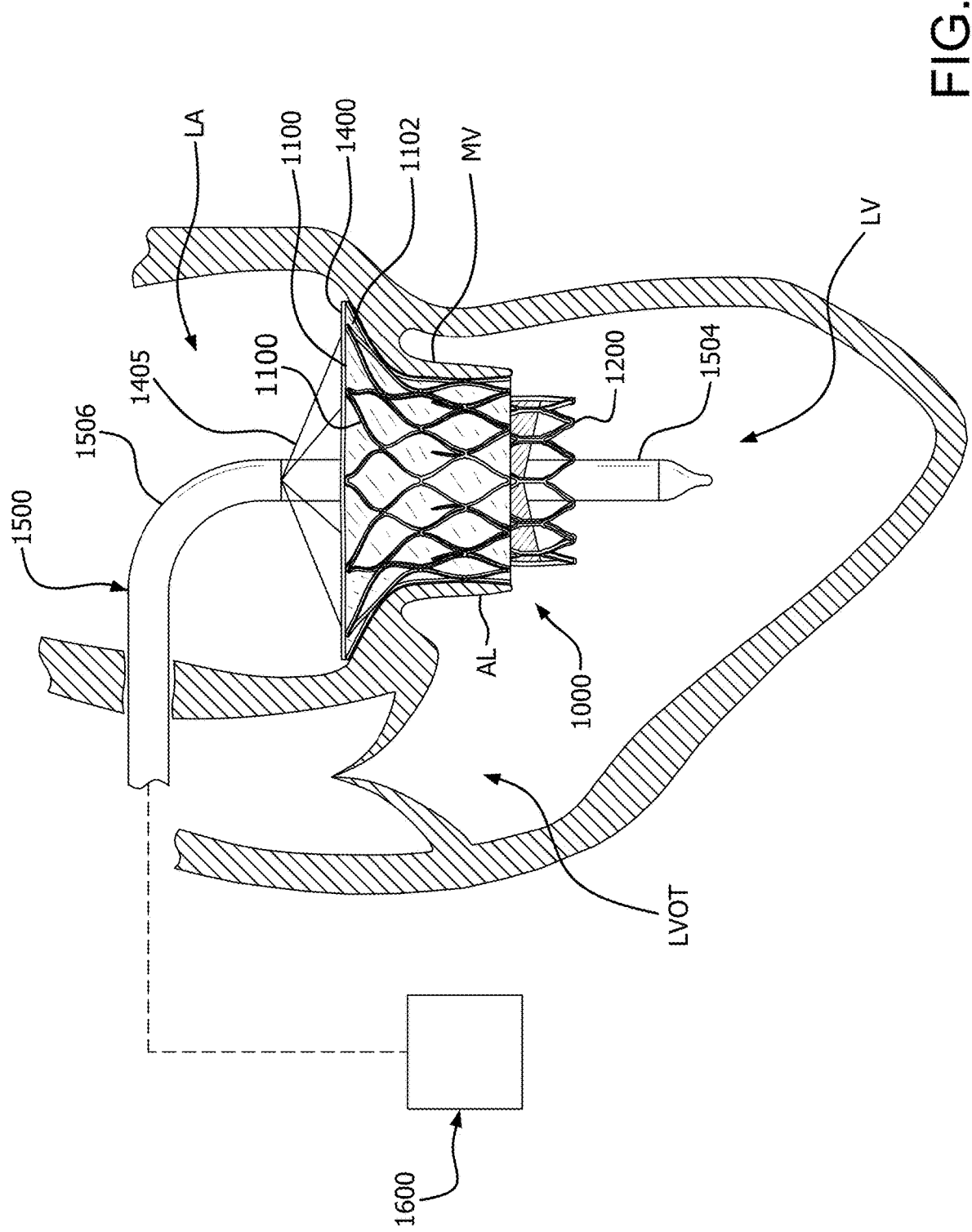
FIG. 10K is a partial cross-sectional view of a prosthetic valve being deployed into a mitral valve tissue annulus illustrating an exemplary delivery procedure, according to some embodiments.
Figure 10L:
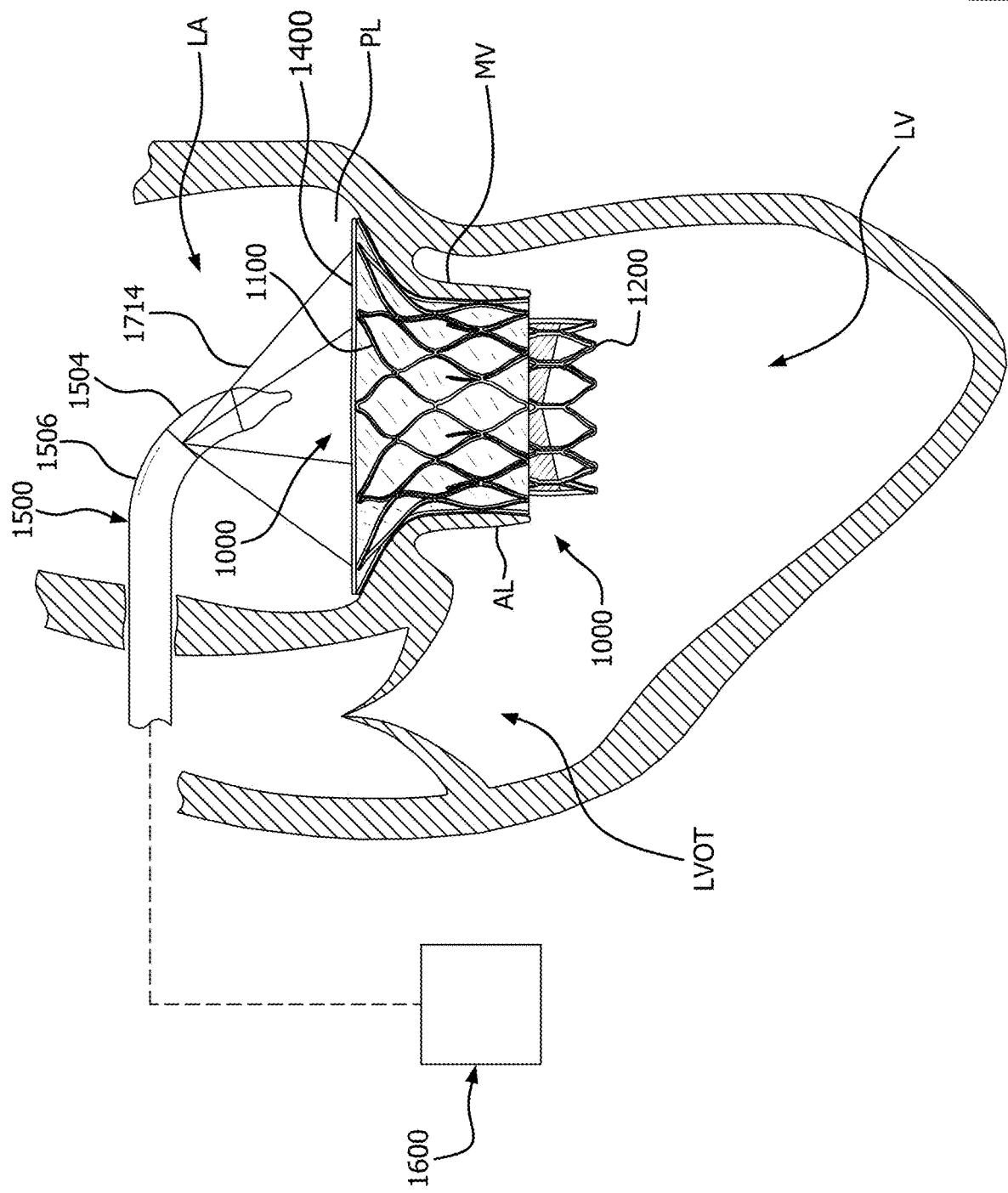
FIG. 10L is a partial cross-sectional view of a prosthetic valve being deployed into a mitral valve tissue annulus illustrating an exemplary delivery procedure, according to some embodiments.
Figure 10M:
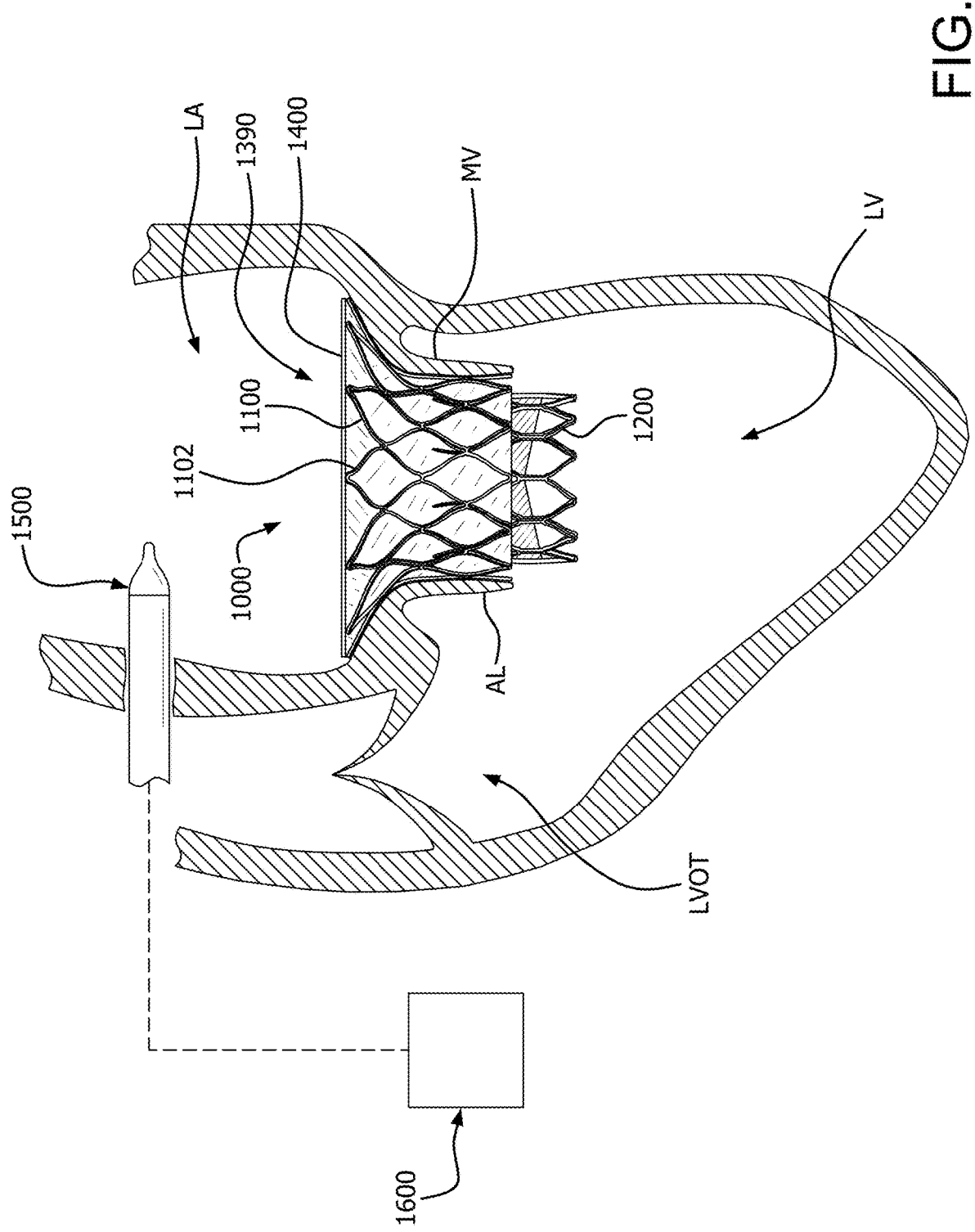
FIG. 10M is a partial cross-sectional view of a prosthetic valve having been deployed into a mitral valve tissue annulus illustrating an exemplary delivery procedure, according to some embodiments.

In various examples, after the leaflet frame subcomponent 1200 is nested and expanded within the anchor frame subcomponent 1100, the tether elements 1714 are loosened allowing the retention element 1400 to expand and rotate downward from the leaflet frame subcomponent 1200 under spring bias as shown in FIG. 10J so as to fully deploy over the anchor frame subcomponent inflow end 1102 as shown in FIG. 10K. The delivery catheter 1504 may be withdrawn from the prosthetic valve 1000, as shown in FIG. 10L, so as to verify that the leaflets 1230 are properly functioning prior to releasing the tether elements 1714 from the retention element 1400. If the leaflets 1230 are not functioning properly, the delivery catheter 1504 may be advanced adjacent to or within the leaflet frame subcomponent 1200 and the prosthetic valve 1000 removed with the procedure discussed above.

Further, additional tethers may be coupled to the leaflet frame subcomponent inflow end 1202 operable to constrain and pull the leaflet frame subcomponent 1200 out of the anchor frame subcomponent 1100 as discussed before in reference to FIGS. 9A-9D.

FIG. 10L shows the prosthetic valve 1000 fully deployed within the tissue annulus 1390 of the mitral valve (MV). The prosthetic valve 1000 is in a fully deployed configuration wherein the anchor frame subcomponent 1100 and the leaflet frame subcomponent 1200 are nested. The prosthetic valve 1000 is fully deployed and operational upon the retention element 1400 engaging the anchor frame subcomponent inflow end 1102 which minimizes relative axial translation between the anchor frame subcomponent 1100 and the leaflet frame subcomponent 1200.

In various examples, the longitudinal separation or offset of the anchor frame subcomponent 1100 and the leaflet frame subcomponent 1200 provides for a low profile delivery configuration that can be easily tracked through the vasculature of the patient. For instance, by longitudinally offsetting the anchor frame subcomponent 1100 and the leaflet frame subcomponent 1200, a profile of the delivery system can be minimized because, unlike conventional designs, the anchor frame subcomponent 1100 and the leaflet frame subcomponent 1200 do not overlap one another during delivery. In some examples, a maximum profile of the delivery device 1500 including the prosthetic valve 1000 can be 8 mm or less.

Additionally, as shown in FIGS. 4 and 10D, a region 1502 of the delivery device 1500 positioned between the anchor frame subcomponent 1100 and the leaflet frame subcomponent 1200 and adjacent to the connecting sheath 1300 and retention element 1400 is operable to bend such that the anchor frame subcomponent 1100 and the leaflet frame subcomponent 1200 are temporarily misaligned with one another. In some examples, such a configuration is akin to rail cars navigating a curve. Such a configuration is beneficial in procedures where the prosthetic valve 1000 is delivered to a treatment region transseptally, which may require a delivery device to bend ninety (90) degrees or more within the left atrium of the heart.

Additionally, as shown in FIG. 1A, the tissue engagement features 1118 of the anchor frame subcomponent 1100 extend away from the anchor frame subcomponent 1100 and engage the tissue of the native valve orifice surrounding the prosthetic valve 1000. In some examples, the tissue engagement features 1118 are configured to penetrate the tissue or otherwise embed within the tissue. In various examples, this interaction of the tissue engagement features 1118 of the anchor frame subcomponent 1100 with the native tissue surrounding the prosthetic valve 1000 operates to secure the anchor frame subcomponent 1100 (and thus the leaflet frame subcomponent 1200) to the native tissue of the tissue annulus 1390.

The anchor frame subcomponent inflow end 1102 of the anchor frame subcomponent 1100 illustrated in FIGS. 10B-10M is flared radially outward and is situated adjacent to and in abutment with the native valve tissue annulus 1390, as shown. In some examples, such a configuration provides that the anchor frame subcomponent inflow end 1102 of the anchor frame subcomponent 1100 obstructs or otherwise limits the extent to which the anchor frame subcomponent 1100 is operable to extend through the native valve. For instance, in the case of a mitral valve replacement, such a flared anchor frame subcomponent inflow end 1102 limits the extent to which the anchor frame subcomponent 1100 can be advanced through the natural mitral valve orifice and into the left ventricle. In some examples, such flared anchor frame subcomponent inflow end 1102 additionally operates to minimize the potential for the anchor frame subcomponent 1100 to migrate distally.

While the embodiments and examples illustrated and described above pertain to trans-septal delivery, it should be appreciated that a variety of additional well-known delivery procedures can be utilized without departing from the spirit or scope of the present application. Additional non-limiting delivery procedures include trans-apical, left atriotomy, and trans-aortic. Generally, regardless of the particular delivery procedure, those of skill should appreciate that after deploying the prosthetic valve 1000, the leaflet frame subcomponent 1200 and the anchor frame subcomponent 1100 are nested by proximally advancing the leaflet frame subcomponent 1200 relative to the anchor frame subcomponent 1100.

Tissue Ingrowth Materials and Modifications

In various embodiments, one or more portions of the prosthetic valve 1000, such as the leaflets 1230, are constructed in a manner that promotes tissue ingrowth. In some embodiments, the leaflets 1230 and/or other portions of the valve 1000 may be constructed to encourage tissue ingrowth and proliferation across one or more discrete regions, portions, or sections of one or more of the materials forming the prosthetic valve 1000, or alternatively across an entirety of one or more of the materials forming the prosthetic valve 1000, such as the leaflets 1230. Tissue ingrowth and proliferation may be promoted on an outflow side or surface of such materials, and/or on an inflow side or surface of such materials, and/or within one or more such materials.

In various embodiments, materials configured to promote tissue ingrowth include a composite material combined with a tissue ingrowth curtain that may be incorporated into the composite material and/or coupled to the composite material.

In various embodiments, one or more portions of the leaflet frame subcomponent 1230 may be covered with material suitable for promoting tissue ingrowth. For example, the leaflet frame subcomponent 1230 can be wrapped with a material, suitable for promoting tissue ingrowth. In various examples, such tissue ingrowth promoting materials can be applied to the leaflet frame subcomponent 1230 entirely, or alternatively to less than all of the leaflet frame subcomponent 1230. For example, suitable materials for promoting tissue ingrowth could be coupled to the leaflet frame inner surface and the leaflet frame outer surface of the leaflet frame. Some nonlimiting examples of materials that can be applied to the leaflet frame subcomponent 1230 (or other portions of the prosthetic valve 1000) include expanded polytetrafluoroethylene (ePTFE), such as an ePTFE membrane, as well as fabric, film, or coating, and a polyethylene terephthalate fabric (e.g., Dacron fabric).

According to some examples, as will be discussed in greater detail below, this promotion of tissue ingrowth is facilitated by the coupling of one or more synthetic tissue ingrowth curtains to one or more composite materials such that tissue is encouraged to grow (or is not otherwise prevented or inhibited from growing) into and/or onto the one or more tissue ingrowth curtains. That is, in some examples, one or more layers configured to promote tissue ingrowth may be applied to the composite material. In some examples, as described herein, the underlying material may be configured to inhibit or prevent tissue ingrowth.

Additionally or alternatively, in some examples, this promotion of tissue ingrowth is facilitated by selectively imbibing, such as with one or more fluoroelastomers, one or more portions of the one or more materials forming the leaflet 1230 and/or other portions of the prosthetic valve 1000. Reference to "selectively imbibing" is referring to the act of imbibing a porous material with a filling material at selected portions of the porous material or to a lesser degree leaving a degree of porosity of the porous material.

That is, in some examples, in addition to or as an alternative to coupling one or more synthetic tissue ingrowth curtains to one or more composite materials, the composite material as discussed above regarding leaflet materials is configured to promote or accommodate tissue ingrowth. In some such examples, as discussed in greater detail below, the composite material is configured such that tissue is encouraged to grow (or is not otherwise prevented or inhibited from growing) into and/or onto one or more discrete or designated sections, portions, or regions of the composite material by way of selectively imbibing the membrane associated with those portions.

In various embodiments, the tissue ingrowth curtain generally includes an expanded fluoropolymer membrane which comprises a plurality of spaces within a matrix of fibrils that is suitable for promoting and supporting the ingrowth of tissue. Other nonlimiting example materials include other biocompatible porous materials such as knit PTFE. However, as mentioned above, and as discussed in greater detail below, in some examples the tissue ingrowth curtain(s) may be applied to the composite material in the form of one or more coatings.

In some examples, the tissue ingrowth curtain includes an expanded fluoropolymer made from a porous ePTFE membrane. However, it is appreciated that the tissue ingrowth curtain may be formed from a number of different types of membranes, including other fluoropolymer membranes, and other biocompatible porous materials such as porous polyethylene membrane and knit PTFE. For instance, the expandable fluoropolymer can comprise PTFE homopolymer. In some examples, the tissue ingrowth curtain can be formed from copolymers of hexafluoropropylene and tetrafluoroethylene, such as Fluorinated Ethylene Propylene (FEP). In some examples, blends of PTFE, expandable modified PTFE and/or expanded copolymers of PTFE can be used. It will thus be appreciated that the tissue ingrowth curtain may be formed from a variety of different polymeric materials provided they are biocompatible and possess or are modified to include a suitable microstructure suitable for promoting or supporting tissue ingrowth. In various examples, the tissue ingrowth curtains may range in thickness from between one micron and four hundred microns depending on the selected material.

In some examples, the polymeric material may include one or more naturally occurring and/or one or more artificially created pores, reliefs, channels, and/or predetermined surface topology, suitable for supporting tissue ingrowth. Other biocompatible materials which can be suitable for use in forming the tissue ingrowth curtain include but are not limited to the groups of urethanes, fluoropolymers, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

While the above-discussed tissue ingrowth curtains generally include membranes, films, knits, or other structures that are bonded, applied, or otherwise attached to the composite material, as mentioned above, in some examples the tissue ingrowth curtain(s) may be applied to the composite material in the form of one or more coatings. In some such example, a coherent irregular network is distributed or deposited onto one or more portions, regions, sections, areas, or zones of the composite material. In some examples, the coherent irregular network is applied to one or more portions of the composite material to create a surface texture suitable for supporting the ingrowth and proliferation of tissue, as those of skill will appreciate. For example, the coherent irregular network may be selectively applied to one or more discrete or designated sections, portions, or regions of the composite material. In some such examples, the coherent irregular network is applied to the designated areas by masking or otherwise covering those portions of the underlying leaflet, or other portion of the prosthetic valve 1000, where ingrowth of tissue is undesirable such that the cover or mask can be removed subsequent to the coherent irregular network application process to achieve a material having a first region including the coherent irregular network and a second region free of a coherent irregular network.

In some examples, one or more sacrificial sheets, such as one or more polyimide sheets (e.g., Kapton sheets), are arranged on the composite material and operate to mask or otherwise prevent the coherent irregular network from being applied to the masked or covered areas. Some nonlimiting examples of sacrificial sheet materials include polyester, polyetheretherketone (PEEK), PET, ePTFE/Kapton blends such as mapton, ePTFE, PTFE, silicones, and stainless steel, or other thin metal sheeting. In some examples, the one or more sacrificial sheets can be removed after the coherent irregular network application process to reveal a structure including one or more regions including the coherent irregular network and one or more regions free of the coherent irregular network (e.g., where the underlying composite material is exposed). Such a configuration provides for a construction that minimizes a possibility for delamination between bonded membrane layers.

As mentioned above, in some examples, in addition to or as an alternative to applying one or more tissue ingrowth curtains to the composite material, the composite material is configured to promote or accommodate tissue ingrowth. For instance, in some examples, the composite material is configured such that tissue is encouraged to grow (or is not otherwise prevented or inhibited from growing) into and/or onto one or more discrete or designated sections, portions, or regions of the composite material. For instance, as mentioned above, the composite material may include an elastomer and/or an elastomeric material such as a fluoroelastomer imbibed or otherwise incorporated into the expanded fluoropolymer membrane. In various examples, to achieve a composite material that promotes or otherwise accommodates the ingrowth and proliferation of tissue the expanded fluoropolymer membrane is selectively imbibed, such as with one or more fluoroelastomers, such that the expanded fluoropolymer membrane includes one or more discrete portions, regions, sections, zones, or areas that are free of or are not otherwise imbibed with the elastomeric filler material (or at least are not filled to the extent that the elastomeric filler material operates to prevent tissue ingrowth). Selectively imbibing the membrane material of the composite material may be done in accordance with techniques as known to those of skill in the art.

While the above discussed embodiments and examples include applying a tissue ingrowth curtain to one or more portions of one or more surfaces of the composite material, or selectively imbibing one or more portions of one or more sides of a membrane of the composite material with a filler material, it will be appreciated that, in various examples, a leaflet, and/or other features of the prosthetic valve 1000, may be constructed by both imbibing one or more portions of the membrane and applying a tissue ingrowth curtain to the selectively imbibed membrane.

In various examples, the membrane may be imbibed with a plurality of filler materials. That is, in some examples, a first portion, area, region, section, or zone of the membrane of composite material may be imbibed with a first filler material while a second portion, area, region, section, or zone of the membrane of the composite material is imbibed with a second filler material. For instance, in some examples, a first portion of the membrane of the composite material is imbibed with a first filler material such that the first portion of the membrane is resistant to or otherwise inhibits or prevents tissue ingrowth into and/or onto and/or across the first portion. However, in some examples, those portions of the membrane imbibed with the first filler may also be unsuitable for accommodating the bonding or coupling of a tissue ingrowth curtain. Accordingly, in examples where it is desirable bond or otherwise couple a tissue ingrowth material to a second portion of the membrane, the second portion may be imbibed with a second filler material such that the second portion of the membrane is suited to have a tissue ingrowth curtain bonded or otherwise coupled thereto. In some examples, the second filler material may additionally or alternatively encourage tissue ingrowth. That is, in some examples, one or more portions of the membrane may be imbibed with a filler material that encourages tissue ingrowth and proliferation. Alternatively, as mentioned above, the second portion may not be imbibed with any filler material at all, but may instead remain free of filler material.

In some examples, the method includes applying an adhesive to the membrane in addition to or as an alternative to applying the adhesive to the tissue ingrowth curtain, as discussed above. In some examples, an adhesive, such as FEP, is similarly wicked or imbibed into one or more portions of the membrane, after which the tissue ingrowth curtain and the membrane are pressed together and/or heat set according to known methods.

In some other examples, in addition to or as an alternative to applying adhesives to the tissue ingrowth curtain and the membrane separately or individually, the tissue ingrowth curtain (e.g., having a designated pattern) and the membrane are layered with one or more adhesives or adhesive layers therebetween, after which the layered construct is pressed and/or heat set according to known methods. The method further includes cutting the leaflet, and/or other feature of the prosthetic valve 1000, from the resulting construct according to known methods. In some examples, a final free edge cutting operation may be performed on the formed material to achieve a clean free edge according to known methods, as those of skill will appreciate.

Bio-Active Agents

Any of a variety of bio-active agents may be implemented with the materials of the prosthetic valve 1000. For example, any one or more of the leaflets 1230 and/or the leaflet frame cover 1232 and/or the anchor frame cover 1132 and/or connecting sheath 1300 and/or the outflow annular groove cover 1440 (including portions thereof) may comprise a bio-active agent. Bio-active agents can be coated onto one or more of the foregoing features for controlled release of the agents once the prosthetic valve 1000 is implanted. Such bio-active agents can include, but are not limited to, thrombogenic agents such as, but not limited to, heparin. Bio-active agents can also include, but are not limited to agents such as anti-proliferative/antimitotic agents including natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin) and mitomycin, enzymes (e.g., L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenesdacarbazinine (DTIC); anti-proliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine {cladribine}); platinum coordination complexes (e.g., cisplatin and carboplatin), procarbazine, hydroxyurea, mitotane, aminoglutethimide; hormones (e.g., estrogen); anti-coagulants (e.g., heparin, synthetic heparin salts and other inhibitors of thrombin); anti-platelet agents (e.g., aspirin, clopidogrel, prasugrel, and ticagrelor); vasodilators (e.g., heparin, aspirin); fibrinolytic agents (e.g., plasminogen activator, streptokinase, and urokinase), aspirin, dipyridamole, ticlopidine, clopidogrel, abciximab; antimigratory agents; antisecretory agents (e.g., breveldin); anti-inflammatory agents, such as adrenocortical steroids (e.g., cortisol, cortisone, fludrocortisone, prednisone, prednisolone, 6α-methylprednisolone, triamcinolone, betamethasone, and dexamethasone), non-steroidal agents (e.g., salicylic acid derivatives, such as aspirin); para-aminophenol derivatives (e.g., acetaminophen); indole and indene acetic acids (e.g., indomethacin, sulindac, and etodalac), heteroaryl acetic acids (e.g., tolmetin, diclofenac, and ketorolac), arylpropionic acids (e.g., ibuprofen and derivatives), anthranilic acids (e.g., mefenamic acid and meclofenamic acid), enolic acids (e.g., piroxicam, tenoxicam, phenylbutazone, and oxyphenthatrazone), nabumetone, gold compounds (e.g., auranofin, aurothioglucose, and gold sodium thiomalate); immunosuppressives (e.g., cyclosporine, tacrolimus (FK-506), sirolimus (rapamycin), azathioprine, and mycophenolate mofetil); angiogenic agents (e.g., vascular endothelial growth factor (VEGF)), fibroblast growth factor (FGF); angiotensin receptor blockers; nitric oxide donors; antisense oligonucleotides and combinations thereof; cell cycle inhibitors, mTOR inhibitors, growth factor receptor signal transduction kinase inhibitors; retinoids; cyclin/CDK inhibitors; HMG co-enzyme reductase inhibitors (statins); and protease inhibitors.

The scope of the concepts addressed in this disclosure has been described above both generically and with regard to specific examples. It will be apparent to those skilled in the art that various modifications and variations can be made in the examples without departing from the scope of the disclosure. Likewise, the various components discussed in the examples discussed herein are combinable. Thus, it is intended that the examples cover the modifications and variations of the scope.

What is claimed is:

1. A prosthetic valve comprising:
a leaflet frame defining a tubular shape and having a wall extending from a leaflet frame inflow end and a leaflet frame outflow end, the leaflet frame defining a leaflet frame lumen, the leaflet frame including a leaflet construct;
an anchor frame defining a tubular shape and having an anchor frame inflow end and an anchor frame outflow end, the anchor frame defining an anchor frame lumen; and
an outflow annular groove cover having a first end coupled to the anchor frame outflow end and a second end coupled to the leaflet frame outflow end, wherein the outflow annular groove cover is operable to maintain a relative position of the leaflet frame within the anchor frame lumen by virtue of an elastic bias when the prosthetic valve is in a deployed, nested configuration.

2. The prosthetic valve of claim 1, wherein the elastic bias is configured to center the leaflet frame within the anchor frame under physiologic loading conditions.

3. The prosthetic valve of claim 1, wherein the elastic bias is configured to permit resilient deflection of the leaflet frame within the anchor frame lumen to accommodate physiologic loading.

4. A prosthetic valve comprising:
a leaflet frame defining a tubular shape and having a wall extending between a leaflet frame inflow end and a leaflet frame outflow end, the leaflet frame defining a leaflet frame lumen and including a valve construct;
an anchor frame defining a tubular shape and having an anchor frame inflow end and an anchor frame outflow end, the anchor frame defining an anchor frame lumen; and
an outflow annular groove cover having a first end coupled to the anchor frame outflow end and a second end coupled to the leaflet frame outflow end, wherein the outflow annular groove cover is operable to transition between an extended configuration and a retracted configuration and is biased toward the retracted configuration.

5. The prosthetic valve of claim 4, wherein the outflow annular groove cover resists forces in opposition to the outflow annular groove cover being biased toward the retracted configuration.

6. The prosthetic valve of claim 4, wherein the outflow annular groove cover is resiliently retractable and extendible, such that the outflow annular groove cover is operable to be transitioned between the extended configuration and the retracted configuration due to an elastic bias.

7. The prosthetic valve of claim 6, wherein the outflow annular groove cover has a flatter shape in the retracted configuration compared to the extended configuration.

8. A prosthetic valve comprising:
a leaflet frame defining a tubular shape and having a wall extending from a leaflet frame inflow end and a leaflet frame outflow end, the leaflet frame defining a leaflet frame lumen, the leaflet frame including a leaflet construct;
an anchor frame defining a tubular shape and having an anchor frame inflow end and an anchor frame outflow end, the anchor frame defining an anchor frame lumen; and
an outflow annular groove cover extending from the anchor frame outflow end and the leaflet frame outflow end, wherein:
the outflow annular groove cover is operable to maintain a relative position of the leaflet frame within the anchor frame lumen by virtue of an elastic bias when the prosthetic valve is in a deployed, nested configuration;
the outflow annular groove cover is operable to transition between an extended configuration and a retracted configuration and is biased toward the retracted configuration; and
the outflow annular groove cover has a first end coupled to the anchor frame outflow end and a second end coupled to the leaflet frame outflow end.

9. The prosthetic valve of claim 8, wherein the outflow annular groove cover is operable to cover and restrict fluid flow into and out from an outflow annular groove when the prosthetic valve is in a deployed, nested configuration.

10. The prosthetic valve of claim 8, wherein the outflow annular groove cover is blood permeable in a delivery configuration.

11. The prosthetic valve of claim 8, wherein the outflow annular groove cover is configured to be less permeable to blood when the prosthetic valve is in a deployed, nested configuration compared to when the prosthetic valve is not in the deployed, nested configuration.

12. The prosthetic valve of claim 8, wherein the elastic bias is configured to center the leaflet frame within the anchor frame lumen when the prosthetic valve is in a deployed, nested configuration.

13. The prosthetic valve of claim 8, wherein when the prosthetic valve is in a delivery configuration, the outflow annular groove cover is elastically restrained in an extended tubular configuration.

14. The prosthetic valve of claim 8, wherein the outflow annular groove cover is a flexible elastic element operable to resiliently stow into a low radial profile when the prosthetic valve is in a delivery configuration.

15. The prosthetic valve of claim 8, wherein the outflow annular groove cover forms a wall that has a lower angle relative to a longitudinal axis of the prosthetic valve when the prosthetic valve is in a delivery configuration compared to when the prosthetic valve is in a deployed, nested configuration.

16. The prosthetic valve of claim 8, wherein the outflow annular groove cover, together with a connecting sheath that couples the leaflet frame to the anchor frame, defines a closed volume.

17. The prosthetic valve of claim 8, wherein the outflow annular groove cover is coupled to the leaflet frame about an outflow edge of a leaflet frame cover.

18. The prosthetic valve of claim 8, wherein the outflow annular groove cover is formed from a retracted microstructure membrane.

19. The prosthetic valve of claim 18, wherein the retracted microstructure membrane is a porous synthetic fluoropolymer membrane defining pores and an elastomer or elastomeric material filling the pores.

* * * * *